US012163183B2

(12) United States Patent
Sardar et al.

(10) Patent No.: US 12,163,183 B2
(45) Date of Patent: Dec. 10, 2024

(54) SYSTEMS AND METHODS FOR LOCALIZED SURFACE PLASMON RESONANCE BIOSENSING

(71) Applicant: INDIANA UNIVERSITY RESEARCH AND TECHNOLOGY CORPORATION, Indianapolis, IN (US)

(72) Inventors: Rajesh Sardar, Avon, IN (US); Thakshila Liyanage, Indianapolis, IN (US); Adrianna Masterson, Indianapolis, IN (US); Hristos Z. Kaimakliotis, Zionsville, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 837 days.

(21) Appl. No.: 17/283,977

(22) PCT Filed: Oct. 22, 2019

(86) PCT No.: PCT/US2019/057358
§ 371 (c)(1),
(2) Date: Apr. 9, 2021

(87) PCT Pub. No.: WO2020/086531
PCT Pub. Date: Apr. 30, 2020

(65) Prior Publication Data
US 2021/0348218 A1    Nov. 11, 2021

Related U.S. Application Data

(60) Provisional application No. 62/749,004, filed on Oct. 22, 2018.

(51) Int. Cl.
*C12Q 1/6825* (2018.01)
*G01N 21/65* (2006.01)

(52) U.S. Cl.
CPC ......... *C12Q 1/6825* (2013.01); *G01N 21/658* (2013.01)

(58) Field of Classification Search
CPC ... C12Q 1/6825; G01N 21/658; G01N 21/554
(Continued)

(56) References Cited

U.S. PATENT DOCUMENTS 5,942,397 A * 8/1999 Tarlov ............... B82Y 30/00
435/6.12
9,915,654 B2  3/2018 Raphael et al.
(Continued)

FOREIGN PATENT DOCUMENTS

EP    2613149 A1    7/2013
PL     428550 A1 *  7/2020
(Continued)

OTHER PUBLICATIONS

Gebala, M. et al. "Controlled Orientation of DNA in a Binary SAM as a Key for the Successful Determination of DNA Hybridization by Means of Electrochemical Impedance Spectroscopy." ChemPhysChem. 2010, 11. 2887-2895. (Year: 2010).*
(Continued)

*Primary Examiner* — Neil N Turk
*Assistant Examiner* — Jacqueline Brazin
(74) *Attorney, Agent, or Firm* — Barnes & Thornburg LLP

(57) ABSTRACT

Biosensors and methods for localized surface plasmon resonance biosensing are disclosed. The biosensor can include a substrate having a substrate surface to which a plurality of localized surface plasmon resonance (LSPR) antennae are affixed. The LSPR antennae can be affixed via an affixation
(Continued)

surface of the LSPR antenna. The LSPR antennae can have a functional surface opposite the affixation surface. Each functional surface can be functionalized by a plurality of single-stranded DNA.

19 Claims, 39 Drawing Sheets

Specification includes a Sequence Listing.

(58) Field of Classification Search
USPC .................................................. 435/287.2
See application file for complete search history.

(56) References Cited

U.S. PATENT DOCUMENTS

| | | | |
|---|---|---|---|
| 2003/0049639 | A1 | 3/2003 | Nelson et al. |
| 2012/0101007 | A1 | 4/2012 | Ahern et al. |
| 2013/0148194 | A1 | 6/2013 | Altug et al. |
| 2013/0190192 | A1 | 7/2013 | Lowe |
| 2014/0154668 | A1 | 6/2014 | Chou et al. |
| 2017/0023599 | A1* | 1/2017 | Richards .......... G01N 35/00069 |
| 2017/0298426 | A1* | 10/2017 | Sardar .................. C12Q 1/6825 |

FOREIGN PATENT DOCUMENTS

| | | |
|---|---|---|
| WO | 2011/109364 A2 | 9/2011 |
| WO | 2013/121011 A1 | 8/2013 |
| WO | 2013/160836 A1 | 10/2013 |

OTHER PUBLICATIONS

PCT International Search Report and Written Opinion completed by the ISA/US on Dec. 19, 2019 and issued in connection with PCT/US2019/057358.
(Gebala, M et al.) Controlled Orientation of DNA in a Binary SAM as a Key for the Successful Determination of DNA Hybridization by Means of Electrochemical Impedance Spectroscopy. Chemphyschem. Sep. 10, 2010, vol. 11, No. 13; pp. 2887-2895; p. 2888, 1st column, 3rd paragraph; p. 2891, 1st column, 3rd paragraph; p. 2892, 1st paragraph, 2nd-3rd paragraphs; DOI: 10.1002/cphc.201000210.
Joshi et al. "Improved localized surface plasmon resonance biosensing sensitiviy based on chemically-synthesized gold nanoprisms as plasmoinic transducers," Journal of Materials Chemistry, 2012, 22 pp. 923-931.
Li et al., "Plasmonic nanorice antenna on triangel nanoarray for surface-enhanced raman scattering detection of hepatitis B virus DNA", Analytical Chemistry, Jan. 15, 2013, 85 pp. 2072-2078.
Sipova et al., "Surface plasmon resonance biosensor for rapid label-free detection of microribonucleic acid at subfemtomole level," Analytical Chemistry, Dec. 15, 2010, 82 pp. 10110-10115.
Filmetrics. Refractive Index of SiO2, Fused Silica, Silica, Silicon Dioxide, Thermal Oxide, ThermalOxide. Jan. 9, 2012. paragraph 2 URL:https://web.archive.Org/web/20120109021016/http://www.filmetrics.com/refractive-index- databas e/SiO2/Fused-Silica-Silicon-Dioxide-Thermal-Oxide-ThermalOxide, 2 pages.
Joshi, et al., "Designing Efficient Localized Surface Plasmon Resonance-Based Sensing Platforms: Optimization of Sensor Response by Controlling the Edge Length of Gold Nanoprisms," 2012, The Journal of Physical Chemistry, 116 pp. 20990-21000.
Joshi, et al., "Temperature-Controlled Reversible Localized Surface Plasmon Resonance Response of Polymer- Functionalized Gold Nanoprisms in the Solid Stale," 2013, ,J. Phys. Chem. C, 117 pp. 26228-26237.
Joshi, el al., "Ultrasensilive Photoreversible Molecular Sensors of Azobenzene Functionalized Plasmonic Nanoantennas," 2014, Nano Letters 14, pp. 532-540.
Lawrence, et al., "Solvent-like ligand-coaled ultrasmall cadmium selenide nanocrystals: strong electronic coupling in a self-organized assembly," 2015, Nanoscale, 7 pp. 11667-11677.
Liu, et al., "Cdk4/6 Inhibition Induces Epilhelial-Mesenchymal Transition and Enhances Invasiveness in Pancreatic Cancer Cells," 2012, Mol. Cancer Ther., 11 pp. 2138-2148.
Livak, et al., "Analysis of Relative Gene Expression Data Using Real-Time Quantitative PCT and the 2-Delta-Delta-CT Method," 2011, Methods, 25 pp. 402-408.
Ouyang, et al., "MicroRNA-10b enhances pancreatic cancer cell invasion by suppressing TIP30 expression and promoting EGF and TGF-[beta] actions," 2014, Oncogene, 33 pp. 4664-4674.
Qavi, et al., "Multiplexed Detection and Label-Free Quantitation of microRNAs using Arrays of Silicon Photonic Microring Resonators," 2010, Angew Chem Int Ed Engl., 49, pp. 1-9.
Ren, et al., "A Highly Sensitive and Selective Electrochemical Biosensor for Direct Detection of MicroRNAs in Serum," 2013, Anal. Chem., 85 pp. 4784-4789.
Steel, et al., "Immobilization of Nucleic Acids at Solid Surfaces: Effect of Oligonucleotide Length on Layer Assembly," 2000, Biophysical Journal, 79, pp. 975-981.
Yanli, "Ternary Sensing Surface with DNA-Based Spacer Group: Characterization, Comparison and Optimization," 2013, Nanyang Technological University, School of Materials Science and Engineer, Abstract, 14 pages.
International Search Report and Written Opinion from PCT/US2015/054174, dated Jan. 12, 2016, 23 pages.
Bain, Colin D. et al., "Formation of Monolayers by the Coadsorption of Thiols on Gold: Variation in the Head Group, Tail Group, and Solvent", J. Am. Chem. Soc., Aug. 1, 1989, vol. 111, No. 18, 7155-7164, DOI: 10.1021/ja00200a039.
Masterson, Adrianna N et al. "Enhancing Nonfouling and Sensitivity of Surface-Enhanced Raman Scattering Substrates for Potent Drug Analysis in Blood Plasma via Fabrication of a Flexible Plasmonic Patch." Analytical chemistry, vol. 93,4 (2021): 2578-2588. doi: 10.1021/acs.analchem.0c04643.
Ohtake et al., "Effect of Hydrocarbon Chain Length on Arrangement of Chemically Adsorbed Monolayers", Langmuir, Sep. 1, 1992, vol. 8, No. 9, 2081-2083, DOI: 10.1021/la00045a001.

* cited by examiner

```
ssDNA-10b: 5'CACAAA TTCGGTT CT ACAGGGTA3'
  miR-10b: 3'GUGUUUAAGCCAAGA UGUCCCAU5'
  miR-10a: 3'GUGUUUAAGCCUAGAUGUCCCAU5'
  miR-p  : 3'GUGUUUAAGCCAAGAUGGCCCAU5'
  miR-q  : 3'GUGCUUAAGCCAAGAUGUCCCAU5'
  miR-v  : 3'      UUUAAGCCAAGAUGUCCCAU5'
```

SYSTEMS AND METHODS FOR LOCALIZED SURFACE PLASMON RESONANCE BIOSENSING

CROSS REFERENCE TO RELATED APPLICATIONS

This application is a U.S. national counterpart application of international application serial No. PCT/US2019/057358 filed Oct. 22, 2019, which claims priority under 35 U.S.C. § 119(e) to U.S. Provisional Patent Application No. 62/749,004 filed on Oct. 22, 2018, the disclosures of both of which are hereby expressly incorporated by reference in their entireties.

STATEMENT REGARDING FEDERALLY SPONSORED RESEARCH

This invention was made with government support under 1604617 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Oct. 11, 2019, is named 29920-299276_SL.txt and is 7,597 bytes in size.

BACKGROUND

Technical Field: The field of the disclosure is biosensing. More particularly, the disclosure relates to localized surface plasmon resonance biosensing.

MicroRNAs (miRs) are small noncoding RNAs that regulate messenger RNA (mRNA) stability and/or translation. Due to their release into the circulation and their remarkable stability, miR levels in plasma and other biological fluids can serve as diagnostic and prognostic disease biomarkers. miRs target specific mRNAs and have been implicated as key regulators in numerous biological processes including gene expression. Over 1500 miRs have been identified in humans and shown that they cause variable expression (up or down) in various human diseases, and thus miRs have the ability to serve as diagnostic and prognostic markers. To fully understand the role of miRs in various diseases, it is important to detect and quantify circulating miR levels directly in biological fluids. Although the therapeutic potential of miRs is in its infancy, altered miR expression levels have been associated with a wide range of diseases including cancer, diabetes, heart disease, and possibly Alzheimer's disease. Plasma miRs are remarkably stable under harsh conditions, therefore they have the potential to serve as diagnostic markers for these and other diseases. Quantitative measurement of miRs in unmodified plasma and/or serum, and in biological compartments (e.g., cells and cell containing compartments), is crucial for developing a mechanistic understanding of the release of miRs in circulation and the role of miRs in various cellular processes, and may provide a unique opportunity for developing diagnostic and prognostic markers for many diverse conditions. However, quantifying miRs in the circulation is challenging due to issues with sensitivity and specificity. Currently, microarrays and qRT-PCR assays are routinely used to detect miRs. However, these semi-quantitative methods require sequence-based amplification and radioactive labeling steps, and suffer from cross-hybridization and invalid internal controls. Other techniques such as fluorescence-, electronic-, electrochemical-, silicon nanowire-, microring resonator-, microcantilever-, and nanopore-based techniques for analyzing miRs either require fluorescent or protein labeling, or they are non-regenerative, and have demonstrated inability for use in biological fluids. These assays are also incapable of multiplex sensing, an essential prerequisite for commercialization and high-throughput screening in clinical setup. Microring resonator- and surface enhanced Raman spectroscopy-based assays can perform multiplexing assays but fail to work directly in biological fluids. The complexity (reverse transcription, labeling, and amplification) and multiple time consuming steps (treatment of the biological fluids and RNA extraction) required for existing real-time PCR- and microarray-based quantification methods prevent the transfer of these strategies not only for more sensitive research assays, but also precludes their use in clinical point-of-care diagnosis.

Pancreatic ductal adenocarcinoma (PDAC)-related deaths are a major health concern in the United States since the five-year survival rate is only 6%. A crucial contributor to this dismal statistic is the absence of a biomarker for early PDAC detection. Moreover, most patients with PDAC do not develop specific symptoms until the disease is quite advanced. Therefore, at clinical presentation, PDAC patients often have locally advanced and/or metastatic disease, which precludes effective therapy in the vast majority of patients. In this context miRs (miRs), which are small single-stranded, non-coding RNAs often play a major role in cell proliferation, survival, migration, invasion, and metastasis in various cancers, including PDAC. Moreover, miRs are released into the circulation, where they exhibit remarkable stability. Therefore, the development of sensitive and specific detection techniques, which precisely and quantitatively measure the concentration of miRs in their native environments such as blood or plasma, may provide a unique opportunity for developing diagnostic and prognostic markers in PDAC.

Microarrays and quantitative reverse transcription polymerase chain reaction (qRT-PCR) assays are routinely used to detect miRs. However, these methods are semi-quantitative, require sequence-based amplification and radioactive labeling steps, and suffer from cross-hybridization and invalid internal controls. Other analytical techniques such as electrochemical and fluorescence-based assays are also used to quantify the miRs. However, such techniques require either additional amplification or labeling, or complex electron/energy transfer processes, and cannot be performed in physiological media. A few label-free techniques such as photonic microring resonators, nanopores, and nanoparticle-based bio-barcode gel assay can detect miRs associated with cancer patients. However, microring resonators suffer from low sensitivity and do not work in physiological media. Although nanopore-based sensors have shown the ability to detect miRs in the circulation of lung cancer patients, the technique requires a complicated fabrication procedure, a high probe concentration, and a specific probe signature. The bio-barcode gel technique relies on complex sandwich type capturing methods, uses of the toxic chemical potassium cyanide, and may not be applicable to clinically relevant patient samples.

Plasmonic nanostructures have gained significant attention because of their geometrical feature-dependent localized surface plasmon resonance (LSPR) properties, which can be further controlled by modulating their local dielectric environment. Utilizing these properties, several molecular and biological sensors have been developed where analyte binding to nanostructure surface-bound receptors results in an increase in refractive index and consequently a LSPR peak shift. In this context, it has not been possible to detect and quantify sequence specific miRs by their direct hybridization to nanostructure probes followed by monitoring the LSPR properties of nanostructures without using labeling steps.

Delocalization of surface plasmon excitation (conduction electrons) of metallic nanoparticles is a steady-state electronic phenomenon in which wavefunctions of conduction electrons are expected to leave the metallic construct and expand into the surrounding environment, including into ligand moieties. When this occurs, the electron density around the nanoparticle reduces, resulting in the LSPR peak red-shifts. Light irradiation onto the metallic construct induces the collective oscillation of conduction electrons and creates the LSPR properties. The electron wavefunctions then delocalize through a highly pi-stacked -ssDNA/miR duplex.

Charge transfer through duplex DNA and/or DNA/miR helices is considered a key electronic phenomena for control of various biological functions such as recognition, signaling, and repair of DNA damage. However, whether or not the duplex is capable of delocalizing electrons and allowing long-range CT to occur along the backbone remains unanswered. By utilizing gold nanoprisms as electron donors and their unique LSPR properties as a transduction method, our experimental investigation will probe the electron delocalization and/or CT properties of short DNA molecules. This knowledge can be translated to other electron donors such as quantum dots, metal oxides, and graphene to fabricate miniaturize optoelectronic devices.

Design of every LSPR-based biosensor requires functionalization of a nanostructure surface with ligands containing bio-recognition molecules, but a quantitative understanding is still lacking on how to enhance the sensitivity of the assay by using the most appropriate surface chemistry. To prepare self-assembled sensors with unique functions and applications, a more sophisticated fabrication method is needed to predict how surface ligand structural parameters influence nanostructure behavior during sensor development.

Accordingly, it would be beneficial to provide a biosensor that overcomes the aforementioned drawbacks.

SUMMARY

The present disclosure overcomes the aforementioned drawbacks by providing systems and methods for localized surface plasmon resonance biosensing.

In one aspect, this disclosure provides a biosensor. The biosensor can include a substrate having a substrate surface to which a plurality of localized surface plasmon resonance (LSPR) antennae are affixed. The LSPR antennae can be affixed via an affixation surface of the LSPR antenna. The LSPR antennae can have a functional surface opposite the affixation surface. Each functional surface can be functionalized by a plurality of single-stranded DNA.

In another aspect, this disclosure provides a method of detecting the presence of or quantifying the amount of a miR of interest in a medium suspected of containing the miR of interest. The method can include one or more of the following steps: contacting a biosensor with the medium, the biosensor including a plurality of localized surface plasmon resonance (LSPR) antennae affixed to a substrate surface, each LSPR antenna having a functional surface functionalized by a plurality of single-stranded DNA (ssDNA) that is complementary to at least a portion of the miR of interest; measuring an absorption spectrum of the plurality of LSPR antennae, the absorption spectrum having a peak wavelength; and determining the presence of the miR of interest in the medium based on the peak wavelength.

In yet another aspect, this disclosure provides a method of diagnosing a disease state in a subject, wherein the disease state is indicated by the presence or level of a miR of interest in a serum sample from the subject. The method can include one or more of the following steps: contacting a biosensor with the serum sample, the biosensor including a plurality of localized surface plasmon resonance (LSPR) antennae affixed to a substrate surface, each LSPR antenna having a functional surface functionalized by a plurality of single-stranded DNA (ssDNA) that is complementary to at least a portion of the miR of interest; measuring an absorption spectrum of the plurality of LSPR antennae, the absorption spectrum having a peak wavelength; determining a concentration of the miR of interest in the serum sample based on the difference between the peak wavelength and an unbound absorption peak wavelength that is measured in the absence of the miR; and diagnosing the disease state or altering a treatment regimen based on the peak wavelength or the difference between the peak wavelength and unbound absorption peak wavelength.

In another aspect, this disclosure provides kits including a biosensor and a plurality of single-stranded DNA (ssDNA). The biosensor can include a substrate having a substrate surface to which a plurality of localized surface plasmon resonance (LSPR) antennae are affixed, the LSPR antennae affixed via an affixation surface of the LSPR antenna, the LSPR antennae including a functional surface opposite the affixation surface. The plurality of ssDNA can be adapted to functionalize the functional surface.

The foregoing and other aspects and advantages of the disclosure will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

A representative listing of sequence identifiers is as follows:
SEQ ID NO: 1 is ssDNA-21
SEQ ID NO: 2 is ssDNA-10b with a 5' Thiol-$(CH_2)_6$ Modification
SEQ ID NO: 3 is miR-21
SEQ ID NO: 4 is miR-10b
SEQ ID NO: 5 is miR-16
SEQ ID NO: 6 is miR-126
SEQ ID NO: 7 is miR-141
SEQ ID NO: 8 is miR-122
SEQ ID NO: 9 is miR-10a
SEQ ID NO: 10 is ssDNA-10b
SEQ ID NO: 11 is ssDNA-182
SEQ ID NO: 12 is ssDNA-145
SEQ ID NO: 13 is ssDNA-10b with a 3' Thiol-$(CH_2)_3$ Modification
SEQ ID NO: 14 is ssDNA-182 with a 3' Thiol-$(CH_2)_3$ Modification
SEQ ID NO: 15 is ssDNA-145
SEQ ID NO: 16 is ssDNA-143
SEQ ID NO: 17 is ssDNA-10b with a 5'Thiol $C_6$/iSp $(CH_2)_3$ Modification
SEQ ID NO: 18 is miR-182

SEQ ID NO: 19 is miR-145
SEQ ID NO: 20 is miR-143
SEQ ID NO: 21 is miR-p
SEQ ID NO: 22 is miR-q
SEQ ID NO: 23 is miR-r
SEQ ID NO: 24 is miR-s
SEQ ID NO: 25 is miR-t
SEQ ID NO: 26 is miR-v
SEQ ID NO: 27 is miR-w
SEQ ID NO: 28 is ssDNA-96
SEQ ID NO: 29 is ssDNA-490-5p
SEQ ID NO: 30 is miR-96
SEQ ID NO: 31 is miR-490-5p

Brief Description of the Drawings

FIG. 15C discloses SEQ ID NOS: 10, 4, 21, 9, 22, and 23, respectively in order of appearance.

FIG. 22 is a graph showing the comparison of miR concentration in nano molar to $\Delta\lambda_{LSPR}$ in nanometers, wherein the biosensor comprised a ssDNA-10b and the (//) bar represents the interaction between the biosensor and miR-10b and the (\\) bar represents the interaction of ssDNA-10b with miR-10a.

FIG. 23 shows the comparison of exemplary miR sequences (FIG. 23 discloses SEQ ID NOS: 10, 4, 9, 21, and 26, respectively, in order of appearance)

DETAILED DESCRIPTION

Figure 1:
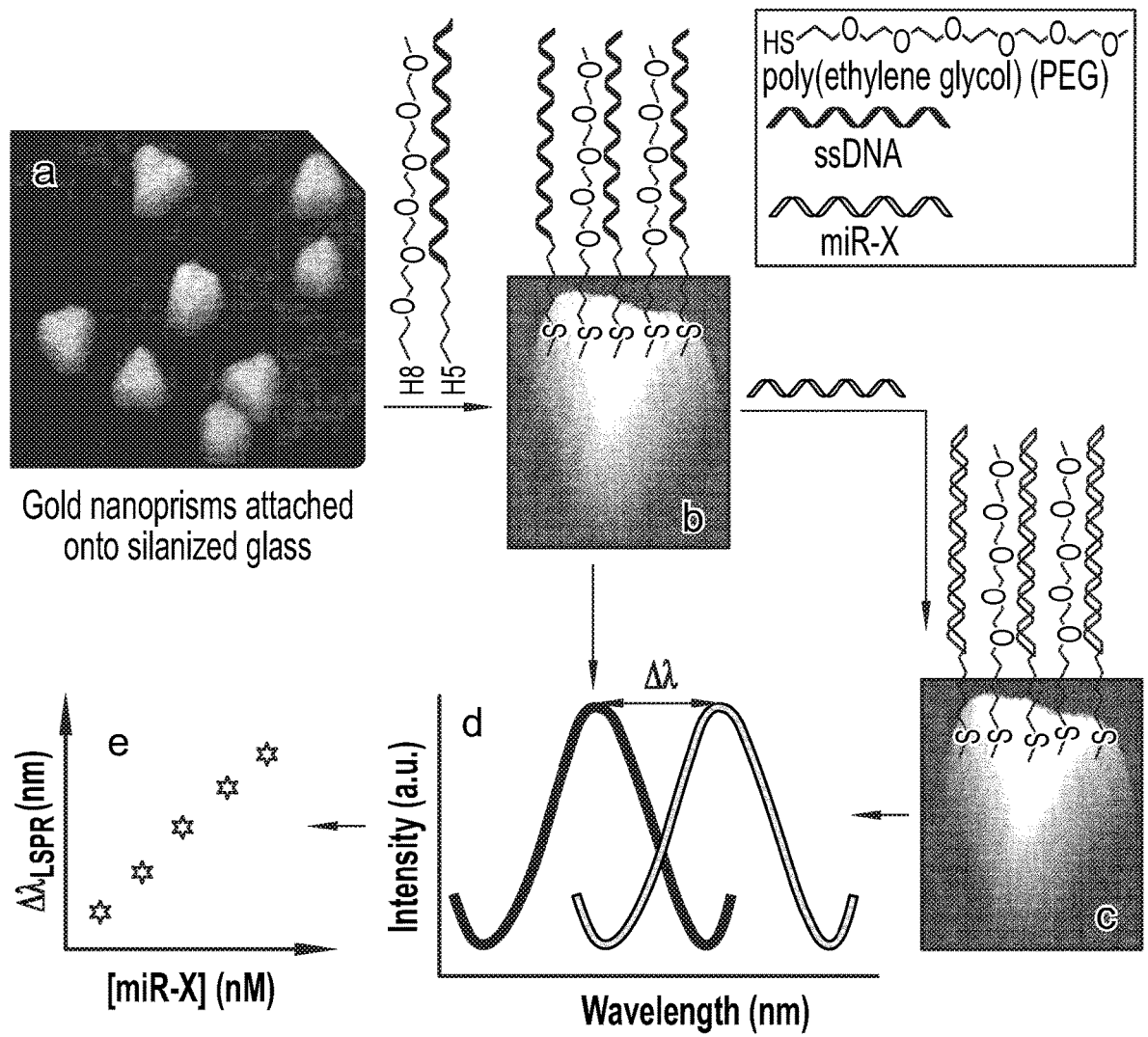
FIG. 1A-1E shows the design of plasmonic biosensors and detecting miR-X in various physiological media. (a) Chemically-synthesized and freshly prepared gold nanoprisms were covalently attached onto a 3-mercaptopropyl-triethoxy silane-functionalized glass coverslip (substrate). (b) Surface of gold nanoprism was chemically modified with a 1 µM 1:1 mixture of SH-C6-ssDNA-X and PEG6-SH in PBS buffer (pH 7.4) to prepare the plasmonic biosensor. The extinction spectra of the biosensor were collected in PBS buffer to determine the LSPR dipole peak position (first curve in (d). (c) Incubation of sensor in miR-X solution and formation of DNA duplex. After carefully rinsing with PBS buffer, extinction spectra were recorded (second curve in (d)) to determine the new LSPR dipole peak position. (d) The extent of dipole peak shift ($\Delta\lambda_{LSPR}$) depends on the concentration of miR-X used during the incubation in (c), which ranged from 100 nM to 50 fM. (e) is a plot of $\Delta\lambda_{LSPR}$ vs. log of miR-X concentrations used to determine the limit of detection.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Features of this disclosure described with respect to a particular method, apparatus, composition, or other aspect of the disclosure can be combined with, substituted for, integrated into, or in any other way utilized with other methods, apparatuses, compositions, or other aspects of the disclosure, unless explicitly indicated otherwise or necessitated by the context. For clarity, an aspect of the invention described with respect to one method can be utilized in other methods described herein, or in apparatuses or with compositions described herein, unless context clearly dictates otherwise.

This disclosure is based on the discovery that a plurality of localized surface plasmon resonance antennae having single-stranded DNA (ssDNA) affixed to their surface have an absorption peak wavelength shift or a full width at half maximum (FWHM) shift when the antennae are contacted by a miR of interest that is complementary to the ssDNA. This discovery has led to the creation of biosensors, methods, and kits that can provide a low limit of detection for sensing the presence of the miR. This disclosure is also based on the discovery that the absorption peak wavelength shift or FWHM shift is proportional to the concentration of miR of interest in a sample, thus allowing the concentration to be determined by measuring the absorption peak wavelength shift.

Biosensors

This disclosure provides a biosensor. The biosensor can include one or more of the following: a substrate having a substrate surface; and a localized surface plasmon resonance (LSPR) antenna affixed to a substrate surface. In some aspects, the biosensor can have a plurality of LSPR antennae affixed to the substrate surface.

The LSPR antennae can include an affixation surface and a functional surface. The LSPR antennae can be affixed via the affixation surface of the LSPR antenna. The functional surface can be opposite the affixation surface. Each functional surface can be functionalized by a plurality of single-stranded DNA (ssDNA). In certain aspects, the affixation surface and the functional surface are substantially parallel to one another.

In certain aspects, the ssDNA can be complementary to at least a portion of a miR of interest. In certain aspects, the ssDNA can be complementary to the miRs of interest disclosed herein. In certain aspects, the ssDNA has a sequence that is the sequence of ssDNA-10b or ssDNA-21.

In certain aspects, the ssDNA can include between 15 and 30 nucleotides or between 20 and 25 nucleotides. In certain aspects, the ssDNA can include 22 or 23 nucleotides.

In certain aspects, the ssDNA can comprise a functional moiety that enables binding to the functional surface. In certain aspects, the functional moiety can be a thiol functional moiety, an amine functional moiety, a carboxylate functional moiety, a phosphonate functional moiety, or a combination thereof. The functional moiety can be located at a terminal end of the ssDNA. In certain aspects, the functional moiety can be located at the 5'-terminal end of the ssDNA.

In certain aspects, the ssDNA can be bound to the functional moiety via a linker moiety. The linker moiety can be selected from the group consisting of an alkyl moiety, an alkenyl moiety, an alkynyl moiety, a saturated and/or unsaturated ring moiety, a short chain alkyl moiety, a polyethylene glycol moiety, and combinations thereof. In certain aspects, the linker moiety can include two or more conjugated double bonds.

In certain aspects, the functional surface can be functionalized by a plurality of spacer molecules. The plurality of spacer molecules can comprise a spacer tail moiety. In certain aspects, the spacer tail moiety can be a poly-ethylene glycol moiety, an alkyl moiety, or a combination thereof. The plurality of spacer molecules can comprise a spacer functional moiety. In certain aspects, the spacer functional moiety can be a thiol functional moiety, an amine functional moiety, a carboxylate functional moiety, a phosphonate functional moiety, or a combination thereof. As with the ssDNA, the functional moiety on the spacer molecule can enable binding to the functional surface.

In certain aspects, the functional surface can have a ratio of number of ssDNA to number of spacer molecules between 1:99 and 99:1, between 1:50 and 50:1, between 1:25 and 25:1, between 1:10 and 10:1, between 1:5 and 5:1, between 1:3 and 3:1, between 1:2 and 2:1, or about 1:1.

In certain aspects, the plurality of LSPR antennae can comprise gold, silver, copper, palladium, aluminum, or a combination thereof. In some embodiments, the LSPR antenna may be triangular nanoprisms, nanorods, or spherical particles. The plurality of LSPR antennae can be a plurality of nanoprisms. As used herein, "nanoprism" refers to a nanostructure having two faces that are substantially parallel to one another. The functional surface can be substantially triangular, substantially circular, substantially ovular, substantially quadrilateral, substantially star-shaped, or a combination thereof. In some embodiments, the functional surface comprises a sharp point. Each of the plurality of LSPR antennae can have an average edge-length of between 10 nm and 150 nm, between 20 nm and 75 nm, between 25 nm and 50 nm, between 30 nm and 45 nm, or between 33 nm and 40 nm. In certain aspects, each of the plurality of LSPR antennae can have an average edge-length of 34 nm, 35 nm, 42 nm, or 47 nm.

In certain aspects, the substrate can be substantially transparent to electromagnetic radiation having a wavelength between 350 nm and 1200 nm or between 700 nm and 900 nm. In certain aspects, the substrate can comprise glass, quartz, indium tin oxide, optical fiber, flexible plastic, gold-coated glass, sapphire, or a combination thereof. In certain aspects, the substrate can be silanized glass.

In certain aspects, the LSPR antennae can have an unbound absorption peak wavelength when contacted by a medium lacking a miR of interest that has a sequence that is at least partially complementary to the ssDNA and a bound absorption peak wavelength when contacted by a medium containing miR of interest, wherein the bound absorption peak wavelength is shifted relative to the unbound absorption peak wavelength by an amount proportional to the concentration of the miR of interest in the medium. In certain aspects, the LSPR antennae can have an unbound full width at half maximum (FWHM) when contacted by a medium lacking a miR of interest that has a sequence that is at least partially complementary to the ssDNA and a bound FWHM when contacted by a medium containing miR of interest, wherein the bound FWHM is shifted relative to the unbound FWHM by an amount proportional to the concentration of the miR of interest in the medium.

It should be appreciated that the medium can be selected from media in which the miR of interest is stable, the base-pairing interaction between the miR of interest and ssDNA are not interrupted, and which are not corrosive or destructive to the LSPR antennae, the substrate, the ssDNA, or the spacer molecules. In certain aspects, the medium can be selected from the group consisting of human plasma, lymph fluid, bovine plasma, phosphate buffered saline, water, serum, whole blood, pancreatic juice, urine, bile juice, saliva, liquid stool, peritoneal fluid, cerebrospinal fluid, and combinations thereof.

In certain aspects, the biosensors described herein function without labeling or amplification of the miR of interest.

In certain aspects, the biosensors described herein can have a limit of detection of the miR of interest of less than 50 fM, less than 40 fM, less than 30 fM, less than 25 fM, less than 10 fM, less than 1 fM, less than 500 aM, less than 100 aM, less than 50 aM, less than 25 aM, less than 10 aM, less than 1 aM, less than 500 zM, or less than 100 zM.

The biosensors described herein can have selectivity for miR of interest having only 1 nucleotide difference from another miR. For example, the biosensors described herein can distinguish between miR-10a and miR-10b, as well as other pairs of miR that differ by only a single nucleotide. As an illustrative example, the biosensors described herein can distinguish between a miR and a miR* although both come from the same precursor but the miR* may be less predominant.

In certain aspects, the miR of interest can be a member of the let 7 miR family, -5p miRs, miR-3p miRs, edited miRs, loop miRs, and the like. In certain aspects, the miR of interest can be miR-7, miR-7-2, miR-7-2*, miR-9*, miR-10a, miR-10b, miR-15a, miR-15b, miR-16, miR-16-1, miR-16-2, miR-17, miR-18a, miR-18b, miR-19a, miR-19a*, miR-19b* miR-19b, miR-19b-2, miR-20a, miR-20b, miR-21, miR-21*, miR-22, miR-22-3p, miR-23a, miR-23a*, miR-24, miR-24*, miR-24-2*, miR-25, miR-25*, miR-26a, miR-26b, miR-27a, miR-27a*, miR-27b, miR-27b*, miR-28, miR-28-3p, miR-29a, miR-29a*, miR-29b, miR-29c, miR-29c*, miR-30a*, miR-30a-3p, miR-30a-5p, miR-30b, miR-30c, miR-30c-1, miR-30c-2, miR-30d, miR-30e, miR-30e*, miR-31, miR-31*, miR-32, miR-33a, miR-33a*, miR-33a-loop, miR-34a, miR-34b*, miR-34a-loop, miR-34c-5p, miR-92a, miR-92a*, miR-92b, miR-92b*, miR-93, miR-93* miR-95, miR-96, miR-99a, miR-99b, miR-99b*, miR-100, miR-100*, miR-101, miR-101*, miR-103, miR-103a, miR-106a, miR-106b, miR-106b*, miR-107, miR-122, miR-124, miR-124*, miR-125a, miR-125b, miR-125b-1, miR-125b-2, miR-126, miR-126*, miR-128, miR-129-1, miR-129-2, miR-129-3p, miR-129-5p, miR-130a, miR-130b, miR-130b*, miR-132, miR-133a, miR-133a*, miR-133b, miR-134, miR-135b, miR-135b*, miR-136, miR-136*, miR-139, miR-140, miR-140-3p, miR-141, miR-141*, miR-142, miR-142-3p, miR-143, miR-143*, miR-144*, miR-145, miR-146a, miR-147, miR-147b, miR-148a, miR-148a*, miR-148b, miR-148b*, miR-150, miR-151, miR-153, miR-154, miR-154*, miR-155, miR-181a, miR-181a*, miR-181a-2, miR-181a-2*, miR-181b, miR-181c, miR-182, miR-183, miR-184, miR-185, miR-186, miR-187, miR-190, miR-190a, miR-190b, miR-191, miR-192, miR-192-loop, miR-193b, miR-193b*, miR-193b-3p, miR-194, miR-194* miR-195, miR-196, miR-196a, miR-196b, miR-198, miR-199a-3p, miR-199a-5p, miR-199b-3p, miR-199b-5p, miR-200a, miR-200b, miR-200c, miR-200c*, miR-203, miR-204, miR-205, miR-208, miR-210, miR-212, miR-215, miR-216, miR-216a, miR-216b, miR-217, miR-218-1, miR-218-2, miR-219-1-3p, miR-219-2, miR-219-3p, miR-219-5p, miR-219-loop, miR-219-2-loop, miR-221, miR-222, miR-222*, miR-223, miR-223*, miR-301a, miR-320a, miR-320b, miR-320b*, miR-323-3p, miR-324, miR-324-3p, miR-330-5p, miR-331, miR-331-3p, miR-335, miR-337-3p, miR-338-5p, miR-339, miR-340, miR-342, miR-342-3p, miR-342-5p, miR-345, miR-361, miR-362, miR-362-3p, miR-363, miR-365, miR-369*, miR-370, miR-373, miR-374a, miR-374a*, miR-375, miR-376a, miR-376a-1, miR-376b, miR-376c, miR-377, miR-377*, miR-379, miR-379*, miR-381, miR-381*, miR-382, miR-383, miR-409*, miR-410*, miR-411, miR-411*, miR-421, miR-423-5p, miR-431, miR-432, miR-432*, miR-433, miR-449a, miR-449b, miR-450b-5p, miR-451, miR-451a, miR-452, miR-454, miR-455, miR-455-3p, miR-484, miR-486, miR-486-3p, miR-486-5p, miR-487b, miR-490-3p, miR-492, miR-493*, miR-494, miR-497, miR-497*, miR-499-5p, miR-501*, miR-501-5p, miR-505, miR-508-3p, miR-509-5p, miR-512-3p, miR-513-3p, miR-516a-1, miR-516a-2, miR-516a-3p, miR-516b-1, miR-518d-3p, miR-518e, miR-518f, miR-520c-3p, miR-532, miR-539, miR-542*, miR-542-5p, miR-543, miR-548am, miR-548au, miR-548c, miR-548o, miR-548b-5p, miR-551b, miR-551b*, miR-552, miR-554, miR-566, miR-571, miR-575, miR-582, miR-582-3p, miR-584, miR-589, miR-589*, miR-590-5p, miR-592, miR-598, miR-604, miR-605, miR-614, miR-615, miR-616, miR-616*, miR-622, miR-625, miR-627, miR-628-3p, miR-635, miR-636, miR-639, miR-640, miR-641, miR-642b, miR-642b-3p, miR-643, miR-644, miR-646, miR-648, miR-649, miR-650, miR-652, miR-654*, miR-654-5p, miR-656, miR-672, miR-708, miR-711, miR-744*, miR-762, miR-766, miR-769-5p, miR-801, miR-874, miR-875-5p, miR-877, miR-885-5p, miR-886-5p, miR-888, miR-889, miR-889*, miR-891a, miR-922, miR-923, miR-935, miR-937, miR-939, miR-941, miR-944, miR-1207, miR-1246, miR-1288, miR-1295, miR-1468, miR-1909, miR-2355, miR-2964a, miR-3125, miR-3154, miR-3177, miR-3184, miR-3188, miR-3605, miR-3942, miR-4253, miR-4286, miR-4529, miR-4646, miR-4653, miR-4666, miR-4667, miR-4697, miR-4716, miR-4720, miR-4758, miR-4760, miR-4776-1, miR-4776-2, let-7a-2, let-7a*, let-7b, let-7c, let-7d, let-7e, let-7f, let-7g, let-7i, and the like.

The biosensors can further include any features, structures, chemicals, or reagents described herein.

Methods of Detecting or Quantifying MiRs

This disclosure also provides a method of detecting the presence of or quantifying the amount of a miR of interest in a medium suspected of containing the miR of interest. The method can include one or more of the following steps: contacting a biosensor having a plurality of antennae as described herein with the medium; measuring an absorption spectrum of the LSPR antenna, the absorption spectrum having a peak wavelength; and determining the presence of the miR in the medium based on the peak wavelength. The method can further include determining a concentration of the miR of interest in the medium based on the difference between the peak wavelength and an unbound absorption peak wavelength that is measured in the absence of the miR of interest.

This disclosure further provides a method of detecting the presence of or quantifying the amount of a miR of interest in a cellular compartment suspected of containing the miR of interest. The method can include one or more of the following steps: isolating the cellular compartment; extracting RNA from the isolated cellular compartment; suspending the extracted RNA in a medium; contacting a biosensor with the medium containing the extracted RNA, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the miR of interest; measuring an absorption spectrum of the LSPR antenna, the absorption spectrum having a peak wavelength; and determining the presence of or quantifying the amount of the miR of interest in the cellular compartments based on the peak wavelength. The method can also be applied to a plurality of cellular compartments.

This disclosure also provides a method of detecting the presence of or quantifying the amount of a miR of interest in a cellular compartment suspected of containing the miR of interest. The method can include one or more of the following steps: isolating the cellular compartment; contacting a biosensor with the cellular compartment, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the miR of interest; measuring an absorption spectrum of the LSPR antenna, the absorption spectrum having a peak wavelength; and determining the presence of or quantifying the amount of the miR of interest in the cellular compartments based on the peak wavelength. The method can also be applied to a plurality of cellular compartments.

In certain aspects, the methods described above can be adapted to further determine the presence of or quantify the amount of miR in a supernatant from one or more centrifugation steps in processing a sample. For example, when isolating the cellular compartment or compartments, a biological sample can be centrifuged. The supernatant can be used to contact the biosensor as described elsewhere herein, and the presence or quantity of miR in the supernatant can be determined.

In certain aspects, the contacting step can include an incubation time. In principle the incubation time can be a length of time that is sufficient to allow the complexing between the miR of interest and the corresponding ssDNA. Of course, the ideal time is the length of time required to allow the complexing to occur, and not longer than that amount of time. Nonetheless, this disclosure encompasses all functional incubation times, whether shorter or longer than is absolutely ideal. The incubation time can range from 1 minute to 24 hours, from 5 minutes to 12 hours, from 30 minutes to 6 hours, from 1 hour to 5 hours, from 2 hours to 4 hours, from 2.5 hours to 3.5 hours, or from 1 hour to 4 hours.

In certain aspects, the contacting step can include an incubation temperature. In principle, the incubation temperature can be a temperature that is suitable for the complexing between the miR of interest and the corresponding ssDNA. Of course, certain temperatures are preferable to others due to the thermodynamics of the complexing process. Nonetheless, this disclosure encompasses all functional incubation temperatures, whether higher or lower than is absolutely ideal. The incubation temperature can range from 0° C. to 50° C., from 5° C. to 40° C., from 10° C. to 30° C., from 20° C. to 25° C. The incubation temperature can be room temperature. The incubation temperature can be 5° C.

In certain aspects, determining the concentration can include using a calibration curve.

In certain aspects, the method further comprises contacting the biosensor with a cleaving enzyme to separate the miR of interest from the ssDNA thus regenerating the biosensor.

In certain aspects, the methods do not require labeling or amplification of the miR of interest.

In certain aspects, the methods described herein can have a limit of detection of the miR of interest of less than 50 fM, less than 40 fM, less than 30 fM, less than 25 fM, less than 10 fM, less than 1 fM, less than 500 aM, less than 100 aM, less than 50 aM, less than 25 aM, less than 10 aM, less than 1 aM, less than 500 zM, or less than 100 zM.

The methods of detecting miRs can further include any features, structures, chemicals, or reagents described herein.

Methods of Diagnosing a Disease State in a Subject

This disclosure also provides a method of diagnosing a disease state in a subject, where the disease state is indicated by the presence of a miR of interest in a serum sample from the subject. The method can include one or more of the following steps: contacting a biosensor having a localized surface plasmon resonance (LSPR) antenna as described herein with the serum sample; measuring an absorption spectrum of the LSPR antenna, the absorption spectrum having a peak wavelength; determining a concentration of the miR of interest in the serum sample based on the difference between the peak wavelength and an unbound absorption peak wavelength that is measured in the absence of the miR; diagnosing the disease state or altering a treatment regimen based on the concentration of the miR of interest in the serum sample.

This disclosure further provides a method of diagnosing a disease state in a subject, wherein the disease state is indicated by the presence of a miR of interest in a cellular compartment from the subject. The method can include one or more of the following steps: isolating the cellular compartment; extracting RNA from the isolated cellular compartment; suspending the extracted RNA in a medium; contacting a biosensor with the medium containing the extracted RNA, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the miR of interest; measuring an absorption spectrum of the plurality of LSPR antennae, the absorption spectrum having a peak wavelength; determining a concentration of the miR of interest in the cellular compartment based on the difference between the peak wavelength and an unbound absorption peak wavelength that is measured in the absence of the miR; and diagnosing the disease state or altering a treatment regimen based on the concentration of the miR of interest in the cellular compartment. The cellular compartment can be an exosome. In some aspects, the method discussed in the paragraph can exclude the extracting and suspending steps, and can involve contacting the biosensor with the cellular compartment rather than with the medium.

In certain aspects, the disease state can be pancreatic ductal adenocarcinoma (PDAC), all other solid cancers and their subtypes, such as breast and ovarian cancer, uterine cancer, colorectal cancer, gastric cancer, cholangiocarcinoma, ampulla of Vater cancer, thyroid cancer, parathyroid cancer, head and neck cancer, esophageal cancer, liver cancer, kidney cancer, genito-urinary cancers, bladder and prostate cancer, mesothelioma, lung cancers, skin cancers such as basal cell carcinoma and squamous cell carcinoma and melanoma, other skin conditions such as skin rashes and psoriasis, glioblastomas and other central nervous system tumors, sarcomas, preneoplastic lesions and cystic lesions that may precede solid cancers, lympho-proliferative disorders such as leukemias, lymphomas, multiple myeloma, inherited cancers, and diseases other than cancer. Such diseases include, but are not limited to, diabetes mellitus, type I, type II, and pancreatogenic diabetes mellitus and the complications associated with these diabetes disorders, other endocrine and metabolic disorders, cardiovascular diseases include myocardial infarction, atherosclerosis, stroke, hypertension and its complications, vascular aneurysms, lipid disorders, inflammatory disorders of all organ systems including acute pancreatitis, hepatitis, cholangitis, colitis, glomerulonephritis, acute interstitial nephritis, and other acute inflammatory states, pulmonary disorders including chronic obstructive pulmonary diseases and pulmonary emboli, autoimmune disorders, gastrointestinal disorders including chronic pancreatitis, liver diseases including cirrhosis of the liver and steatohepatitis, chronic viral liver infections such as hepatitis B and C viruses, and kidney diseases, muscolo-skeletal disorders including but not limited to cancer-associated cachexia, muscular dystrophies and other degenerative muscle diseases, neuro-muscular disorders, rheumatoid arthritis, psoriatic arthritis, other inflammatory joint disease, crystal disease of the joint such as gout and pseudo-gout, degenerative arthritis, herniated disc disease, osteoporosis, ankylosing spondylitis, osteopetrosis, osteogenesis imperfect, spina *bifida*, scoliosis, spinal stenosis, traumatic spinal and brain injuries, neurological disorders such as neuro-generative disease and seizure disorders, Alzheimer's disease and other dementias, mental disorders including depression, bipolar disorders, schizophrenia, panic disorders, post-traumatic stress disorder (PTSD), concussion injuries that are either acute or chronic, chronic and acute infections whether bacterial, fungal, parasitic, helminthic, prion, protozoan such as malaria or babesiosis, infections with spirochetes, and generalized sepsis. In addition, the miR assays can be useful to assess intra-uterine disorders during pregnancy, and pregnancy associated conditions such as pre-eclampsia and eclampsia. The measurements can be performed in all biological fluids: serum, plasma, urine, saliva, peritoneal fluid, cerebrospinal fluid, pericardial fluid, amniotic fluid, bile juice, pancreatic juice, tear fluid, maternal milk, galactorrhea fluid, lymph fluid, and liquid and solid stool. The methods can further include distinguishing between pancreatic ductal adenocarcinoma and chronic pancreatitis.

In certain aspects, the miR of interest can be miR-10b.

In certain aspects, the methods do not require labeling or amplification of the miR of interest.

The methods of diagnosing a disease state in a subject can further include any features, structures, chemicals, or reagents described herein.

Biosensor Arrays

This disclosure also provides a biosensor array.

The biosensor arrays can include a plurality of the biosensors as described herein. Two or more of the biosensors can have sensitivity to different miRs.

The biosensor assays can further include any features, structures, chemicals, or reagents described herein.

Figure 29:
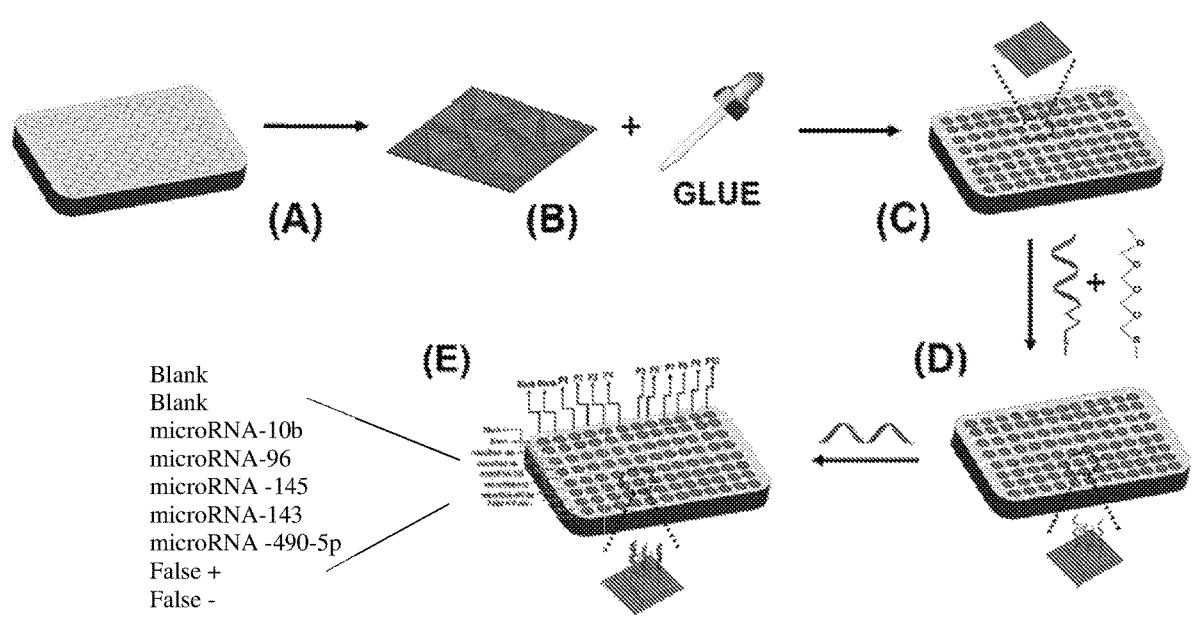
FIG. 29A-E is a scheme representing an illustrative example of a fabrication of multiplexing sensors for assaying numerous microRNAs using a 96 well plate, wherein (A) is a no-bottom 96 well plate, (B) is a chemically synthesized Au TNP functionalized glass coverslip, (C) is a 96 well plate with the functionalized glass coverslips glued to the bottom, (D) is a 96 well plate incubated in 1:1 ratio solution of -ss-DNA-3'-C3SH and PEG4-SH, and (E) is a 96 well plate incubated in different fully complimentary microRNA biomarkers and where patient samples would be incubated here.

FIGS. 29 and 37 provide illustrative examples of a biosensor array. A biosensor array allows for multiplexing. In some embodiments, the biosensor array comprises at least two biosensors with different target ss-DNA to test for more than one type of miR. In some embodiments, the biosensor array comprises compartments comprising a single biosensor type to test more than one patient sample. In some embodiments, the biosensor array comprises compartments with each row dedicated to a unique biosensor differentiated from the other biosensors based on its ss-DNA, and each column dedicated to a patient. In an illustrative embodiment, there could be about 10 rows of biosnesors, wherein each row comprises a unique type of biosensor, and there could be about 10 patient samples dedicated to a column, wherein each patient sample would be tested for the presence and quantity of 10 different biomarkers.

Kits

This disclosure also provides a kit.

Figure 36:
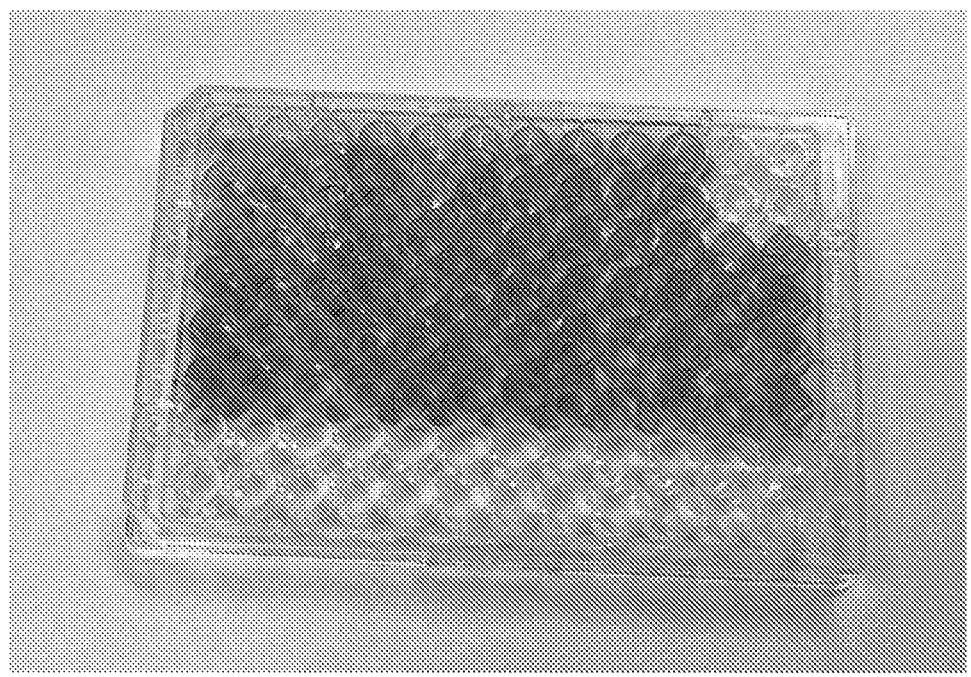
FIG. 36 is an image of a 96 well plate with biosensors in each well for multiplexing, wherein this is an illustrative example of a high throughput system.

The kit can include a biosensor comprising a substrate having a substrate surface to which a plurality of localized surface plasmon resonance (LSPR) antennae are affixed, the LSPR antennae affixed via an affixation surface of the LSPR antenna, the LSPR antennae comprising a functional surface opposite the affixation surface; and a plurality of ssDNA adapted to functionalize the functional surface. In certain aspects, the plurality of ssDNA can comprise a sequence that is the sequence of ssDNA-10b, ssDNA-21, ssDNA-96, ss-DNA-145, ssDNA-143, and ssDNA-490-5p, or a combination thereof. FIGS. 29 and 36 provide example illustrations of what the kit may look like.

In some embodiments, the kit comprises at least two biosensors. In some embodiments, the kit comprises a first biosensor comprising a substrate having a substrate surface to which a plurality of localized surface plasmon resonance (LSPR) antenna are affixed, the LSPR antenna affixed via an affixation surface of the LSPR antenna the LSPR antennae comprising a function surface opposite the affixation surface; and a plurality of a first ssDNA adapted to functionalize the functional surface; and a second biosensor comprising a substrate having a substrate surface to which a plurality of localized surface plasmon resonance (LSPR) antenna are affixed, the LSPR antenna affixed via an affixation surface of the LSPR antenna the LSPR antennae comprising a function surface opposite the affixation surface; and a plurality of a second ssDNA adapted to functionalize the functional surface. In some embodiments, the first biosensor comprises ssDNA-10b, ssDNA-21, ssDNA-96, ss-DNA-145, ssDNA-143, or ssDNA-490-5p, and the second biosensor comprises ssDNA-10b, ssDNA-21, ssDNA-96, ss-DNA-145, ssDNA-143, or ssDNA-490-5p. In some embodiments, the kit comprises at least three biosensors.

Figure 34:
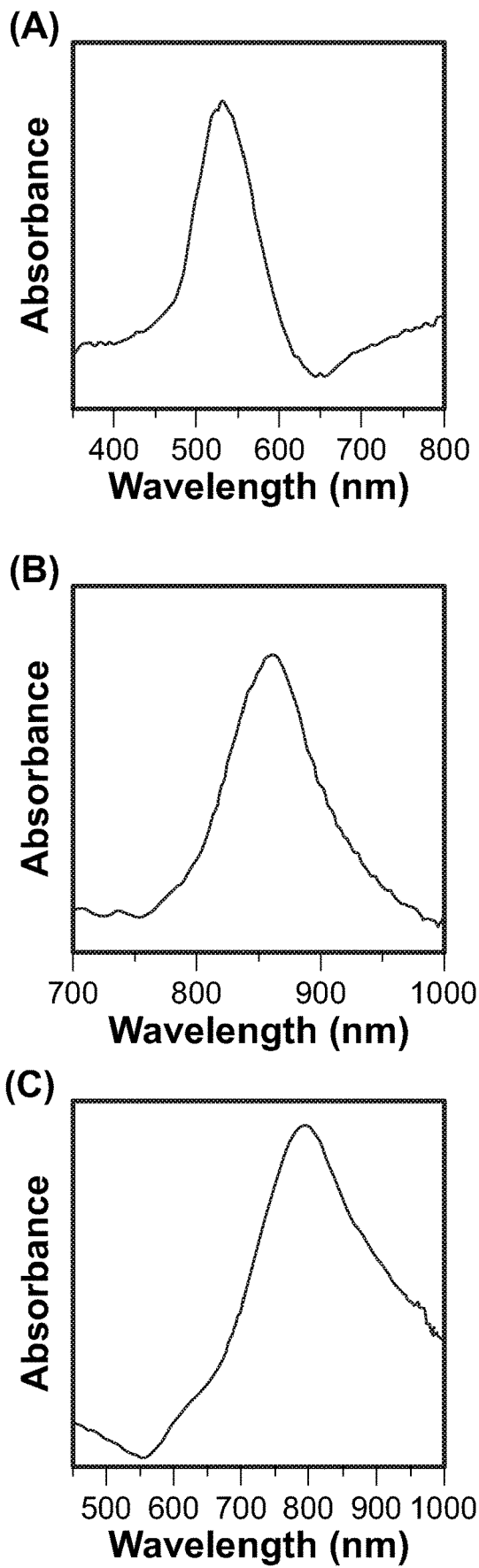
FIG. 34A-C are graphs showing UV-visible extinction spectra of (A) Au SNPs attached onto glass coverslip in air, (B) Au NRs attached onto glass coverslip in air, and (C) Au TNPs attached onto glass coverslip in air, and wherein Au SNPs- 530 nm, Au NRs- 860 nm, Au TNPs-795 nm. Spectra are normalized using Origin software.

The biosensors disclosed herein are very stable. The kit comprising the biosensors may be sealed without liquid surrounding the biosensors. See FIG. 34(A)-(C) demsonstrating the UV extinction spectra of the biosensors in air before any patient sample or control is added to the sensors. More specifically, 34 A shows UV-visible extinction spectra of Au SNPs attached onto glass coverslip in air, 34 B shows UV-visible extinction spectra of Au NRs attached onto glass coverslip in air, and 34 C shows UV-visible extinction spectra of Au TNPs attached onto glass coverslip in air (C). [Au SNPs- 530 nm, Au NRs- 860 nm, Au TNPs-795 nm]. Spectra were normalized using Origin software.

In certain aspects, the kit can include a plurality of spacer molecules adapted to functionalize the functional surface.

The kits can further include any features, structures, chemicals, or reagents described herein. In certain aspects, the kit comprises water.

Unless explicitly stated otherwise, all patents, patent applications, and non-patent literature cited herein is hereby incorporated by reference in its entirety. The present disclosure has been described in terms of one or more preferred aspects, and it should be appreciated that many equivalents, alternatives, variations, and modifications, aside from those expressly stated, are possible and within the scope of the disclosure.

EXAMPLES

Example 1

This disclosure describes for the first time the design and characterization of a regenerative, solid-state localized surface plasmon resonance (LSPR) sensor based on highly sensitive nanostructures (gold nanoprisms, which can be gold triangular nanoprisms) that obviates the need for labels or amplification of the miRs. A direct hybridization approach has enabled the detection of sub-femtomolar concentration of miR-X (X=21 and 10b) in human plasma from pancreatic cancer patients. LSPR-based measurements showed that the miR levels measured directly in patient plasma were at least two-fold higher than following RNA extraction and quantification by reverse transcriptase-polymerase chain reaction. Through LSPR-based measurements, nearly four-fold higher concentrations of miR-10b than miR-21 in plasma of pancreatic cancer patients were shown. This disclosure provides that the highly sensitive and selective detection approach for assaying miRs in plasma can be applied to many cancer types and disease states, and should allow a rational approach for testing the utility of miRs as markers for early disease diagnosis and prognosis, which could allow for the design of effective individualized therapeutic approaches.

This disclosure provides for the first time the fabrication of label-free, solid-state plasmonic biosensors for miR detection. The biosensing involves the direct hybridization of PDAC-relevant miRs in plasma to their complementary single-stranded DNAs (e.g., HS-C6-ssDNA) that were functionalized via S-linkages onto the surface of gold nanoprisms attached onto a glass substrate. The carbon chain attached to the ssDNA can be provided at different lengths, ranging, for example, between 3-and 6 carbons. This construct serves as a plasmonic biosensor through monitoring the LSPR dipole peak $\lambda_{LSPR}$). This disclosure also demonstrates that the sensors are extremely specific in miR detection and that addition of DNA-RNA duplex cleaving enzymes regenerates the sensor, allowing for multiple uses without compromising sensing efficiency.

Fabrication of the Plasmonic Biosensor for miRs Detection.

FIG. 1 represents the schematic diagram of a solid-state, label-free plasmonic biosensor fabrication for miR detection. Chemically synthesized gold nanoprisms (FIG. 1A), which displayed their $\lambda_{LSPR}$ at ~797 nm upon attachment to solid substrate immersed in PBS buffer, were selected as nanoantennas for biosensor fabrication because: (1) their $\lambda_{LSPR}$ peak position (in the 700-900 nm wavelength range) is particularly suitable for biomolecule detection because of negligible background scattering and adsorption of endogeneous chromophores from physiological media such as blood and plasma, (2) they have strong electromagnetic (EM) field enhancement at the sharp tips, (3) they exhibits a strong LSPR response to small changes in their surrounding environment, (4) their atomically smooth surface allows formation of a self-assembled monolayer (SAM) of receptors with both a tightly packed lower layer of alkylthiols and a more loosely packed upper layer that provide the required space for duplex formation with complementary miR strands, (5) gold is nontoxic and stable under extreme physiological conditions, and (6) the gold-sulfur bond is very stable with thiol-modified receptors making a strong covalent bond with the gold surface. Details describing the synthesis of gold nanoprisms and their attachment onto the silanized glass substrate are provided in a subsequent section herein. Above, the inventors have shown that a molecular sensor fabricated using a ~35 nm average edge-length gold nanoprisms displayed an unprecendentedly large 21 nm reversible shift upon a minor 0.6 nm increase in the thickness of the local dielectric environment. Therefore, gold nanoprisms of this size and geometry are unique and should provide high sensitivity if plasmonic biosensors are fabricated using them, which is in the scope of this disclosure. This disclosure provides the first example of LSPR-based miRs sensing in physiological media.

For detection and quantification, the selected targets were miR-21 and miR-10b, because it has been shown by locked nuclei acid-based in-situ hybridization that they are overexpressed in pancreatic cells (PCCs) within the tumor mass and that circulating miR-10b may serve as biomarker for diagnosis of PDAC. The sensing strategy was designed based on the hybridization between complementary probes (-C6-ssDNA-X, X=21 and 10b) attached to gold nanoprisms and their target miRs. The introduction of spacers in-between the DNA probes was included to reduce steric hindrance between the probes and the miRs and therefore enhance the hybridization and ultimately the sensitivity. As shown in FIG. 1B, poly (ethylene glycol)$_6$-thiols (PEG$_6$-SH) were used as spacers because they avoid non-specific adsorption of extraneous materials onto the nanoprism's surface and are not reactive towards miRs or other biological constituents present in plasma. Previously, the inventors demonstrated that functionalization of a nanoantenna's surface with an equal mole ratio of receptor and spacer provided the best sensitivity and lowest limit of detection (LOD). Therefore, a 1:1 ratio of HS-C6-ssDNA-X:PEG$_6$-SH was used to prepare the plasmonic biosensors (FIG. 1B). All the miRs and oligonucleotides sequences used in these studies are provided in Table 1.

UV-vis spectroscopy was used to monitor the changes in $\lambda_{LSPR}$ of the gold nanoprisms at different functionalization steps. The functionalization of substrate-bound nanoprisms with 1:1 ratio of HS-C6-ssDNA-21:PEG$_6$-SH resulted in an ~20.5±3.2 nm red-shift of $\lambda_{LSPR}$ as a result of the increase in local refractive index, which suggested the attachment of both molecular species onto the nanoprism's surface. These plasmonic biosensors were utilized for miR detection by incubating miR-21 (obtained from Sigma-Aldrich, USA) with concentration ranging from 100 nM to 50 fM in PBS buffer, 40% bovine plasma, or 40% human plasma solution. The $\lambda_{LSPR}$ response of gold nanoprisms for each miR-21 concentration was measured where the highest 18.8±1.9 nm $\lambda_{LSPR}$ red shift was observed for 100 nM miR-21 in PBS buffer. It is hypothesized that the $\lambda_{LSPR}$ red-shift is due to hybridization between ssDNA-21 and miR-21. It was found that the magnitude of the $\lambda_{LSPR}$ shift was concentration dependent, where 50 fM miR-21 caused a 3.7±0.3 nm $\lambda_{LSPR}$ red shift in PBS buffer. Table 2-4 summarizes the $\lambda_{LSPR}$ position for each concentration for the three different media. Evidently higher concentrations of miR-21 induced a larger number of ssDNA-21 strands to convert to DNA: RNA duplexes and consequently a larger change in the local refractive index around the nanoprisms, which results in a larger value of $\Delta\lambda_{LSPR}$.

The sensing mechanism is based on the hypothesis that the attachment of complementary target miRs to the plasmonic biosensor will shift the $\lambda_{LSPR}$ to higher wavelength (FIG. 1C). The total shift ($\Delta\lambda_{LSPR}$) depended on the miR concentration (FIG. 1D) and could be used to determine the limit of detection (LOD) (FIG. 1E). The LODs calculated for miR-21 in three different media were found to be in the range of 23-35 fM, which was more than 1000 and 3 fold lower than with the label-free microring resonator (150 fmol) and the nanopore based (100 fM) miR sensors, respectively. Importantly, these techniques detected miRs in PBS buffer whereas this disclosure provides for the first time a sensing approach in physiological media. Utilizing a direct hybridization-based detection approach, plasmonic biosensors were constructed comprising -C6-ssDNA-10b, while keeping other parameters constant. The LOD for miR-10b in the above media was determined over a concentration range from 100 nM to 50 fM. The average $\Delta\lambda_{LSPR}$ and LODs for miR-10b in three diverse media are shown in Tables 5-7, and 9-10.

The principle underlying the actions of plasmonic biosensors is based on the successful hybridization between miRs and ssDNA attached to nanoprisms, where a higher number of duplex formations will result in a larger change in the refractive index surrounding the nanoprisms resulting in larger $\Delta\lambda_{LSPR}$ and higher sensitivity. Therefore, it would be expected that functionalization of gold nanoprisms with 100 percent HS-C6-ssDNA-X (without the $PEG_6$-thiol spacer) should reduce the LOD values because of steric hindrance and low attachment of miRs. To investigate this, gold nanoprisms were functionalized with 100 percent -C6-ssDNA-21 resulting in an -15.0±1.8 nm $\lambda_{LSPR}$ red shift. The sensor was then incubated in different concentrations of miR-21 prepared in 40% human plasma. A-9.6±1.1 nm red shift was observed for a 100 nM miR-21 concentrations and the lowest concentration that can be repeatedly detected was 10 µM from a $\Delta\lambda_{LSPR}$ of 3.4±0.5 nm. Table 8 contains the $\Delta\lambda_{LSPR}$ versus concentration data. Evidently, functionalization of the nanoprism's surface with 100 percent -C6-ssDNA-21 resulted in a 200-fold increase in detection limit in comparison to the 1:1 ratio -C6-ssDNA-21:PEG6-SH mixed functionalization (Table 8). These experimental data further highlight the rationale for using spacers that increase the likelihood of hybridization. Fully covered gold nanoprisms were believed to be obtained when 100 percent -C6-ssDNA-21 was used for functionalization, which creates steric hindrance and does not allow the maximum number of miR-21 strands to come into close proximity with -C6-ssDNA-21 for hybridization. Therefore, not all the -C6-ssDNA-21 attached on the gold nanoprisms' surface was hybridized with miR-21 strands resulting in low sensing response. Thus, if a spacer was introduced between the -C6-ssDNA-21, it could allow the maximum -ssDNA-21 strands to be freely available for hybridization without any interference and ultimately enhance the sensitivity of the biosensor. Accordingly, a 1:1 mixed -C6-ssDNA-X:$PEG_6$-SH was used to functionalize the gold nanoprisms for the data collected herein, though it should be appreciated that different ratios can be suitable.

In order to confirm the hybridization of miR-X with -C6-ssDNA-X that resulted in the $\Delta\lambda_{LSPR}$, the enzyme RNase H was used to selectively cleave the DNA: RNA duplex and potentially reverse the $\Delta\lambda_{LSPR}$. Initially, the plasmonic biosensor for miR-21 was incubated in a 100 nM solution of miR-21, which resulted in red-shift of $\lambda_{LSPR}$ potentially reflecting hybridization. The biosensor was then immersed in 15 units of RNase H solution for 2 h. Afterwards the $\lambda_{LSPR}$ showed a blue shift and reverted back to its original position before miR-21 incubation. When the 1:1 ratio -C6-ssDNA-21:$PEG_6$-SH mixed functionalized biosensor was incubated with RNase H solution alone overnight, no noticeable change in $\lambda_{LSPR}$ value was observed. These experimental results validate the previous observation that the $\lambda_{LSPR}$ blue shift was due to the cleavage of heteroduplex done by RNase H. The biosensors were rinsed with RNase free water and again incubated in 100 nM miR-21 solution for rehybridization where a-14 nm red shift of the $\lambda_{LSPR}$ was observed. These experiments confirm the working hypothesis that hybridization between the nanoprism's surface ligands (-C6-ssDNA-X) and the miR-X resulted in changes in the local dielectric environment around the nanoprisms causing wavelength shift. The $\lambda_{LSPR}$ responses were identical for several cycles due to hybridization and dehybridization of miR-21 over a period of 6 days. The LSPR peak shifts back and forth upon sensor regeneration with RNase H by cleaving DNA:RNA duplex and rehybridization after incubation into 100 nM miR-21 in 40% human plasma. After each dehybridization steps the plasmonic biosensors were thoroughly rinsed with PBS buffer to completely remove enzyme RNase H. The same experiments were done for the miR-10b biosensor and similar results were observed, underscoring the long-term stability of the sensors and their potential for being developed into cost-effective point of care diagnostic tools. See FIG. 2 and FIG. 32 graphs showing the ability to regenerate the biosensor after hybriding to a miR of interest.

The hybridization takes place at the 5' end of -C6-ssDNA-21 and the 3' end of miR-21, which evidently increased the refractive index. Additionally such hybridization would also increase the thickness of the local dielectric environment of the nanoprisms. Together, a significantly large $\Delta\lambda_{LSPR}$ was generated for both miR-21 and miR-10b. Atomic force microscopy (AFM) analysis was conducted to characterize the plasmonic biosensors and also to verify the change in surface area caused by miR-21 incubation with mixed -C6-ssDNA-21 and $PEG_6$-SH-functioanlized gold nanoprisms. After analyzing 40 different nanoprisms an average $2.4\times10^{-15}$ m$^2$ increase in surface area was observed. Thus, attachment of miRs to plasmonic biosensors has increased the thickness of local dielectric environment around the gold nanoprisms and influenced their LSPR properties. Ultrasensitive refractive index-induced LSPR response of nanoprisms allows us to fabricate label-free plasmonic biosensor.

The successful implementation of plasmonic biosensors with real biological samples mandates documentation of their specificity towards target miRs since patient samples contain multiple miR species. The mixed functionalized (-C6-ssDNA-21 and $PEG_6$-SH) biosensors were incubated overnight in 40% human plasma solution containing 100 nM each miR-16, miR-122, miR-126, and miR-141, because these miRs are commonly present in human plasma. The $\lambda_{LSPR}$ response was measured before and after incubation and resulted in an -2.5±0.3 nm $\lambda_{LSPR}$ red shift, which is within the instrument noise level and/or minor non-specific adsorption of extraneous materials present in human plasma. In another control experiment, gold nanoprisms attached as before to glass substrate were functionalized with 100% $PEG_6$-SH by incubating in 1 µM aqueous solution of the ligand, and after rinsing with large amounts of water, incubated in a 40% human plasma solution of 100 nM miR-21 for 12 h. This procedure resulted in only an ~0.9±0.7 nm $\lambda_{LSPR}$ red shift, confirming that the plasmonic biosensors disclosed herein are highly specific towards the target miRs. Detection of miR Levels in Plasma from Pancreatic Cancer Patients.

Pancreatic cancer is the fourth-leading cause of cancer death in the United States with an annual mortality of nearly 40,000 and a dismal five-year survival rate of 6%. PDAC is characterized by chemotherapeutic resistance and by the absence of an effective screening procedure for early disease. It is generally accepted that early diagnosis could reduce mortality rates substantially and thus a non-invasive early PDAC test must be developed. Several miRs (such as miR-21, -10b, -103, -155, -196a, 210, and -221) were found to be overexpressed in PDAC. Given their resistance to degradation, plasma miRs have the potential to serve as biomarkers for the non-invasive diagnosis of PDAC. Previously, nanopore sensors were used to detect miRs in lung cancer patients, but to the best of the inventors' knowledge no sensors have been developed to date to detect PDAC-related miRs in human plasma.

Utilizing the plasmonic biosensors miR-21 and miR-10b were detected in plasma from PDAC patients. Plasma samples were collected from six patients and six normal control subjects. Total plasma RNAs including miRs were extracted from 100 µL of each plasma sample using a TRIZOL® kit (available commercially from Life Technologies, Carlsbad, CA), with a final elution volume of 28 µL. Next, 14 µL volumes were used for miR quantification by the plasmonic biosensor and the remaining 14 µL were used in the qRT-PCR assay. The plasmonic biosensors were fabricated as described before for both miR-21 and miR-10b detection. The extracted human miR-21 or miR-10b samples were diluted in PBS buffer and incubated with the biosensors for 12h, followed by rinsing with PBS buffer and measurement of the $\lambda_{LSPR}$ response in PBS buffer. The observed $\lambda_{LSPR}$ shift for each miR-21 and miR-10b sample was converted into the corresponding concentration using the calibration curve derived for miR-21 or 10b under optimized conditions and compared with the value from normal human patients (Tables 11-14). The concentrations of miR-21 and miR-10b determined from plasmonic biosensors were also compared with the values obtained from the qRT-PCR assay (Tables 15-18). Importantly, for the first time, through a label-free technique this disclosure has shown that miR-10b concentration is nearly four-fold higher than the miR-21 level in patient samples. Inasmuch as both mirR-21 and miR-10b are overexpressed in PDAC, it is possible that miR-10b is released more efficiently by pancreatic cancer cells than miR-21, allowing it to achieve higher levels in the circulation. It is therefore possible that miR-10b levels are also increased within the pancreatic tumor microenvironment, where it could be acting to enhance PDAC biological aggressiveness.

miR-21 levels were also detected directly in human plasma samples collected from PDAC patients without RNA extraction. Thus, 50 µL human plasma samples were obtained from the six-pancreatic cancer patients and diluted in PBS buffer followed by incubation with the plasmonic biosensors for 12 h. The $\lambda_{LSPR}$ response of each sample was measured through UV-vis spectroscopy and showed a steady increase in concentration from sample 6 to 1 (Table 19-20). Both plasmonic biosensor and qRT-PCR results indicated that miR-10b levels were higher in PDAC patients compared to normal human and that the levels of miR-21 and miR-10b can be quantified with high accuracy using the gold nanoprisms-based plasmonic biosensor without any modification, amplification, or labeling. Importantly, the miR-21 concentration in extracted samples was at least two-fold lower than in the pure plasma samples. It is believed that this is due to degradation and/or loss of miRs during the RNA extraction processes. Therefore, most widely used qRT-PCR method to determine the concentration of miRs in patients may not accurately represent the actual concentration. This limitation and imprecise quantification can be avoided by using the newly developed plasmonic biosensors, which provide a unique opportunity as potential diagnostic and prognostic markers in PDACs and other cancers.

CONCLUSION

A plasmonic biosensor that was able to detect PDAC relevant miRs in human plasma without using RNAs extraction was designed, fabricated, and characterized, which opens a new avenue for the direct detection and quantification of miR levels in clinical samples without any form of sample preparation. To the inventors' knowledge, this is the first LSPR-based, label-free, direct hybridization method for miR detection, which eliminates all the current drawbacks such as labeling, tagging, amplification, use of highly toxic chemicals, and further modification of the sensor. Furthermore, it vastly simplifies the detection approach without requiring detailed knowledge of the electron or energy transfer processes involved as in other more complicated techniques. Additionally, this ultrasensitive, plasmonic-based, direct hybridization-controlled detection approach is applicable to any type of miRs that are relevant to various diseases. It was found that the plasmonic biosensor can be regenerated through several cycles and is stable for several days without compromising its sensitivity and selectivity, which should enable the development of simple, cost-effective tools for the early detection of miRs and thus facilitate the early diagnosis of various cancers. Finally, the large EM-field enhancement at the nanoprism's sharp tips may enhance the Raman scattering intensity of the analytes. Therefore, nanoprisms can be developed for use as an effective substrate for surface-enhanced Raman spectroscopy-based detection and quantification of multiple miRs simultaneously through integration of their spectral characteristic with the $\lambda_{LSPR}$ shifts.

Materials and Methods

All synthetic DNA probes and miRs were purchased from Sigma-Aldrich (USA). PBS buffer prepared with RNase-free water was used to dilute oligonucleotides and miRs solutions. Patient plasma was obtained from the Indiana University Simon Cancer Center Solid Tissue Bank (Indianapolis, Indiana).

Fabrication of LSPR-Based miR Sensors and Detection.

The gold nanoprism-based miR sensors were designed using a published procedure (set forth in Joshi, G. K. et al. Ultrasensitive Photorevsersible Molecular Sensors of Azobenzene Functionalized Plasnomic Nanoantennas. Nano Letters 14, 532-540 (2014) and incorporated herein by reference in its entirety) with modification. The attachment of gold nanoprisms on silanized glass substrates is described below. The substrate-bound nanoprisms were incubated in PBS buffer solution containing 1 µM each of HS-C6-ssDNA-X and $PEG_6$-SH overnight and rinsed with PBS buffer. The initial LSPR peak position of each sensing platform was determined using UV-visible spectroscopy in PBS buffer and then was incubated in the different concentrations of miR solutions, e.g., either in PBS buffer, 40% bovine plasma, or 40% human plasma for 12h at room temperature. The plasmonic biosensors were thoroughly washed with PBS buffer to remove any non-specifically adsorbed species. The miR bound biosensor was then placed in PBS buffer for 10 min before the LSPR peak position was determined. For UV-vis extinction spectra measurement, one particular solvent was chosen to avoid the solvent dielectric constant effect, which is known to shift the LSPR peak.

Total RNA Extraction and Quantification of miR by qRT-PCR.

Total RNA was isolated from plasma samples that were obtained from the Indiana University Simon Cancer Center Solid Tissue Bank (Indianapolis, IN, USA) using Trizol® LS reagent (Life Technologies, Carlsbad, CA, USA). cDNA was generated using 10 ng of RNA and miR-10b, miR-21, or miR-425-5p RT primers and a miR reverse transcription kit (Life Technologies) as per the manufacturer's recommendations. Quantitative PCR (qPCR) was performed using Taqman® miR expression assay reagents. Expression levels as determined by qPCR were normalized to miR-425-5p, since this miR was expressed at similar levels in all samples and exhibited <1 cycle threshold (Ct) difference across all samples. After normalization to miR-425-5p (ΔCt), the ΔCt values for miRs in controls were averaged and subtracted from the ΔCt values of each individual sample (ΔΔCt). miR levels were then calculated using the $2^{-\Delta\Delta Ct}$ method, as described in Livak, K. J. & Schmittgen, T. D. Analysis of Relative Gene Expression Data Using Real-Time Quantitative PCT and the 2-ΔΔCT Method. Methods. 25, 402-408 (2001) and incorporated by reference herein by reference in its entirety.

buffer solution. Polyethylene glycol thiol ($PEG_6$-SH) was synthesized in the laboratory using published procedures set forth in Lawrence, K. N.; Johnson, M. A.; Dolai, S.; Kumbhar, A.; Sardar, R. Solvent-like ligand-coated ultrasmall cadmium selenide nanocrystals: strong electronic coupling in a self-organized assembly. *Nanoscale* 2015, 7, 11667-11677 and incorporated herein by reference in its entirety.

Nucleic Acid Sequences

In this example, the following oligonuclotide and miR strands were used: ssDNA-21 (SEQ ID NO: 1); ssDNA-10b (SEQ ID NO: 2); target miR-21 (SEQ ID NO: 3); target miR-10b (SEQ ID NO: 4); miR-16 (SEQ ID NO: 5); miR-126 (SEQ ID NO: 6); miR-141 (SEQ ID NO: 7); and miR-122 (SEQ ID NO: 8).

TABLE 1

Summary of oligonucleotide and miR strands used in this Example.

| strand | name | sequence | MW (kDa) | modification |
| --- | --- | --- | --- | --- |
| A | SSDNA-21 | 5'-TCAACATCAGTCTGATAAGCTA-3' | 6.7 | 5'thiol-$C_6$ |
| B | ssDNA-10b | 5'-CACAAATTCGGTTCTACAGGGTA-3' | 7.1 | 5'thiol-$C_6$ |
| C | target miR-21 | 5'-UAGCUUAUCAGACUGAUGUUGA-3' | 6.6 | none |
| D | target miR-10b | 5'-UACCCUGUAGAACCGAAUUUGUG-3' | 7.0 | none |
| E | miR-16 | 5'-UAGCAGCACGUAAAUAUUGGCG-3' | 7.1 | none |
| F | miR-126 | 5'-CAUUAUUACUUUUGGUACGCG-3' | 6.3 | none |
| G | miR-141 | 5'-UAACACUGUCUGGUAAAGAUGG-3' | 6.7 | none |
| H | miR-122 | 5'-UGGAGUGUGACAAUGGUGUUUG-3' | 6.8 | none |

Chemicals.

Chloro(triethylphosphine) gold (I) ($Et_3PAuCl$, 97%), poly(methylhydrosiloxane) (PMHS, Mn=1700-3300), trioctylamine (TOA, 98%), ACS grade acetonitrile ($CH_3CN$, 99.9%), methanol (99.8%), human plasma (contains 4% trisodium citrate and tested for HIV, hepatitis C and hepatitis B), thiol modified ssDNAs, miRs (miRs), Tris-base, magnesium chloride ($MgCl_2$), potassium chloride (KCl), ethylenediaminetetraaceticacid (EDTA), and bovine plasma (contain 3.8% trisodium citrate as an anticoagulant) were purchased from Sigma Aldrich and were used as received. (3-mercaptopropyl)-triethoxysilane (MPTES, 94%) was purchased from Alfa Aesar, and ethanol (alcohol 200 proof) was purchased from Decon labs. RNase H enzyme and RNase H reaction buffer were purchased from New England BioLabs Inc. RNase free sterile water was obtained from Baxter Healthcare Corporation. 1, 4-Dithiothreitol (DTT) was purchased from Roche Diagnostics. Hydrochloric acid (HCl), sodium chloride (NaCl, ≥99.5%), sodium phosphate monobasic monohydrate ($NaH_2PO_4 \cdot H_2O$, >98%), sodium phosphate dibasic anhydrous ($Na_2HPO_4$), and the glass coverslips were purchased from Fisher Scientific. RBS 35 Detergent was obtained from Thermo Scientific and used as received. The super Sharpe silicon scanning probes (SSS-NCHR) for atomic force microscopy measurements were purchased from nanosensors. All water was purified using a Thermo Scientific Barnstead™ Nanopure™ system. Thiol modified oligonucleotides and all miRs were stored at −20° C. RNase free sterile water was used to prepare the PBS Spectroscopy and Microscopy Characterization.

Absorption and extinction spectra in the range of 300-1100 nm were collected with a Varian Cary® 50 Scan UV-visible spectrophotometer using 1 cm quartz cuvette. All the absorbance spectra were collected using 0.3 mL of reaction solution diluted in 2.0 mL of acetonitrile. Acetonitrile was used as a background for these measurements, and the background was run before collecting the absorbance spectra. All extinction spectra were measured in PBS buffer (pH 7.2) at room temperature unless otherwise specified. Here, the blank silanized glass coverslips immersed in PBS buffer were used as a background and the background was run before collecting the extinction spectra. The chemically synthesized gold nanoprisms attached onto the silanized glass coverslips were characterized after each functionalization step through atomic force microscopy (AFM). All AFM measurements were conducted in air utilizing tapping mode on a Bruker BioScope Catalyst with SSS-NCHR probes (Nanosensors) (tip radius ~2 nm). Images were collected using a tip velocity of 1 mM/s over 1-2 uM scan sizes of three to five regions of each samples. All microscopy files were plain fitted and 2D fitted using Gwyddion. Also using the software, the individual nanoprisms were selected and analyzed to determine their surface area and height profiles.

Synthesis of Gold Nanoprisms.

Gold nanoprisms were chemically synthesized according to a previously developed procedure with minor modification. Specifically, $Et_3PAu(I)Cl$ (8 mg, 0.02 mmol) was dissolved in 5 mL of acetonitrile and allowed to stir for 5 min at room temperature. 0.085 mL of TOA and 0.3 mL of PMHS were mixed with 1 mL of acetonitrile in a vial and injected into the above solution. The reaction mixture was then allowed to heat at 40° C. The solution color started to change from colorless to pink, purple, blue and at this point 14 mL acetonitrile was added to the reaction and the reaction was allowed to run for another 130 min, which resulted in a dark blue solution indicating the formation of nanoprisms with a stable absorbance dipole peak at 780 nm in acetonitrile. The solution was then removed from heat, centrifuged at 7000 rpm for 2 minutes, and used for the biosensor fabrication.

Silanization of Glass Coverslips and Attachment of Nanoprisms.

The glass coverslips (supporting substrates) were functionalized according to previously published procedures. Glass coverslips were immersed in a 20% (v/v) aqueous RBS 35 detergent solution at 90° C. for 30 min, followed by 5 min of sonication. After thoroughly rinsing the coverslips with nanopure water, they were placed in a solution of conc. hydrochloric acid and methanol (1:1 v/v) for 30 min. The coverslips were then rinsed several times with nanopure water and dried in a vacuum oven at 60° C. overnight then incubated in a solution of 10% MPTES in ethanol for 30 min, sonicated for 5 min, and rinsed with anhydrous ethanol. The coverslips were rinsed with ethanol by sonicating them in ethanol, which was repeated at least 5 times. After rinsing, the coverslips were baked in a vacuum oven at 120° C. for 3 hours. The MPTES-functionalized coverslips (substrate) were then incubated for 30 min in a freshly prepared gold nanoprisms reaction solution. After incubation, the substrate-bound gold nanoprisms were rinsed with ethanol, dried under nitrogen flow, and stored under nitrogen at 4° C.

Preparation of miR Sensors.

As the reaction solution contains other non-prismatic nanostructures, a tape-cleaning procedure was performed on the substrate bound gold nanoprisms platform to remove non-prismatic nanostructures. Tape cleaning was done by placing the adhesive (scotch) tape onto the gold nanoprisms attached supporting substrate, gently pressed down with a finger, and slowly removed at a 900 angle. The nanoprisms containing supporting substrates were then incubated into PBS buffer solution containing HS-C6-ssDNA-X: $PEG_6$-SH (1 µM each) for overnight. Next, the HS-C6-ssDNA-X: $PEG_6$-SH functionalized gold nanoprisms (plasmonic biosensor for miR-X) were rinsed with copious amount of PBS buffer to remove loosely bound reactants and biosensors then further utilized for miR-X sensing.

Detection of Synthetic miRs in Either PBS (pH=7.4) buffer, 40% Bovine Plasma, and 40% Human Plasma.

Different concentrations of synthetic miR-X solutions were prepared either in PBS buffer, or 40% bovine plasma, or 40% human plasma. The plasmonic biosensors prepared in above were then incubated in the different concentrations of miR-X solutions in above-mentioned physiological media overnight. The miR-X bound biosensors were then rinsed with PBS buffer to remove any non-specifically adsorbed species and placed in PBS buffer for 10 min to equilibrate. Extinction spectra were collected in PBS buffer.

Confirming DNA-RNA Duplex and Regeneration of the Sensors.

In order to confirm the miR-X hybridization with the plasmonic biosensor, hybridized, dehybridized, and rehybridized with target miR-X were investigated. RNase H enzyme that selectively cleaves the DNA: RNA duplex was used for dehybridization studies. The plasmonic biosensor for miR-21 was allowed to hybridize in 100 nM of miR-21 in 40% human plasma overnight. The plasmonic biosensor's response ($\lambda_{LSPR}$) was measured before and after the incubation in miR-21. To confirm that the $\lambda_{LSPR}$ shift observed after miR-21 incubation was indeed due to its hybridization with the gold nanoprisms' surface bound HS-$C_6$-ssDNA-21 probe, the miR-21 bound plasmonic biosensor was immersed in 15 units of RNase H suspended 20 mM of Tris-HCl (pH 7.4), 20 mM KCl, 10 mM $MgCl_2$, 0.1 mM EDTA, and 0.1 mM DTT solution for 2h, then rinsed with PBS buffer and the $\lambda_{LSPR}$ shift was measured. The plasmonic biosensor was further incubated in 100 nM miR-21 solutions of 40% human plasma overnight. The same process was repeated for several cycles to confirm the stability and the regeneration of the plasmonic biosensor. See FIGS. 2 and 32. Control experiments without hybridized miR-21 were also performed, where the plasmonic biosensor for miR-21 was immersed in RNase H containing reaction solution for overnight followed by rinsing with PBS buffer. The biosensor was further immersed in 100 nM miR-21 solutions in 40% human plasma overnight, rinsed with PBS buffer and the $\Delta\lambda_{LSPR}$ shift was measured.

miR Detection of Total RNAs Extracted and Purified Pancreatic Cancer Patients Plasma in PBS Buffer.

The plasma samples were collected from six PDAC patients and six normal human samples. Total plasma RNAs including miRs were extracted from 100 µL of each plasma sample using TRIZOL® kit, with a final elution volume of 28 µL. 14 µL volumes were used for the miR quantification using the plasmonic biosensor and the remaining 14 µL were used for qRT-PCR assay to confirms the miR levels in each sample. 14 µL volumes were diluted in 786 µL of PBS buffer and the prepared plasmonic biosensor for miR-X was incubated in that solution overnight, followed by rinsing with PBS buffer and $\lambda_{LSPR}$ measurements in PBS buffer.

miR Detection in Human Plasma Collected from Pancreatic Cancer Patients without RNAs Extraction.

50 µL of human plasma samples were obtained from the six PDAC patients. 50 µL of aliquot was diluted with 750 µL of PBS buffer and the plasmonic biosensor prepared for miR-21 was immobilized in these solutions overnight and then rinsed with PBS buffer. $\lambda_{LSPR}$ responses of the biosensor for each plasma sample were measured in PBS buffer. The experiment was repeated at least four times and the obtained $\lambda_{LSPR}$ responses were further correlated with the results obtained for same samples through qRT-PCR assay.

Data Processing and Statistical Analysis.

All measurements for synthetic miRs were repeated at least five times, and the PDAC patients' samples were measured at least four times. The obtained responses were reported as mean±S.D. for each step. The $\lambda_{LSPR}$ peak position was determined by taking the maxima of the dipole peak position in the UV-visible spectra. The $\Delta\lambda_{LSPR}$ was derived by taking the difference between the plasmonic biosensors response towards the $\lambda_{LSPR}$ before and after hybridization with the standard target miR-X to the functionalized surface ssDNA-X probe. All UV-visible spectra and the calibration curves were plotted using the MS-Excel. The extinction spectra were adjusted to the highest extinction value to visualize the $\lambda_{LSPR}$ shift. The LOD was calculated by measuring the $\Delta\lambda_{LSPR}$ for the blank and then obtained the Z (mean+3σ) value and convert the Z value into the relative concentration using the calibration curve. Here, the blank measurement was the $\lambda_{LSPR}$ response for HS-C6-ssDNA-X: $PEG_6$-SH functionalized gold nanoprisms before and after overnight incubation in the relative physical media without target miR-X. The relative concentration for miR-X for total RNAs extracted from PDAC patient plasma and normal human plasma samples were derived from the calibration curve obtained for synthetic miR-X in PBS buffer. However, the calibration curve for synthetic miR-21 in 40% human plasma was used to derive the relative concentrations for miR-21 in PDAC patients' plasma without any extraction.

Experimental Data to Develop Calibration Curves

TABLE 2

$\lambda_{LSPR}$ responses from plasmonic biosensor exposed to different concentrations of miR-21 in PBS buffer.

| Sensor # | $\lambda_{LSPR}$ (nm) for HS-C6-ssDNA-21: PEG$_6$SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| 100 nM | | | | | |
| 1 | 818 | 838 | 20.0 | | |
| 2 | 817 | 833 | 16.0 | | |
| 3 | 819 | 838 | 19.0 | 18.8 | 1.9 |
| 4 | 821 | 839 | 18.0 | | |
| 5 | 820 | 841 | 21.0 | | |
| 10 nM | | | | | |
| 1 | 814 | 830 | 16.0 | | |
| 2 | 819 | 832 | 13.0 | | |
| 3 | 818 | 834 | 16.0 | 13.6 | 2.5 |
| 4 | 815 | 828 | 13.0 | | |
| 5 | 817 | 827 | 10.0 | | |
| 1 nM | | | | | |
| 1 | 819 | 831 | 12.0 | | |
| 2 | 816 | 826 | 10.0 | | |
| 3 | 821 | 833 | 12.0 | 11.8 | 1.1 |
| 4 | 816 | 829 | 13.0 | | |
| 5 | 818 | 830 | 12.0 | | |
| 0.1 nM | | | | | |
| 1 | 816 | 825 | 9.0 | | |
| 2 | 820 | 829 | 9.0 | | |
| 3 | 815 | 823 | 8.0 | 8.8 | 0.8 |
| 4 | 818 | 828 | 10.0 | | |
| 5 | 819 | 827 | 8.0 | | |
| 0.01 nM | | | | | |
| 1 | 817 | 827 | 10.0 | | |
| 2 | 818 | 826 | 8.0 | | |
| 3 | 820 | 828 | 8.0 | 8.4 | 1.1 |
| 4 | 819 | 828 | 9.0 | | |
| 5 | 818 | 825 | 7.0 | | |
| 0.001 nM | | | | | |
| 1 | 820 | 826 | 6.0 | | |
| 2 | 819 | 825 | 6.0 | | |
| 3 | 815 | 822 | 7.0 | 6.2 | 0.8 |
| 4 | 815 | 820 | 5.0 | | |
| 5 | 817 | 824 | 7.0 | | |
| 0.0001 nM | | | | | |
| 1 | 818 | 823 | 5.0 | | |
| 2 | 817 | 822 | 5.0 | | |
| 3 | 820 | 824 | 4.0 | 4.8 | 0.4 |
| 4 | 819 | 824 | 5.0 | | |
| 5 | 818 | 823 | 5.0 | | |
| 0.00005 nM | | | | | |
| 1 | 816 | 819.7 | 3.7 | | |
| 2 | 820 | 824 | 4.0 | | |
| 3 | 821 | 824.5 | 3.5 | 3.7 | 0.3 |
| 4 | 815 | 819 | 4.0 | | |
| 5 | 817 | 820.4 | 3.4 | | |

TABLE 3

$\lambda_{LSPR}$ responses from plasmonic biosensor exposed to different concentrations of miR-21 in 40% human plasma.

| Sensor # | $\lambda_{LSPR}$ (nm) for HS-C6-ssDNA-21: PEG$_6$SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| 100 nM | | | | | |
| 1 | 823 | 836 | 13.0 | | |
| 2 | 816 | 828 | 12.0 | | |
| 3 | 820 | 832 | 12.0 | 12.6 | 0.9 |
| 4 | 815 | 829 | 14.0 | | |
| 5 | 822 | 834 | 12.0 | | |
| 10 nM | | | | | |
| 1 | 817 | 828 | 11.0 | | |
| 2 | 815 | 825 | 10.0 | | |
| 3 | 814 | 824 | 10.0 | 10.0 | 0.7 |
| 4 | 818 | 827 | 9.0 | | |
| 5 | 815 | 825 | 10.0 | | |
| 1 nM | | | | | |
| 1 | 815 | 824 | 9.0 | | |
| 2 | 816 | 824 | 8.0 | | |
| 3 | 815 | 823 | 8.0 | 8.4 | 0.5 |
| 4 | 814 | 823 | 9.0 | | |
| 5 | 813 | 821 | 8.0 | | |
| 0.1 nM | | | | | |
| 1 | 815 | 822 | 7.0 | | |
| 2 | 817 | 825 | 8.0 | | |
| 3 | 814 | 821 | 7.0 | 7.6 | 0.5 |
| 4 | 813 | 821 | 8.0 | | |
| 5 | 815 | 823 | 8.0 | | |
| 0.01 nM | | | | | |
| 1 | 816 | 822 | 6.0 | | |
| 2 | 814 | 821 | 7.0 | | |
| 3 | 815 | 821 | 6.0 | 6.6 | 0.5 |
| 4 | 814 | 821 | 7.0 | | |
| 5 | 813 | 820 | 7.0 | | |
| 0.001 nM | | | | | |
| 1 | 815 | 821 | 6.0 | | |
| 2 | 816 | 822 | 6.0 | | |
| 3 | 815 | 820 | 5.0 | 5.2 | 0.8 |
| 4 | 815 | 820 | 5.0 | | |
| 5 | 814 | 818 | 4.0 | | |
| 0.0001 nM | | | | | |
| 1 | 816 | 821 | 5.0 | | |
| 2 | 814 | 818 | 4.0 | | |
| 3 | 815 | 819 | 4.0 | 4.1 | 0.6 |
| 4 | 817 | 820.5 | 3.5 | | |
| 5 | 814 | 818 | 4.0 | | |
| 0.00005 nM | | | | | |
| 1 | 816 | 819 | 3.0 | | |
| 2 | 815 | 819 | 4.0 | | |
| 3 | 814 | 817 | 3.0 | 3.4 | 0.5 |
| 4 | 813 | 817 | 4.0 | | |
| 5 | 815 | 818 | 3.0 | | |

TABLE 4

$\lambda_{LSPR}$ responses from plasmonic biosensor exosed to different concentrations of miR-21 in 40% bovine plasma.

| Sensor # | $\lambda_{LSPR}$ (nm) for HS-C6-ssDNA-21: PEG$_6$SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 818 | 832 | 14.0 | | |
| 2 | 819 | 835 | 16.0 | | |
| 3 | 815 | 827 | 12.0 | 14.0 | 2.0 |
| 4 | 818 | 834 | 16.0 | | |
| 5 | 815 | 827 | 12.0 | | |
| | | 10 nM | | | |
| 1 | 819 | 830 | 11.0 | | |
| 2 | 818 | 827 | 9.0 | | |
| 3 | 818 | 828 | 10.0 | 10.2 | 0.8 |
| 4 | 815 | 826 | 11.0 | | |
| 5 | 820 | 830 | 10.0 | | |
| | | 1 nM | | | |
| 1 | 819 | 829 | 10.0 | | |
| 2 | 818 | 826 | 8.0 | | |
| 3 | 821 | 827 | 6.0 | 8.0 | 1.4 |
| 4 | 816 | 824 | 8.0 | | |
| 5 | 815 | 823 | 8.0 | | |
| | | 0.1 nM | | | |
| 1 | 816 | 824 | 8.0 | | |
| 2 | 818 | 827 | 9.0 | | |
| 3 | 815 | 821 | 6.0 | 7.6 | 1.1 |
| 4 | 819 | 826 | 7.0 | | |
| 5 | 819 | 827 | 8.0 | | |
| | | 0.01 nM | | | |
| 1 | 820 | 827 | 7.0 | | |
| 2 | 816 | 821 | 5.0 | | |
| 3 | 820 | 826 | 6.0 | 6.2 | 0.8 |
| 4 | 821 | 827 | 6.0 | | |
| 5 | 818 | 825 | 7.0 | | |
| | | 0.001 nM | | | |
| 1 | 820 | 825 | 5.0 | | |
| 2 | 818 | 824 | 6.0 | | |
| 3 | 817 | 821 | 4.0 | 4.6 | 0.9 |
| 4 | 816 | 820 | 4.0 | | |
| 5 | 817 | 821 | 4.0 | | |
| | | 0.0001 nM | | | |
| 1 | 816 | 819 | 3.0 | | |
| 2 | 817 | 820.6 | 3.6 | | |
| 3 | 815 | 818.4 | 3.4 | 3.4 | 0.3 |
| 4 | 816 | 819.7 | 3.7 | | |
| 5 | 818 | 821.4 | 3.4 | | |

TABLE 5

$\lambda_{LSPR}$ responses from plasmonic biosensor exposed to different concentrations of miR-10b in PBS buffer.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 100 nM | | | |
| 1 | 820 | 835 | 15.0 | | |
| 2 | 823 | 837 | 14.0 | | |
| 3 | 821 | 836 | 15.0 | 15.2 | 0.8 |
| 4 | 824 | 840 | 16.0 | | |
| 5 | 818 | 834 | 16.0 | | |
| | | 10 nM | | | |
| 1 | 822 | 833 | 11.0 | | |
| 2 | 820 | 832 | 12.0 | | |
| 3 | 821 | 832 | 11.0 | 11.4 | 1.1 |
| 4 | 820 | 830 | 10.0 | | |
| 5 | 823 | 836 | 13.0 | | |
| | | 1 nM | | | |
| 1 | 818 | 828 | 10.0 | | |
| 2 | 820 | 831 | 11.0 | | |
| 3 | 824 | 834 | 10.0 | 10.4 | 0.5 |
| 4 | 818 | 828 | 10.0 | | |
| 5 | 819 | 830 | 11.0 | | |
| | | 0.1 nM | | | |
| 1 | 820 | 829 | 9.0 | | |
| 2 | 818 | 827 | 9.0 | | |
| 3 | 822 | 830 | 8.0 | 8.6 | 0.5 |
| 4 | 821 | 829 | 8.0 | | |
| 5 | 819 | 828 | 9.0 | | |
| | | 0.01 nM | | | |
| 1 | 820 | 828 | 8.0 | | |
| 2 | 819 | 825 | 6.0 | | |
| 3 | 824 | 831 | 7.0 | 7.2 | 1.3 |
| 4 | 821 | 830 | 9.0 | | |
| 5 | 820 | 826 | 6.0 | | |
| | | 0.001 nM | | | |
| 1 | 821 | 828 | 7.0 | | |
| 2 | 820 | 826 | 6.0 | | |
| 3 | 819 | 827 | 8.0 | 6.2 | 1.3 |
| 4 | 820 | 825 | 5.0 | | |
| 5 | 819 | 824 | 5.0 | | |
| | | 0.0001 nM | | | |
| 1 | 819 | 824 | 5.0 | | |
| 2 | 820 | 824 | 4.0 | | |
| 3 | 822 | 827 | 5.0 | 4.0 | 1.0 |
| 4 | 819 | 822 | 3.0 | | |
| 5 | 818 | 821 | 3.0 | | |
| | | 0.00005 nM | | | |
| 1 | 815 | 818 | 3 | | |
| 2 | 820 | 823.3 | 3.3 | | |
| 3 | 819 | 821.6 | 2.6 | 3.0 | 0.3 |
| 4 | 817 | 820 | 3 | | |
| 5 | 821 | 824 | 3 | | |

TABLE 6

$\lambda_{LSPR}$ responses from plasmonic biosensor exposed to different concentrations of miR-10b in 40% human plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 100 nM | | | |
| 1 | 822 | 835 | 13.0 | | |
| 2 | 820 | 831 | 11.0 | | |
| 3 | 817 | 829 | 12.0 | 12.2 | 0.8 |
| 4 | 821 | 833 | 12.0 | | |
| 5 | 819 | 832 | 13.0 | | |

TABLE 6-continued $\lambda_{LSPR}$ responses from plasmonic biosensor exposed to different concentrations of miR-10b in 40% human plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 10 nM | | | |
| 1 | 820 | 830 | 10.0 | | |
| 2 | 818 | 830 | 12.0 | | |
| 3 | 816 | 827 | 11.0 | 10.4 | 1.1 |
| 4 | 820 | 830 | 10.0 | | |
| 5 | 815 | 824 | 9.0 | | |
| | | 1 nM | | | |
| 1 | 821 | 830 | 9.0 | | |
| 2 | 816 | 824 | 8.0 | | |
| 3 | 820 | 828 | 8.0 | 8.2 | 0.4 |
| 4 | 815 | 823 | 8.0 | | |
| 5 | 817 | 825 | 8.0 | | |
| | | 0.1 nM | | | |
| 1 | 820 | 828 | 8.0 | | |
| 2 | 820 | 827 | 7.0 | | |
| 3 | 816 | 824 | 8.0 | 7.2 | 0.8 |
| 4 | 818 | 825 | 7.0 | | |
| 5 | 817 | 823 | 6.0 | | |
| | | 0.01 nM | | | |
| 1 | 820 | 827 | 7.0 | | |
| 2 | 817 | 823 | 6.0 | | |
| 3 | 823 | 830 | 7.0 | 6.4 | 0.5 |
| 4 | 815 | 821 | 6.0 | | |
| 5 | 822 | 828 | 6.0 | | |
| | | 0.001 nM | | | |
| 1 | 820 | 826 | 6.0 | | |
| 2 | 818 | 824 | 6.0 | | |
| 3 | 815 | 820 | 5.0 | 5.4 | 0.5 |
| 4 | 823 | 828 | 5.0 | | |
| 5 | 820 | 825 | 5.0 | | |
| | | 0.0001 nM | | | |
| 1 | 820 | 824 | 4.0 | | |
| 2 | 817 | 821 | 4.0 | | |
| 3 | 822 | 825.5 | 3.5 | 4.1 | 0.4 |
| 4 | 817 | 821.5 | 4.5 | | |
| 5 | 818 | 822.5 | 4.5 | | |
| | | 0.00005 nM | | | |
| 1 | 817 | 820.5 | 3.5 | | |
| 2 | 820 | 823 | 3.0 | | |
| 3 | 816 | 818.5 | 2.5 | 3.0 | 0.4 |
| 4 | 820 | 823 | 3.0 | | |
| 5 | 823 | 826 | 3.0 | | |

TABLE 7

$\lambda_{LSPR}$ responses from plasmonic biosensor exposed to different concentrations of miR-10b in 40% bovine plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 100 nM | | | |
| 1 | 818 | 830 | 12.0 | | |
| 2 | 821 | 831 | 10.0 | | |
| 3 | 819 | 834 | 15.0 | 12.0 | 1.9 |
| 4 | 820 | 832 | 12.0 | | |
| 5 | 816 | 827 | 11.0 | | |
| | | 10 nM | | | |
| 1 | 820 | 835 | 15.0 | | |
| 2 | 819 | 828 | 9.0 | | |
| 3 | 822 | 830 | 8.0 | 9.2 | 3.3 |
| 4 | 819 | 826 | 7.0 | | |
| 5 | 821 | 828 | 7.0 | | |
| | | 1 nM | | | |
| 1 | 821 | 828 | 7.0 | | |
| 2 | 819 | 828 | 9.0 | | |
| 3 | 821 | 830 | 9.0 | 8.8 | 1.1 |
| 4 | 818 | 828 | 10.0 | | |
| 5 | 819 | 828 | 9.0 | | |
| | | 0.1 nM | | | |
| 1 | 819 | 824 | 5.0 | | |
| 2 | 821 | 828 | 7.0 | | |
| 3 | 819 | 825 | 6.0 | 6.2 | 0.8 |
| 4 | 818 | 825 | 7.0 | | |
| 5 | 820 | 826 | 6.0 | | |
| | | 0.01 nM | | | |
| 1 | 821 | 825 | 4.0 | | |
| 2 | 818 | 824 | 6.0 | | |
| 3 | 822 | 826 | 4.0 | 4.2 | 1.1 |
| 4 | 820 | 823 | 3.0 | | |
| 5 | 820 | 824 | 4.0 | | |
| | | 0.001 nM | | | |
| 1 | 821 | 825 | 4.0 | | |
| 2 | 819 | 822 | 3.0 | | |
| 3 | 818 | 821 | 3.0 | 3.4 | 0.5 |
| 4 | 820 | 824 | 4.0 | | |
| 5 | 818 | 821 | 3.0 | | |
| | | 0.0001 nM | | | |
| 1 | 819 | 822 | 3.0 | | |
| 2 | 818 | 820 | 2.0 | | |
| 3 | 820 | 822.5 | 2.5 | 2.5 | 0.5 |
| 4 | 817 | 820 | 3.0 | | |
| 5 | 819 | 821 | 2.0 | | |

TABLE 8

$\lambda_{LSPR}$ responses from plasmonic biosensor prepared with 100% ssDNA-21 without spacers and exposed to different concentrations of miR-21 in 40% human plasma.

| Sensor # | $\lambda_{LSPR}$ (nm) for HS-C6-ssDNA-21 functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 810 | 820 | 10.0 | | |
| 2 | 811 | 822 | 11.0 | | |
| 3 | 809 | 818 | 9.0 | 9.6 | 1.1 |
| 4 | 810 | 820 | 10.0 | | |
| 5 | 809 | 817 | 8.0 | | |

TABLE 8-continued $\lambda_{LSPR}$ responses from plasmonic biosensor prepared with 100% ssDNA-21 without spacers and exposed to different concentrations of miR-21 in 40% human plasma.

| Sensor # | $\lambda_{LSPR}$ (nm) for HS-C6-ssDNA-21 functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 10 nM | | | |
| 1 | 808 | 817 | 9.0 | | |
| 2 | 810 | 820 | 10.0 | | |
| 3 | 808 | 816 | 8.0 | 7.8 | 1.8 |
| 4 | 811 | 817 | 6.0 | | |
| 5 | 809 | 815 | 6.0 | | |
| | | 1 nM | | | |
| 1 | 809 | 814 | 5.0 | | |
| 2 | 810 | 814 | 4.0 | | |
| 3 | 811 | 817 | 6.0 | 5.2 | 1.3 |
| 4 | 810 | 815 | 5.0 | | |
| 5 | 808 | 814 | 6.0 | | |
| | | 0.1 nM | | | |
| 1 | 811 | 816 | 5.0 | | |
| 2 | 810 | 814 | 4.0 | | |
| 3 | 810 | 815 | 5.0 | 4.6 | 0.6 |
| 4 | 808 | 812 | 4.0 | | |
| 5 | 809 | 814 | 5.0 | | |
| | | 0.01 nM | | | |
| 1 | 807 | 810 | 3.0 | | |
| 2 | 808 | 812 | 4.0 | | |
| 3 | 810 | 813 | 3.0 | 3.4 | 0.5 |
| 4 | 809 | 812 | 3.0 | | |
| 5 | 808 | 812 | 4.0 | | |

TABLE 9

Calibration curve and the LODs derived for synthetic miR-X (X = 21, 10b) in different media.

| Type of miR-X | Physical media | Equation from calibration curve | $R^2$ value | Z value (nm) | LOD (fM) |
|---|---|---|---|---|---|
| X = 21 | PBS buffer | Y = 0.9185ln(X) + 12.5 | 0.95 | 2.7 | 23.2 |
| | 40% human plasma | Y = 0.5735ln(X) + 9.103 | 0.98 | 3.1 | 28.4 |
| | 40% bovine plasma | Y = 0.6887ln(X) + 9.2714 | 0.93 | 2.2 | 34.6 |
| X = 10b | PBS buffer | Y = 0.7466ln(X) + 10.679 | 0.97 | 2.8 | 26.1 |
| | 40% human plasma | Y = 0.5748ln(X) + 8.9821 | 0.98 | 3.1 | 35.9 |
| | 40% bovine plasma | Y = 0.6887ln(X) + 8.1571 | 0.97 | 1.3 | 47.4 |

TABLE 10

The limit of detection (LOD) calculated for the plasmonic biosensors in different media for miR-21 and miR-10b.

| Type of miR-X | Physical media | LOD (fM) | LOD (fg/μL) |
|---|---|---|---|
| X = 21 | PBS buffer | 23.2 | 0.154 |
| | 40% human plasma | 28.4 | 0.189 |
| | 40% bovine plasma | 34.7 | 0.231 |
| X = 10b | PBS buffer | 26.1 | 0.181 |
| | 40% human plasma | 35.9 | 0.249 |
| | 40% bovine plasma | 47.4 | 0.329 |

TABLE 11

$\lambda_{LSPR}$ responses from plasmonic biosensor for miR-21 from extracted total RNAs in plasma samples collected from PDAC patients.

| Sensor # | $\lambda_{LSPR}$ (nm) for HS-C6-ssDNA-21: PEG$_6$SH functionalized gold nanoprisms | $\lambda_{LSPR}$ (nm) after incubation in extracted RNAs samples from PDAC patients | $\Delta\lambda_{LSPR}$ (nm) | Average $\Delta\lambda_{LSPR}$ (nm) | S.D. |
|---|---|---|---|---|---|
| | | Sample-1 | | | |
| 1 | 820 | 825.5 | 5.5 | | |
| 2 | 818 | 824 | 6.0 | | |
| 3 | 820 | 826 | 6.0 | 6.0 | 0.4 |
| 4 | 819 | 825.5 | 6.5 | | |
| | | Sample-2 | | | |
| 1 | 818 | 823 | 5.0 | | |
| 2 | 819 | 824.5 | 5.5 | | |
| 3 | 818 | 824 | 6.0 | 5.4 | 0.4 |
| 4 | 816 | 821.2 | 5.2 | | |
| | | Sample-3 | | | |
| 1 | 819 | 823 | 4.0 | | |
| 2 | 818 | 823 | 5.0 | | |
| 3 | 821 | 824.8 | 3.8 | 4.4 | 0.6 |
| 4 | 817 | 821.8 | 4.8 | | |
| | | Sample-4 | | | |
| 1 | 817 | 820.8 | 3.8 | | |
| 2 | 819 | 822.5 | 3.5 | | |
| 3 | 818 | 822 | 4.0 | 3.8 | 0.2 |
| 4 | 820 | 824 | 4.0 | | |
| | | Sample-5 | | | |
| 1 | 819 | 822 | 3.0 | | |
| 2 | 818 | 821.8 | 3.8 | | |
| 3 | 820 | 823 | 3.0 | 3.5 | 0.5 |
| 4 | 818 | 822 | 4.0 | | |
| | | Sample-6 | | | |
| 1 | 818 | 821 | 3.0 | | |
| 2 | 817 | 819 | 2.0 | | |
| 3 | 819 | 822 | 3.0 | 2.5 | 0.5 |
| 4 | 818 | 820.2 | 2.2 | | |

TABLE 12

$\lambda_{LSPR}$ responses from plasmonic biosensor for miR-21 from extracted total RNAs in plasma samples collected from normal humans.

| Sensor # | $\lambda_{LSPR}$ (nm) for HS-C6-ssDNA-21: PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| | | Sample-1 | | | |
| 1 | 821 | 823 | 2.0 | | |
| 2 | 819 | 821.5 | 2.5 | | |
| 3 | 818 | 820.9 | 2.9 | 2.2 | 0.6 |
| 4 | 819 | 820.4 | 1.4 | | |
| | | Sample-2 | | | |
| 1 | 817 | 819.3 | 2.3 | | |
| 2 | 818 | 820.5 | 2.5 | | |
| 3 | 820 | 822.9 | 2.9 | 2.6 | 0.3 |
| 4 | 818 | 820.5 | 2.5 | | |
| | | Sample-3 | | | |
| 1 | 817 | 819 | 2.0 | | |
| 2 | 818 | 819.8 | 1.8 | | |
| 3 | 820 | 822.2 | 2.2 | 2.2 | 0.5 |
| 4 | 819 | 821.9 | 2.9 | | |

TABLE 12-continued $\lambda_{LSPR}$ responses from plasmonic biosensor for miR-21 from extracted total RNAs in plasma samples collected from normal humans.

| Sensor # | $\lambda_{LSPR}$ (nm) for HS-C6-ssDNA-21: PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| | | Sample-4 | | | |
| 1 | 818 | 818.5 | 0.5 | | |
| 2 | 818 | 819.1 | 1.1 | | |
| 3 | 819 | 821 | 2.0 | 1.5 | 0.9 |
| 4 | 820 | 822.5 | 2.5 | | |
| | | Sample-5 | | | |
| 1 | 817 | 819 | 2.0 | | |
| 2 | 819 | 820.8 | 1.8 | | |
| 3 | 821 | 823.6 | 2.6 | 1.9 | 0.6 |
| 4 | 820 | 821.2 | 1.2 | | |
| | | Sample-6 | | | |
| 1 | 816 | 817.2 | 1.2 | | |
| 2 | 819 | 821.6 | 2.6 | | |
| 3 | 820 | 820.8 | 0.8 | 1.5 | 0.8 |
| 4 | 818 | 819.2 | 1.2 | | |

TABLE 13

$\lambda_{LSPR}$ responses from plasmonic biosensor for miR-10b from extracted total RNAs in plasma samples collected from PDAC patients.

| Sensor # | $\lambda_{LSPR}$ (nm) for HS-C6-ssDNA-10b: PEG$_6$SH functionalized gold nanoprisms | $\lambda_{LSPR}$ (nm) after incubation in extracted RNAs samples from PDAC patients | $\Delta\lambda_{LSPR}$ (nm) | Average $\Delta\lambda_{LSPR}$ (nm) | S.D. |
|---|---|---|---|---|---|
| | | Sample-1 | | | |
| 1 | 821 | 827 | 6.0 | | |
| 2 | 820 | 827 | 7.0 | | |
| 3 | 822 | 828.3 | 6.3 | 6.2 | 0.8 |
| 4 | 819 | 824.6 | 5.6 | | |
| | | Sample-2 | | | |
| 1 | 819 | 824 | 5.0 | | |
| 2 | 819 | 824.8 | 5.8 | | |
| 3 | 821 | 826 | 5.0 | 5.3 | 0.4 |
| 4 | 817 | 822.5 | 5.5 | | |
| | | Sample-3 | | | |
| 1 | 818 | 823 | 5.0 | | |
| 2 | 821 | 826 | 5.0 | | |
| 3 | 821 | 826 | 5.0 | 4.8 | 0.5 |
| 4 | 817 | 821 | 4.0 | | |
| | | Sample-4 | | | |
| 1 | 822 | 825.5 | 3.5 | | |
| 2 | 821 | 825 | 4.0 | | |
| 3 | 818 | 821.8 | 3.8 | 3.8 | 0.2 |
| 4 | 819 | 823 | 4.0 | | |
| | | Sample-5 | | | |
| 1 | 819 | 822 | 3.0 | | |
| 2 | 820 | 823.5 | 3.5 | | |
| 3 | 821 | 824.7 | 3.7 | 3.3 | 0.4 |
| 4 | 817 | 820 | 3.0 | | |
| | | Sample-6 | | | |
| 1 | 818 | 820 | 2.0 | | |
| 2 | 819 | 821.4 | 2.4 | | |
| 3 | 821 | 823 | 2.0 | 2.1 | 0.2 |
| 4 | 818 | 820 | 2.0 | | |

TABLE 14

$\lambda_{LSPR}$ responses from plasmonic biosensor for miR-10b from extracted total RNAs in plasma samples collected from normal humans.

| Sensor # | $\lambda_{LSPR}$ (nm) for HS-C6-ssDNA-10b: PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| | | Sample-1 | | | |
| 1 | 822 | 824.6 | 2.6 | | |
| 2 | 821 | 824 | 3.0 | | |
| 3 | 820 | 822 | 2.0 | 2.2 | 0.7 |
| 4 | 818 | 819.3 | 1.3 | | |
| | | Sample-2 | | | |
| 1 | 820 | 821.6 | 1.6 | | |
| 2 | 819 | 820 | 1.0 | | |
| 3 | 822 | 823 | 1.0 | 1.3 | 0.4 |
| 4 | 818 | 819.6 | 1.6 | | |
| | | Sample-3 | | | |
| 1 | 819 | 820.8 | 1.8 | | |
| 2 | 822 | 823 | 1.0 | | |
| 3 | 820 | 821 | 1.0 | 1.1 | 0.5 |
| 4 | 819 | 819.5 | 0.5 | | |
| | | Sample-4 | | | |
| 1 | 820 | 821.3 | 1.3 | | |
| 2 | 820 | 821.6 | 1.6 | | |
| 3 | 817 | 819 | 2.0 | 1.6 | 0.3 |
| 4 | 819 | 820.3 | 1.3 | | |
| | | Sample-5 | | | |
| 1 | 818 | 819 | 1.0 | | |
| 2 | 822 | 824 | 2.0 | | |
| 3 | 820 | 821 | 1.0 | 1.2 | 0.5 |
| 4 | 820 | 820.8 | 0.8 | | |
| | | Sample-6 | | | |
| 1 | 819 | 821 | 2.0 | | |
| 2 | 817 | 819 | 2.0 | | |
| 3 | 820 | 821 | 1.0 | 1.5 | 0.6 |
| 4 | 819 | 820 | 1.0 | | |

TABLE 15

Comparison of $\Delta\lambda_{LSPR}$ responses with their concentrations and the qRT-PCR folds for miR-21 from extracted total RNAs from plasma samples collected from PDAC patients.

| Sample | ~$\Delta\lambda_{LSPR}$ (nm) | Concentration (fg/μL) | qRT-PCR folds |
|---|---|---|---|
| 1 | 6.0 | 345.4 | 8.12 |
| 2 | 5.4 | 187.4 | 4.34 |
| 3 | 4.4 | 65.2 | 1.24 |
| 4 | 3.8 | 30.8 | 0.714 |
| 5 | 3.5 | 22.5 | 0.572 |
| 6 | 2.5 | 8.4 | 0.172 |

TABLE 16

Comparison of $\Delta\lambda_{LSPR}$ responses with their concentrations for miR-21 from extracted total RNAs from plasma samples collected from normal humans.

| Sample | ~$\Delta\lambda_{LSPR}$ (nm) | Concentration (fg/μL) |
|---|---|---|
| 1 | 2.2 | 6.1 |
| 2 | 2.6 | 7.7 |
| 3 | 2.2 | 5.9 |
| 4 | 1.5 | 3.4 |
| 5 | 1.9 | 4.3 |
| 6 | 1.5 | 3.1 |

TABLE 17

Comparison of $\Delta\lambda_{LSPR}$ responses with their concentrations and the qRT-PCR folds for miR-10b from extracted total RNAs from plasma samples collected from PDAC patients.

| Sample | ~$\Delta\lambda_{LSPR}$ (nm) | Concentration (fg/μL) | qRT-PCR folds |
|---|---|---|---|
| 1 | 6.2 | 1298 | 30.5 |
| 2 | 5.3 | 340 | 10.7 |
| 3 | 4.8 | 161.3 | 5.0 |
| 4 | 3.8 | 42.5 | 1.23 |
| 5 | 3.3 | 22.1 | 0.711 |
| 6 | 2.1 | 4.2 | 0.115 |

TABLE 18

Comparison of $\Delta\lambda_{LSPR}$ responses with their concentrations for miR-10b from extracted total RNAs in plasma samples collected from normal humans.

| Sample | ~$\Delta\lambda_{LSPR}$ (nm) | Concentration (fg/μL) |
|---|---|---|
| 1 | 2.2 | 6.6 |
| 2 | 1.3 | 1.5 |
| 3 | 1.1 | 1.3 |
| 4 | 1.6 | 2.1 |
| 5 | 1.2 | 1.6 |
| 6 | 1.5 | 1.8 |

TABLE 19

$\lambda_{LSPR}$ responses from plasmonic biosensor for miR-21 in plasma samples without any extraction collected from PDAC patients.

| Sensor # | $\Delta\lambda_{LSPR}$ (nm) for HS-C6-ssDNA-21: PEG6SH functionalized gold nanoprisms | $\Delta\lambda_{LSPR}$ (nm) after incubation in plasma samples from PDAC patients | $\Delta\lambda_{LSPR}$ (nm) | Average $\Delta\lambda_{LSPR}$ (nm) | S.D. |
|---|---|---|---|---|---|
| | | Sample-1 | | | |
| 1 | 814 | 820.5 | 6.5 | | |
| 2 | 816 | 822 | 6.0 | | |
| 3 | 816 | 823 | 7.0 | 6.4 | 1.0 |
| 4 | 820 | 826 | 6.0 | | |
| | | Sample-2 | | | |
| 1 | 815 | 821 | 6.0 | | |
| 2 | 817 | 823 | 6.0 | | |
| 3 | 814 | 819.6 | 5.6 | 5.8 | 0.3 |
| 4 | 816 | 821.4 | 5.4 | | |
| | | Sample-3 | | | |
| 1 | 814 | 829.5 | 5.5 | | |
| 2 | 816 | 821 | 5.0 | | |
| 3 | 820 | 825 | 5.0 | 5.3 | 0.3 |
| 4 | 818 | 823.6 | 5.6 | | |
| | | Sample-4 | | | |
| 1 | 818 | 823 | 5.0 | | |
| 2 | 816 | 820.5 | 4.5 | | |
| 3 | 814 | 818.7 | 4.7 | 4.7 | 0.2 |
| 4 | 820 | 824.6 | 4.6 | | |
| | | Sample-5 | | | |
| 1 | 819 | 823 | 4.0 | | |
| 2 | 821 | 825.5 | 4.5 | | |
| 3 | 813 | 817 | 4.0 | 4.2 | 0.2 |
| 4 | 817 | 821.2 | 4.2 | | |
| | | Sample-6 | | | |
| 1 | 814 | 817.5 | 3.5 | | |
| 2 | 817 | 820.5 | 3.5 | | |
| 3 | 816 | 820 | 4.0 | 3.5 | 0.4 |
| 4 | 815 | 818 | 3.0 | | |

TABLE 20

Comparison of $\Delta\lambda_{LSPR}$ responses with their concentrations of miR-21 in plasma samples collected from PDAC patients.

| Sample | ~$\Delta\lambda_{LSPR}$ (nm) | Concentration (fg/μL) |
|---|---|---|
| 1 | 6.4 | 1202.1 |
| 2 | 5.8 | 338.8 |
| 3 | 5.3 | 150.5 |
| 4 | 4.7 | 52.2 |
| 5 | 4.2 | 21.1 |
| 6 | 3.5 | 7.6 |

Example 2

Fabrication of miR-10b Sensor, and Characterization of Long-Term Stability and Selectivity.

Chemically synthesized gold nanoprisms, which displayed $\lambda_{LSPR}$ at 750, 800, and 820 nm in acetonitrile with average edge-lengths of 34, 42, and 47 nm, respectively, as determined from scanning electron microscopy images, were used in sensor fabrication. A red-shift change in $\lambda_{LSPR}$ position occurred during the functionalization of gold nanoprisms with 42 nm of average edge-length, which were attached onto silanized glass. The red-shift of the $\lambda_{LSPR}$ position suggested an increase in local refractive index from the attachment of molecular species on the gold nanoprism's surface. The LODs of miR-10b detection for 34, 42, and 47 nm edge-length nanoprisms were calculated in human plasma and were found to be 47.5, 0.091, and 0.083 fM, respectively (see Table 22). The LODs were calculated by measuring the $\Delta\lambda_{LSPR}$ for the blank sample (mixed -S-PEG6:-SC6-ssDNA-10b functionalized gold nanoprisms attached onto silanized glass substrate) and then calculating the Z (mean+3σ) value. The Z value was then converted into the relative concentration using the calibration curve. The data suggest that as the edge-lengths of the nanoprisms increase, their sensing volume also increases, thereby enhancing the LSPR sensitivity of the nanoprisms. This result is also in agreement with the literature where largest gold nanoparticles demonstrated highest LSPR-based sensing ability towards the detection of proteins. Thus, a minute change in a nanoprism's local dielectric environment due to analyte absorption can dramatically influence the LSPR properties and $\lambda_{LSPR}$ position. It is important to mention that the final $\lambda_{LSPR}$ values after -ssDNA-miR-10b and miR-10b hybridization were determined in PBS buffer (wet LSPR-based sensors) instead of air in order to avoid the effects of bulk refractive index caused by the surrounding media (water). Moreover, our lowest LOD of 83 aM was more than $10^6$, $10^4$, and $10^1$ fold lower than the label-free fluorescent-, microring resonator-, and nanopore-based miR sensors, respectively. To the best of our knowledge, this is the lowest LOD reported for LSPR-based sensors for detecting any-type of biomolecules in complex physiological media such as human plasma. This label-free technique has also proven to be more sensitive than metal nanoparticle-based surface-enhanced Raman scattering sensing (LOD=1.5 fM) of mouse pancreatic tumor.

The best LOD of the LSPR-based sensors described in this example were fabricated with 47 nm edge-length gold nanoprisms and demonstrated an LOD of 83.2 aM. However, functionalization of gold nanoprisms with 1:1 mole ratio of HS-C6-ssDNA-10b and PEG6-SH shifted the $\lambda_{LSPR}$ peak to ~863 nm. Upon further incubation with miR-10b, the $\lambda_{LSPR}$ position shifted even closer to the near-infrared region, where other biological constituents present in the media and a water peak could interfere with reading the $\lambda_{LSPR}$ of nanoprisms and potentially cause misleading LOD values. Therefore, the 42-nm edge length nanoprisms ($\lambda_{LSPR}=\sim 800$ nm) (LOD=91 aM) were used for LSPR-based sensor fabrication for further studies as described below. The LOD was slightly lower (32.6 aM) and exhibited less background signal in the LSPR peak shift ($\Delta\lambda_{LSPR}$) in PBS buffer than in human plasma (91 aM) (Table 23). These data are in agreement with the finding of a higher LSPR-based detection of streptavidin in serum by comparison with PBS buffer. Therefore, it is possible that differences in ionic strength or salt concentrations between PBS buffer and plasma, in conjunction with some nonspecific adsorption of plasma protein could occur on the silanized glass substrate within the sensing volume of gold nanoprisms, which could explain the slight differences in assay sensitivity between PBS buffer and human plasma.

Figure 2:
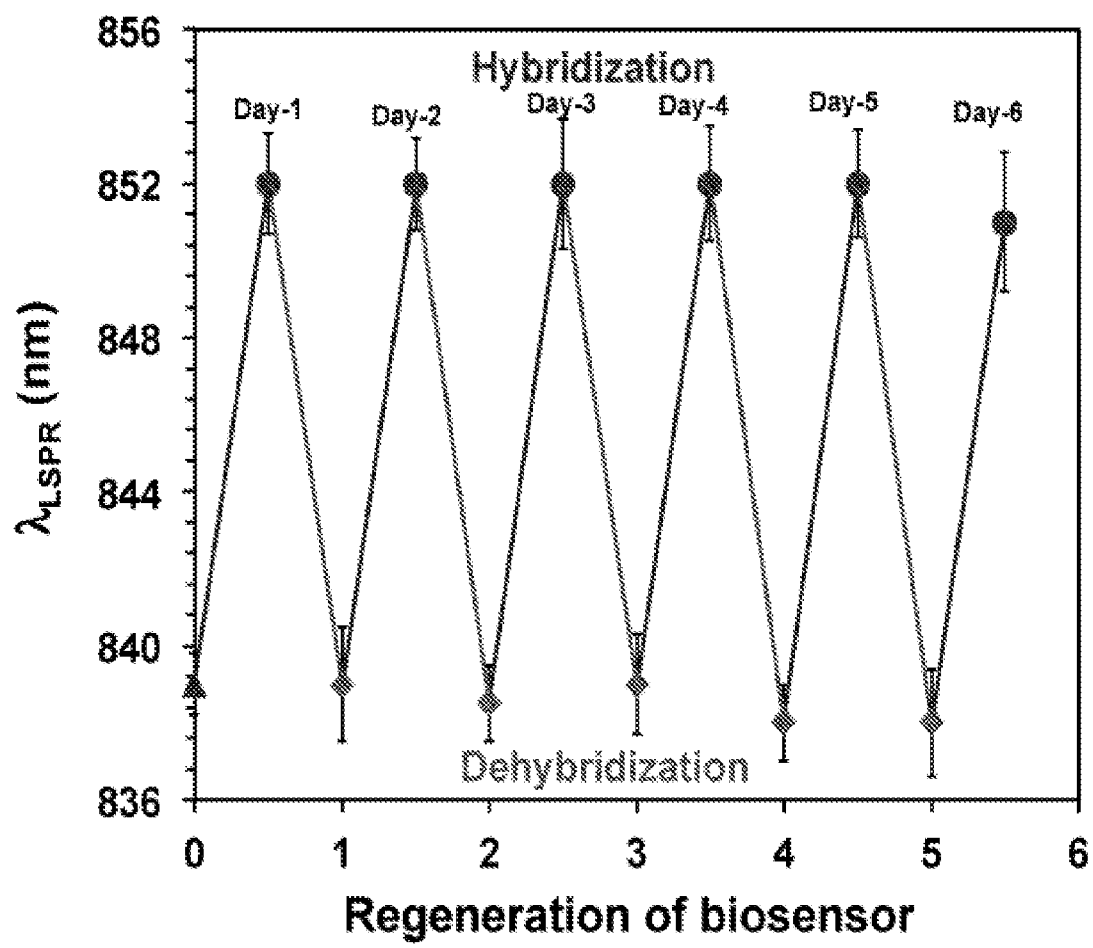
FIG. 2 is a plot showing changes in LSPR dipole peak position of gold nanoprisms functionalized with 1 µM:1 µM ratio of -C6-ssDNA-10b/-S-PEG6 upon hybridization and dehybridization for several cycles, as described in Example 2.

The regeneration ability of the LSPR-based sensor was tested by hybridization and dehybridization of miR-10b for at least 5 times over a 5-day period, using the same LSPR-based sensor while monitoring the $\lambda_{LSPR}$ shift, which was nearly identical each time before and after hybridization and dehybridization of miR-10b. The results are shown in FIG. 2. Therefore, the sensor is highly regenerative. Furthermore, the inert character of gold nanostructures towards biological constituents present in human plasma as well as the strong gold-sulfur bond which holds tightly the -ssDNA-10b, likely conferring long-term stability to the sensors, which will enhance their potential for development into point of care diagnostic tools. The LSPR-based sensors, which contain the specific antisense -ss-DNA-10b attached to the gold nanoprisms, were extremely specific towards their target miRs. The experimental data concerning regeneration and specificity of our sensors are discussed below. In the specificity study, 1.7 nm $\Delta\lambda_{LSPR}$ was observed when the LSPR-based sensor was incubated in a solution containing four different miRs (10 nM/miR; 40 nM total concentration). This value is very low in comparison to the 12.8 nm $\Delta\lambda_{LSPR}$ value observed upon incubation of our sensor with 10 nM miR-10b. Therefore, it is hypothesized that a $\Delta\lambda_{LSPR}$ of 1.7 nm could be due to a combination of instrumental noise and/or negligible nonspecific adsorption of miRs onto silanized glass substrate within the sensing volume of the gold nanoprisms, which was determined by us to be ~25 nm for 42 nm gold nanoprisms. Importantly, at the lower concentration range (100 fM and 100 aM), the $\Delta\lambda_{LSPR}$ values were same as blank samples (data not shown).

miR-10b has an identical seed sequence with miR-10a, but their mature forms differ at a single nucleotide. Thus, miR-10b and miR-10a contain nucleic acid A and U at the 12th position from 5' end, respectively. Moreover, the genes encoding miR-10b and 10a are located on chromosomes 2 and 17, respectively, and The Cancer Genome Atlas (TCGA) data indicate that 4% of PDACs exhibit miR-10b amplification and 4% exhibit miR-10a amplification, but these cases are not overlapping. Therefore, we next investigated the ability of our LSPR-based sensor to distinguish between miR-10b and miR-10a using the sensor, which was constructed with mixed -SC6-ssDNA-10b:-S-PEG6 in human plasma. The LSPR-based sensor displayed $\Delta\lambda_{LSPR}$ of 2.9 nm in 10 nM of miR-10a solution. This value is nearly 4.4 fold lower than $\Delta\lambda_{LSPR}$ observed for LSPR-based sensor upon incubation in 10 nM of miR-10b solution. No detectable $\lambda_{LSPR}$ shift was observed when miR-10a concentration was 1.0 µM.

This result is remarkable considering there is only one nucleotide difference between miR-10b and miR-10a, and that the sensor is proposed to rely on the -ssDNA:RNA duplex formation where attachment of miR-10b/10a to nanoprism-bound -ssDNA-10b increases the local dielectric environment and modulates $\Delta\lambda_{LSPR}$. It is believed that the 2.9 nm shift of $\Delta\lambda_{LSPR}$ for 10 nM of miR-10a was not controlled by the duplex formation between nanoprism-bound -ssDNA-10b and miR-10a since there is only a single nucleotide difference between them. This value is in agreement with the low molecular weight of miR-10a of -6.9 kDa that will only influence local dielectric environment minimally, and it is expected that at higher concentrations miR-10a would attach to the sensors and influence the LSPR properties.

It is hypothesized that due to -ssDNA-10b and miR-10b duplex formation, a long distance charge transport takes place that alters the electron density and electromagnetic field around the nanoprisms, resulting in alteration of their LSPR properties. A long distance charge transport through a duplex DNA backbone is known to occur where a single base pair mismatch influences the conductivity significantly. Therefore, it is believed in the case of duplex formation between nanoprisms bound -ssDNA-10b and miR-10a the delocalization of free electrons of gold nanoprisms throughout the entire DNA helix did not take place. In order to test this hypothesis, LSPR-based sensors were designed by functionalizing gold nanoprisms by -SC6-ssDNA-10a:-S-PEG6 and the sensitivity was determined using miR-10a in human plasma where LOD was found to be an -75 aM (data not shown). This result is expected because -ssDNA-10a and miR-10a form a duplex structure without any nucleotide mismatch, which would result in free electrons delocalization.

It is believed that one nucleotide difference would not alter duplex formation between -ssDNA-10b and miR-10a, and that most of the miR-10a would therefore be attached onto the sensor's surface, akin to the -ssDNA-10b/miR-10b duplex. To test this hypothesis, the level of unbound miR-10a in 1.0 nM solution was quantified after incubating with human plasma the LSPR-based sensor that was constructed with mixed -SC6-ssDNA-10b:-S-PEG6. The LSPR-based sensor displayed an average 2.5 nm shift of $\Delta\lambda_{LSPR}$, as expected. The miR-10a remaining in solution was then assayed using a sensor constructed with mixed -SC6-ssDNA-10a:-S-PEG6, which revealed an average 6.1 nm shift in the $\Delta\lambda_{LSPR}$. Based on the miR-10a calibration curve, this $\Delta\lambda_{LSPR}$ value corresponds to a concentration of $1.4\times10^1$ nM, which is $-7\times10^1$ fold lower than the original 1.0 nM miR-10a concentration. In parallel, the level of unbound miR-10b in 1.0 nM solution was quantified after incubating with human plasma the LSPR-based sensor that was constructed with mixed -SC6-ssDNA-10b:-S-PEG6. A 5.4 nm shift of $\Delta\lambda_{LSPR}$ was observed, which corresponds to a concentration of $4.3\times10^5$ nM using the equation for the calibration curve reported in Table 22. This value is only 3 fold lower than the value determined for miR-10a that was free in solution after incubation into miR-10b sensors. Thus, the vast majority of miR-10a and miR-10b formed a duplex with the -ssDNA-10b-based LSPR sensor, and a single nucleotide mismatch at the 12th position did not impede miR-10a duplex formation. Together, these results support the hypothesis of electron delocalization processes as a predominant factor of controlling the dramatic shift of $\Delta\lambda_{LSPR}$.

It is believe that this is the first LSPR-based sensing approach that is able to distinguish between nucleotides having a single base pair mismatch at concentrations <10 µM, which is at least a magnitude better than other label-free sensors. These experimental data are important in the context of precise quantification of miR-10b that is released by PCCs into the medium or circulation with a very low concentration as discussed below.

Quantitative Analysis of miR-10b Levels in Cultured Pancreatic Cancer Cells and Their Released Products.

Chemotherapy resistance occurring in conjunction with a propensity to metastasize and a lack of early stage screening procedures contributes to the high PDAC-related mortality. It has therefore been proposed that a noninvasive test for the early detection of PDAC could significantly improve screening strategies and ultimately lead to a vastly improved prognosis in this treatment-recalcitrant cancer. It has been suggested that miR-10b may be an ideal plasma biomarker for PDAC, and that glypican-1 carried by exosomes could serve as an early diagnostic marker for PDAC. To further explore the possibility that circulating miR-10b could serve as a sensitive diagnostic marker for PDAC, it was sought to establish a highly sensitive and quantitative assay for miR-10b concentrations in various biological compartments that include PCC-derived conditioned media, exosomes, and plasma. Here, for the first time, a sensing approach was demonstrated which is able to precisely quantify the concentration of (i) extracted miR-10b from human PCCs, (ii) miR-10b in Roswell Park Memorial Institute (RPMI) medium and Dulbecco's modified Eagle's medium (DMEM) from these cells, (iii) extracted miR-10b from exosomes from these PCCs, and (iv) miR-10b in exosome-free supernatants (Sup) generated following two sequential ultracentrifugations (Sup-1 and Sup-2) as described below. The detection method described herein overcomes the limitation of the most widely used technique, qRT-PCR, which can only provide relative miR values rather than actual miR concentrations and which require RNA extraction procedures. Because the pancreatic tumor microenvironment (TME) is hypoxic and hypoxia up-regulates miR-10b expression, AsPC-1, BxPC-3, and PANC-1 cells engineered to overexpress miR-10b were grown under normoxia and hypoxia (1% $O_2$) conditions. By analyzing the concentration of miRs directly in media from the above PCCs as well as in exosomes released by these PCCs, it was possible to investigate the proportion of miR-10b released by PCCs directly into the culture medium by comparison to its release via exosomes.

Media from AsPC-1, BxPC-3, and PANC-1 cells, which were grown under normoxia and hypoxia conditions were collected and miR-10b was quantified using the LSPR-based technique and by qRT-PCR. Aliquots of media were subjected to two sequential ultracentrifugations with an intervening PBS wash, and exosomes and supernatant-1 (Sup-1) were collected separately. Sup-1 was again ultracentrifuged at 100,000×g and Sup-2 wsa collected. The LSPR-based technique was used to quantify miR-10b directly in Sup-1 and Sup-2, while qRT-PCR was used to determine the relative miR-10b levels after RNA extraction. No visible residue was detected after the second ultracentrifugation.

Figure 3:
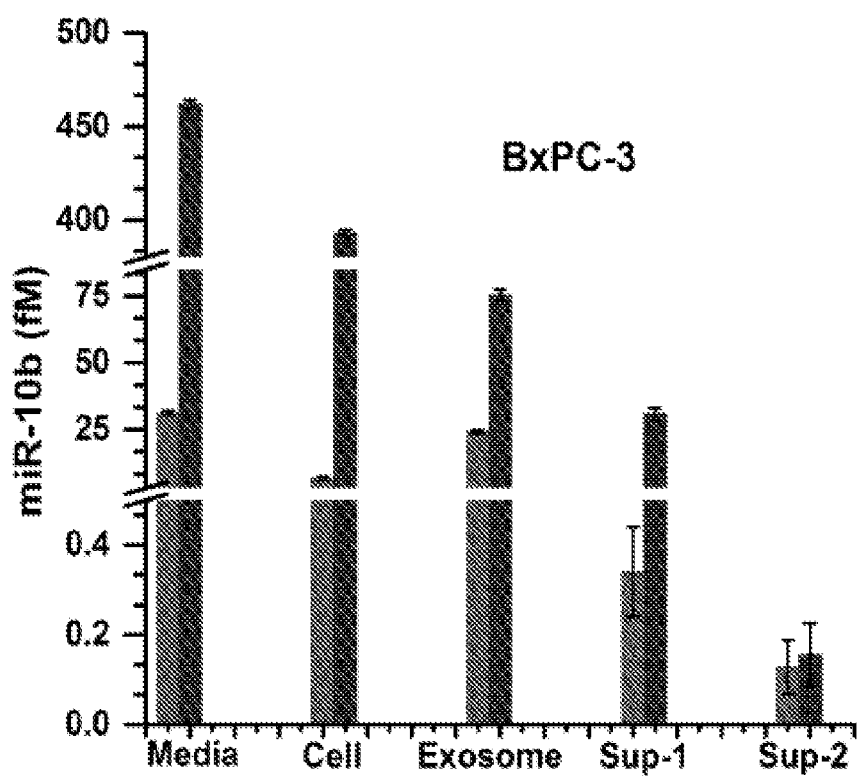
FIG. 3 is a plot of miR-10b concentration in various biological compartments of a BxPC-3 cell line, as determined by LSPR-based sensors, as described in Example 2, wherein the left bar in the pairs of bars is under normoxia conditions and the right bar in the pairs of bars is under hypoxia.
Figure 4:
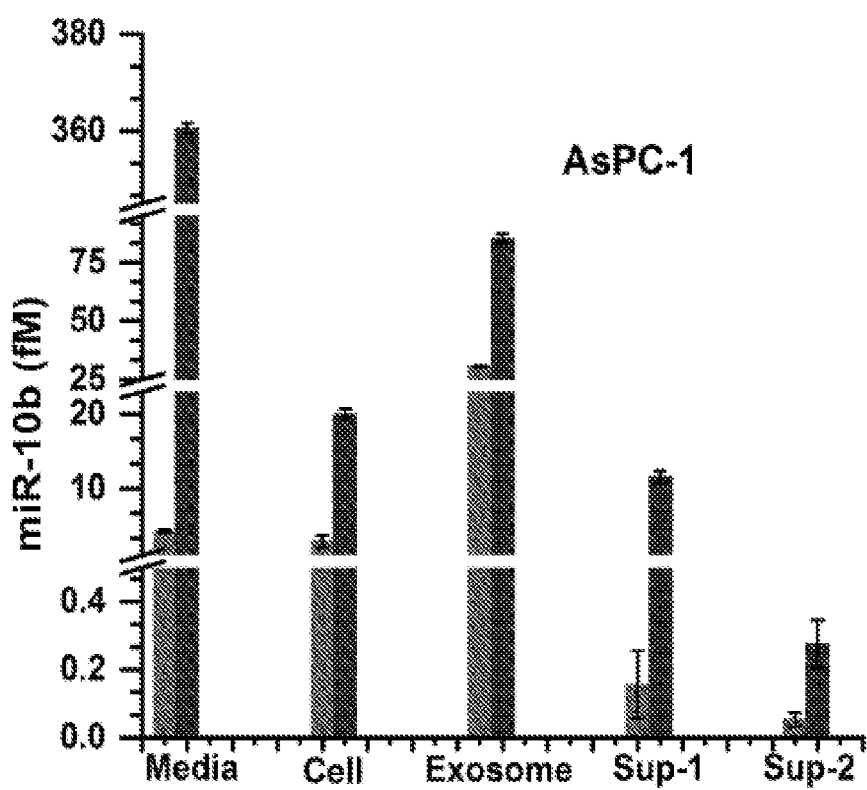
FIG. 4 is a plot of miR-10b concentration in various biological compartments of a AsPC-1 cell line, as determined by LSPR-based sensors, as described in Example 2 wherein the left bar in the pairs of bars is under normoxia conditions and the right bar in the pairs of bars is under hypoxia.
Figure 5:
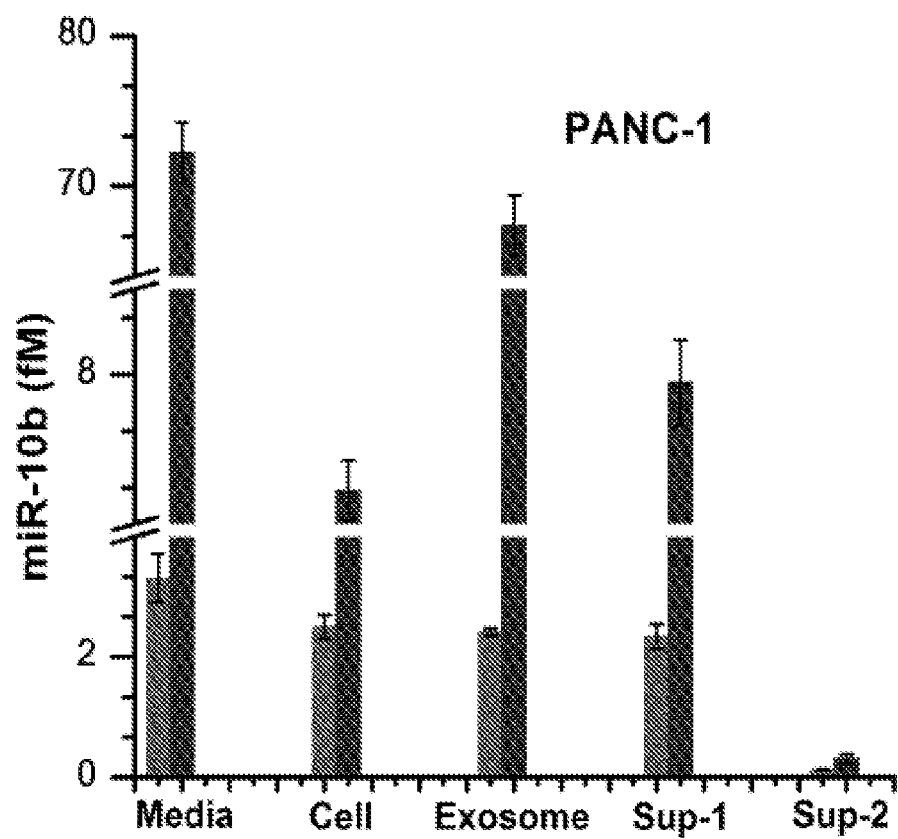
FIG. 5 is a plot of miR-10b concentration in various biological compartments of a PANC-1 cell line, as determined by LSPR-based sensors, as described in Example 2 wherein the left bar in the pairs of bars is under normoxia conditions and the right bar in the pairs of bars is under hypoxia.

To quantify miR-10b levels in the above PCCs cells ($4\times10^5$) were lysed and total RNA (including miRs) was extracted using a TRIzol kit followed by a single-step purification with the Direct-zol RNA MiniPrep kit which yielded a final elution volume of 30 µL/sample. Next, 14 µL from each sample were used for LSPR-based detection, whereas the remaining 14 L were used for qRT-PCR. miR-10b was quantified in crude media from each cell line by incubating over the LSPR-based sensor for 12 h, as described below. Subsequently, the sensors were washed with PBS buffer, and the $\lambda_{LSPR}$ was measured. FIGS. 3, 4, and 5 illustrate the LSPR-based determination of miR-10b concentrations in two types of media from three different PCCs. RPMI medium that was collected from BxPC-3 and AsPC-1 cells that were grown under hypoxia contained ~462, and 360 fM of miR-10b, respectively. DMEM collected from PANC-1 cells grown under hypoxia, contained -70 fM of miR-10b. We observed a similar pattern for miR-10b concentrations that were determined following extraction of total RNA from BxPC-3, AsPC-1, and PANC-1 cells of ~390, -20, and ~5 fM, respectively. The LSPR-based values were also compared with qRT-PCR data from the same samples and they showed the same general trend (FIGS. 6, 7, and 8).

FIGS. 3, 4, and 5 show the determination of miR-10b concentration in three different pancreatic cancer cell lines under two different culture conditions, normoxia (left bar in the pairs of bars) and hypoxia (right bar in the pairs of bars) in various biological compartments using the LSPR-based sensors. Determination of miR-10b concentrations in media, Sup-1, and Sup-2 was performed without RNA extraction, whereas total RNA was extracted from cells and exosomes. All three cell lines were engineered to overexpress miR-10b.

Figure 6:
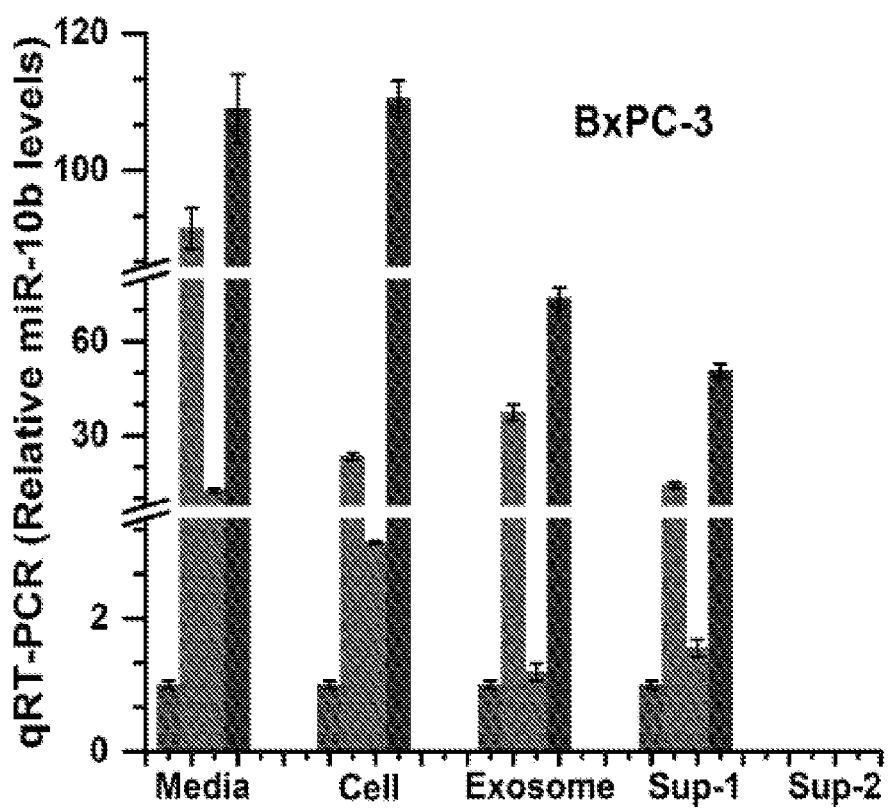
FIG. 6 is a plot of relative miR-10b levels in various biological compartments of a BxPC-3 cell line, as determined by qRT-PCR, as described in Example 2.
Figure 7:
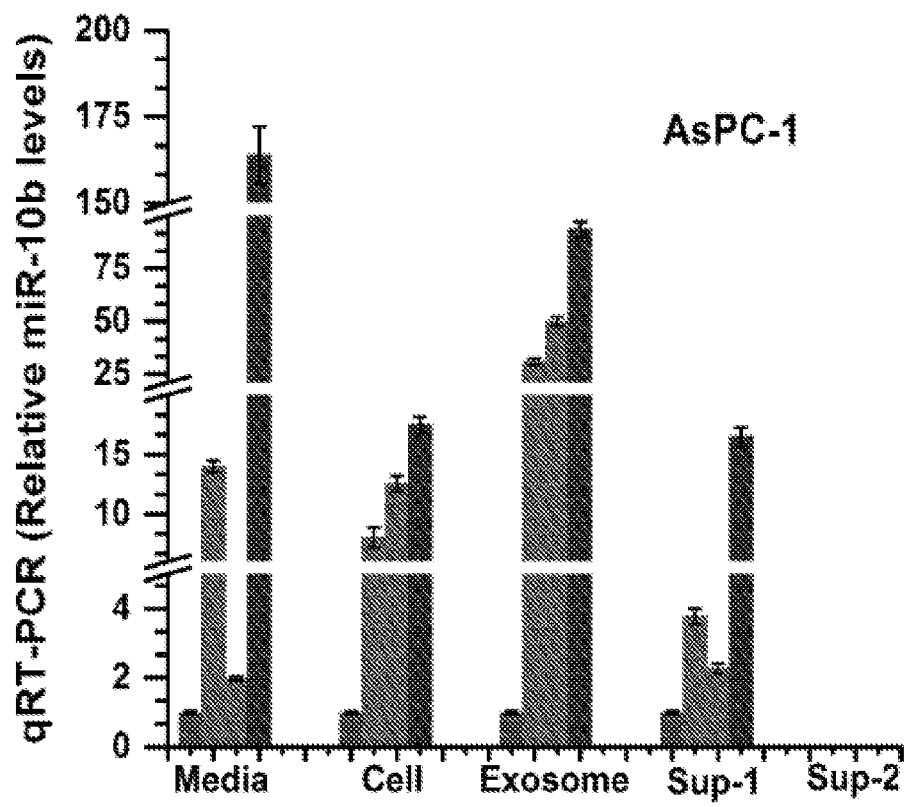
FIG. 7 is a plot of relative miR-10b levels in various biological compartments of a AsPC-1 cell line, as determined by qRT-PCR, as described in Example 2.
Figure 8:
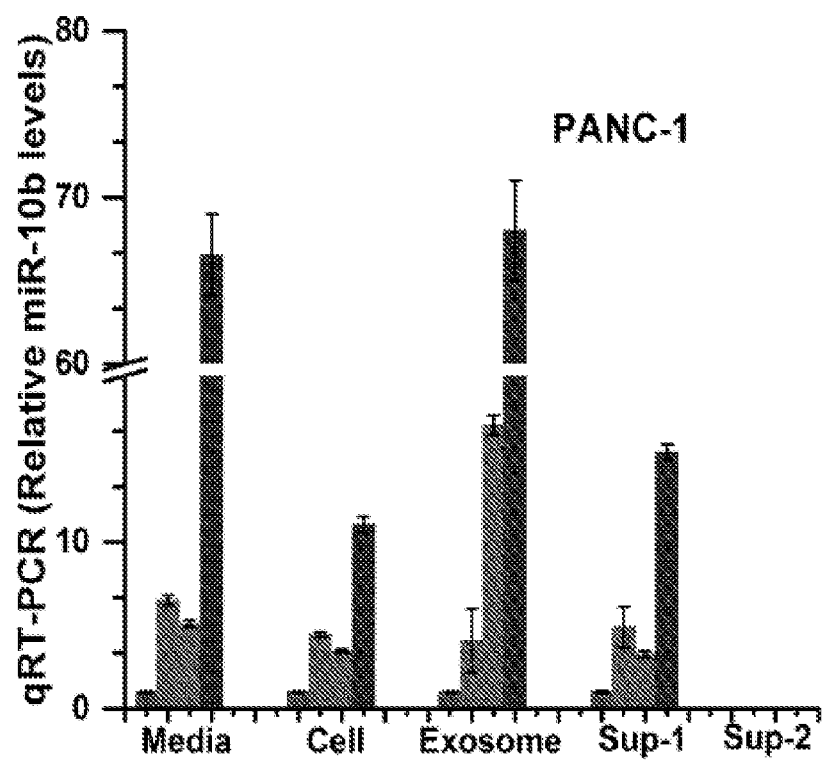
FIG. 8 is a plot of relative miR-10b levels in various biological compartments of a PANC-1 cell line, as determined by qRT-PCR, as described in Example 2.

FIGS. 6, 7, and 8 show qRT-PCR values for normoxia (left-most bar in the groups of four bars) and hypoxia (right-center bar in the group of four bars) using sham-transfected pancreatic cancer cells and cells engineered to overexpress miR-10b. miR-10b was assayed in total RNA extracted from media, cell, exosomes, and Sup-1 under normoxia (left-center bar in the group of four bars) and hypoxia (right-most bar in the group of four bars) conditions.

The LSPR-based concentration and qRT-PCR fold change in miR-10b levels in cells and exosomes were determined from aliquots derived from the corresponding total RNA samples. However, by qRT-PCR miR-10b was not detectable in Sup-2. The detailed procedure for exosomes isolation and RNAs extraction procedure are provided below.

To better understand the potential pathways for miR-10b release by PCCs, it was then sought to determine the concentrations of miR-10b in exosomes, and Sup-1 and Sup-2 generated following two sequential ultracentrifugations of media collected from PCCs that were cultured under hypoxia or normoxia conditions. Under hypoxia, miR-10b concentrations were -76 fM, -85 fM, and -67 fM in exosomes collected from BxPC-3, AsPC-1, and PANC-1 cell-derived media, respectively. The concentrations of miR-10b were -31 fM, -12 fM and -8 fM in Sup-1 from BxPC-3, AsPC-1, and PANC-1 cells, respectively, and in the -150-300 aM range in Sup-2 (FIGS. 3-5). A similar trend was observed in the qRT-PCR analysis (FIGS. 6-8). This is the lowest concentration determined by any label-free miR sensors without RNA extraction. By contrast, miR-10b levels were unable to be quantified in Sup-2. Therefore, the LSPR-based sensing technique described herein allows for the quantitative assay of miR-10b in diverse physiological media without requiring miR extraction, and is more sensitive than the widely used qRT-PCR technique.

Using this LSPR-based technique it was also determined that miR-10b levels under hypoxic conditions in exosomes were at least three-fold (AsPC-1 and BxPC-3 cells) and as high as twenty eight-fold (PANC-1 cells) higher than under normoxic conditions (FIGS. 3-5). The LSPR-based concentration values were also compared with the qRT-PCR results (from the same sample with total RNAs extraction) and miR-10b levels exhibited the same trend by qRT-PCR as by LSPR (FIGS. 6-8). To confirm that the assays measured miR-10b in exosomes, transmission electron microscopy (TEM) images of the exosomes, which were isolated from PANC-1 cell-derived medium, were obtained. The diameters of the exosomes were determined (-60-140 nm), even though some appeared to be aggregated, which could be due to the drying process during the TEM grid preparation. The detailed procedures for exosomes collection and RNAs extraction are provided below. These findings thus demonstrate that miR-10b concentrations are elevated under hypoxic conditions in exosomes, raising the possibility that miR-10b acts within the hypoxic TME to promote PDAC biological aggressiveness.

The data presented above on accurate quantification of miR-10b in various biological compartments using the ultrasensitive LSPR-based sensor provide insight into several important cellular processes that contribute to the release of miRs by PCCs in circulation. First, under hypoxia, miR-10b concentrations determined in exosomes collected from different cell lines were found to be comparable, and as high as 85 fM in ASPC-1 cells. Thus, PCCs release miR-10b rich exosomes into conditioned media, raising the possibility that it will be feasible to assay exosomal miRs as potential biomarkers of PDAC. Second, the concentrations of miR-10b in Sup-1 and Sup-2 were in the femtomolar and attomolar range in all three-cell lines. Therefore, some residual miRs were still present in the supernatant collected from media even after two sequential ultracentrifugations with intervening washing with PBS. The presence of miR-10b in Sup-1 and Sup-2 suggests that in addition to being released via exosomes, miRs are released directly by PCCs into their environment. Although the specific cellular pathways for miR-10b release remain to be delineated, it is conceivable that miR-10b could detach from Ago2 protein-miR complexes as byproducts of dead cells, or be released due to the rupturing of exosomes or microvesicles because of high mechanical force applied during ultracentrifugation. The miR-10 concentrations in exosomes were at least 15% (BxPC-3 cells) and as high as 84% (PANC-1 cells) of total extracellular miR-10b levels (media, Sup-1 and Sup-2). Overall, this disclosure describes the first comprehensive determination of miR concentrations at the attomolar range in various PCCs, under various growth conditions, and in different biological compartments. This investigation has significant implications for the development of biomarkers for the early diagnosis of PDAC through isolation and quantification of circulating miR-10b, as discussed in the next section, as well as for the diagnosis of other cancers in which circulating miRs are elevated.

Exosome miR-10b Levels in Patients with Pancreatic Cancer and Chronic Pancreatitis (PC).

Although hundreds of human miRs are known, their exact role in various aspects of cancer progression and modulation of cell proliferation, apoptosis, and metastasis is yet to be delineated. Importantly, these small, non-coding RNAs have the potential to serve as diagnostic markers for different diseases including PDAC. Plasma miR-10b levels, as determined by qRT-PCR, are elevated in PDAC patients by comparison with CP patients and normal control subjects or patients with gall-bladder disease. However, PCR-based assays require RNA extraction and purification, are only semi-quantitative, and are not sufficiently sensitive to differentiate miR-10b levels in patients with CP from levels in normal controls. As demonstrated above, the label-free, LSPR-based detection technique is not only able to assay attomolar concentrations of miR-10b directly in conditioned media, but also in PCC-derived exosomes. Therefore, it would be a breakthrough to establish an analytical technique that could be used to detect and quantify miR-10b directly in crude plasma samples.

Here, the first label-free assay to quantify and compare the miR levels between patients with PDAC (n=3), CP (n=3), and normal controls (n=3) is report. Moreover, the concentration of miR-10b in crude plasma, exosomes, and Sup-1 and Sup-2 is reported. The exosomes were collected from plasma through ultracentrifugation as described below. A brief TRIzol extraction, followed by a single-step purification using the direct-zol RNA MiniPrep kit makes this assay simple and innovative.

Exosomes are of endosomal origin and therefore express endosomal proteins such as tumor susceptibility gene 101 (Tsg101) and Alix. Exosomes that are of PDAC origin are also expected to express carbohydrate-associated 19-9 (CA19-9), which is a well-known pancreatic tumor marker in the circulation. To confirm that our plasma ultracentrifugation procedures yielded PDAC-derived exosomes, lysates of freshly isolated exosomes (20 µg/sample) and 50 µl of plasma supernatants were subjected to immunoblotting for TSG1, Alix, and CA19-9. The results show that plasma exosomes from PDAC patients express Alix, Tsg101, and CA19-9, and that the neither Alix nor Tsg101 are present in the plasma following the initial ultracentrifugation. By contrast, CA19-9, as expected, is present in exosome-depleted plasma.

Figure 9:
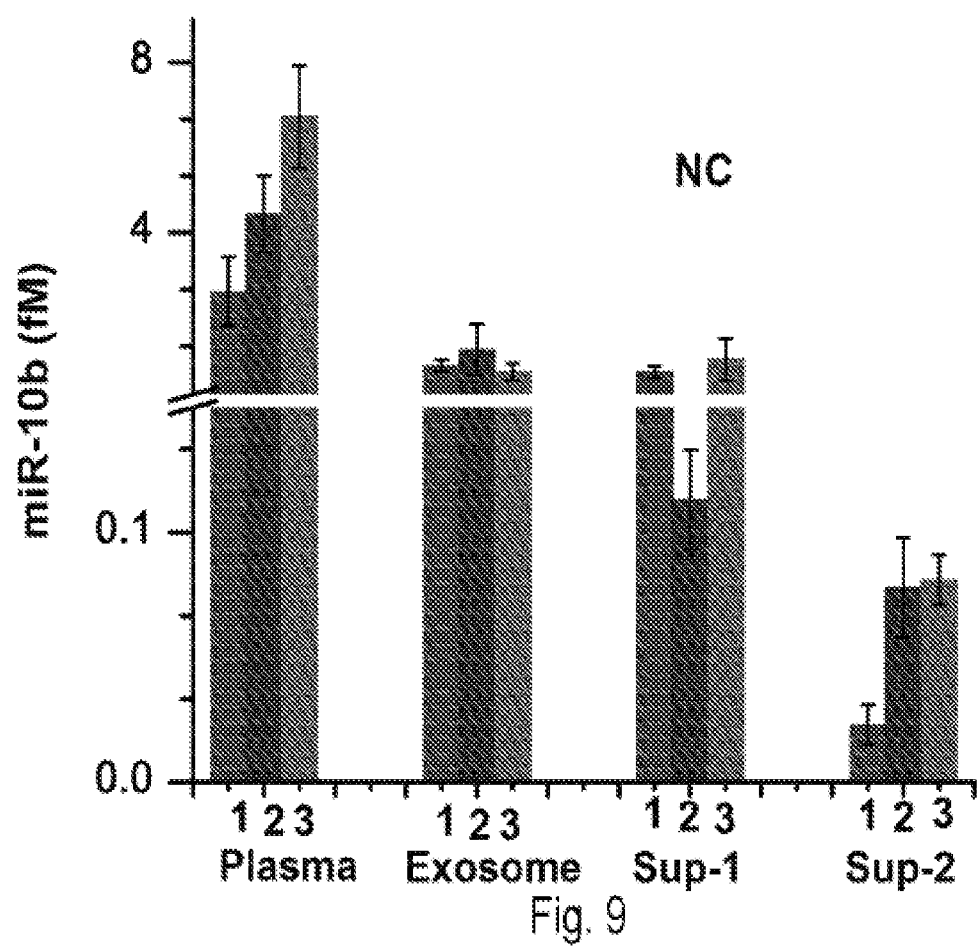
FIG. 9 is a plot of miR-10b concentration in various biological compartments from plasma samples of three normal controls, as determined by LSPR-based sensors, as described in Example 2.
Figure 10:
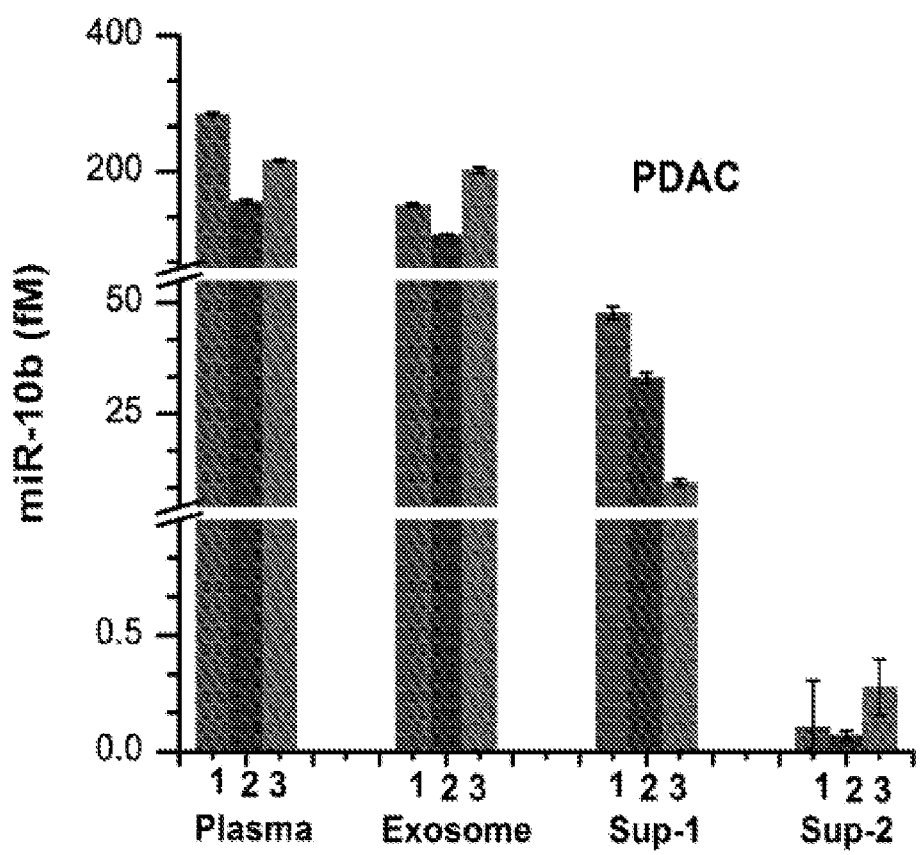
FIG. 10 is a plot of miR-10b concentration in various biological compartments from plasma samples of three patients with PDAC, as determined by LSPR-based sensors, as described in Example 2.
Figure 11:
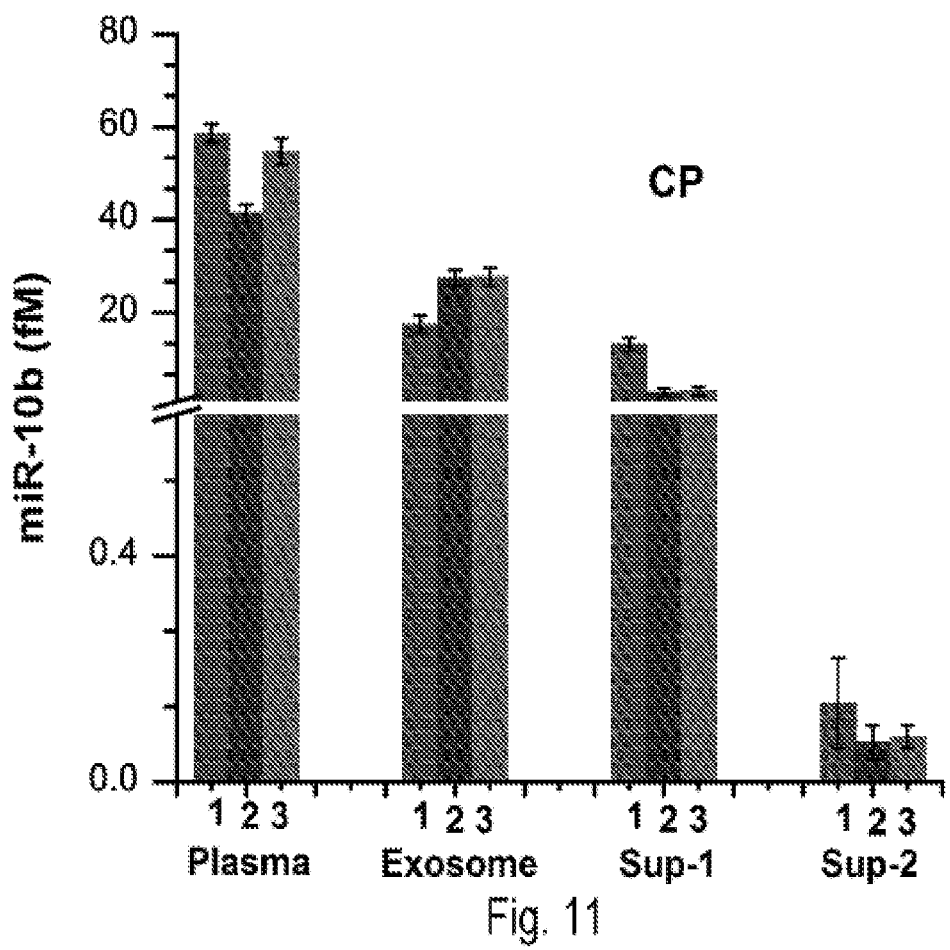
FIG. 11 is a plot of miR-10b concentration in various biological compartments from plasma samples of three patients with CP, as determined by LSPR-based sensors, as described in Example 2.
Figure 12:
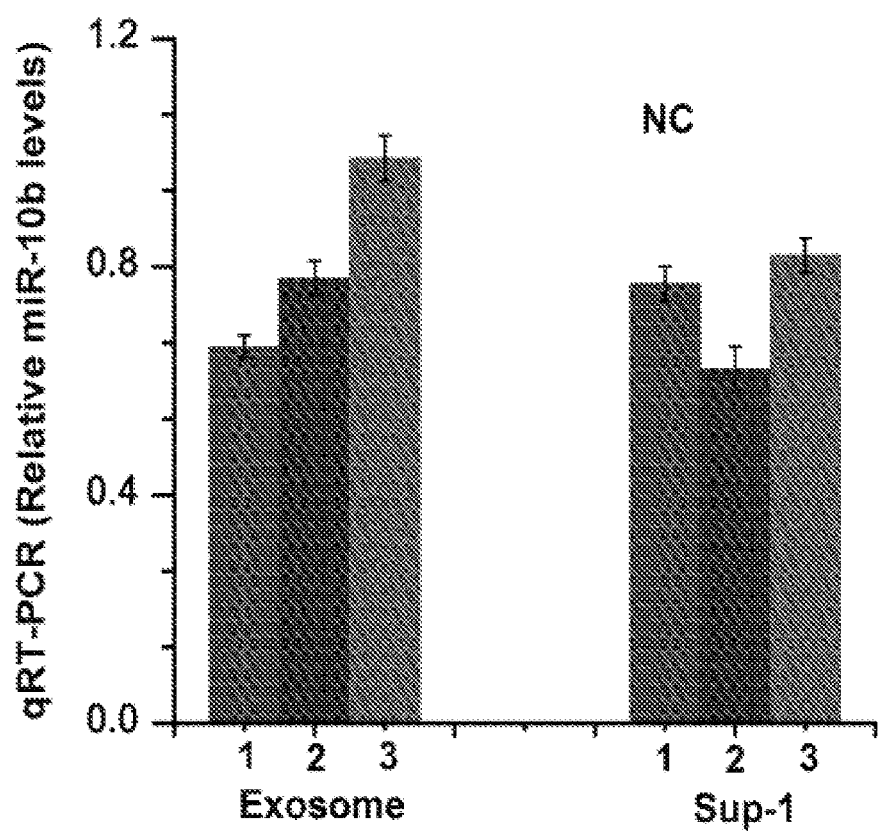
FIG. 12 is a plot of relative miR-10b levels in various biological compartments from plasma samples of three normal controls, as determined by qRT-PCR, as described in Example 2.
Figure 13:
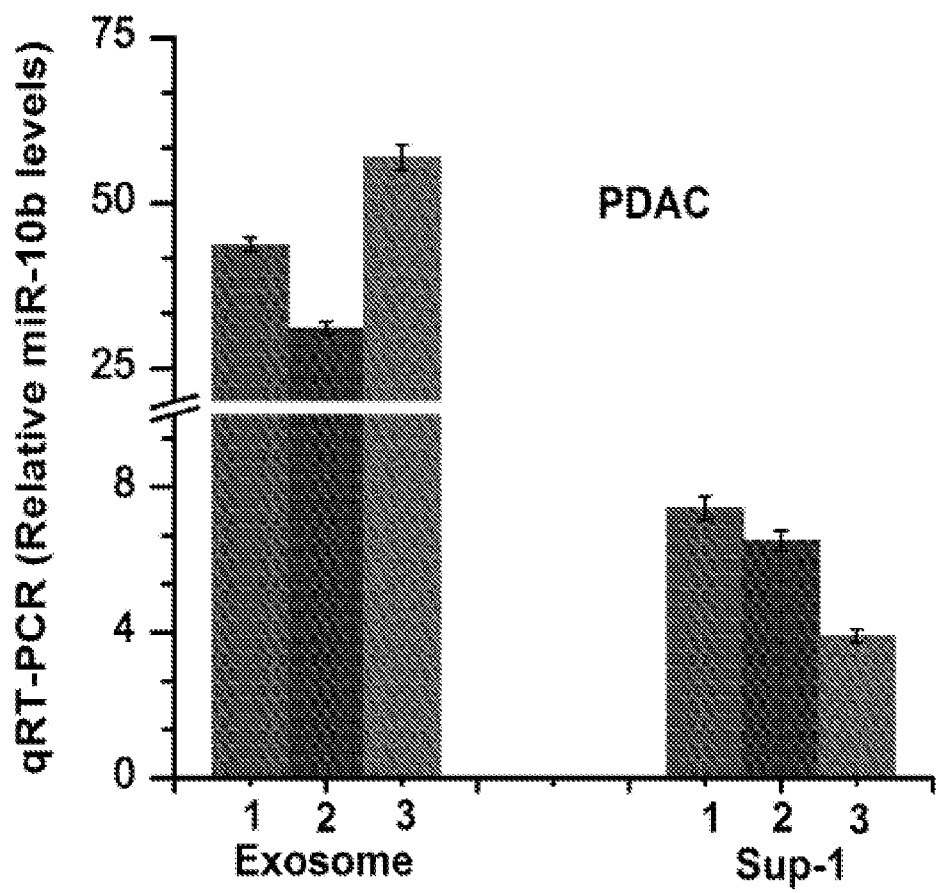
FIG. 13 is a plot of relative miR-10b levels in various biological compartments from plasma samples of three patients with PDAC, as determined by qRT-PCR, as described in Example 2.
Figure 14:
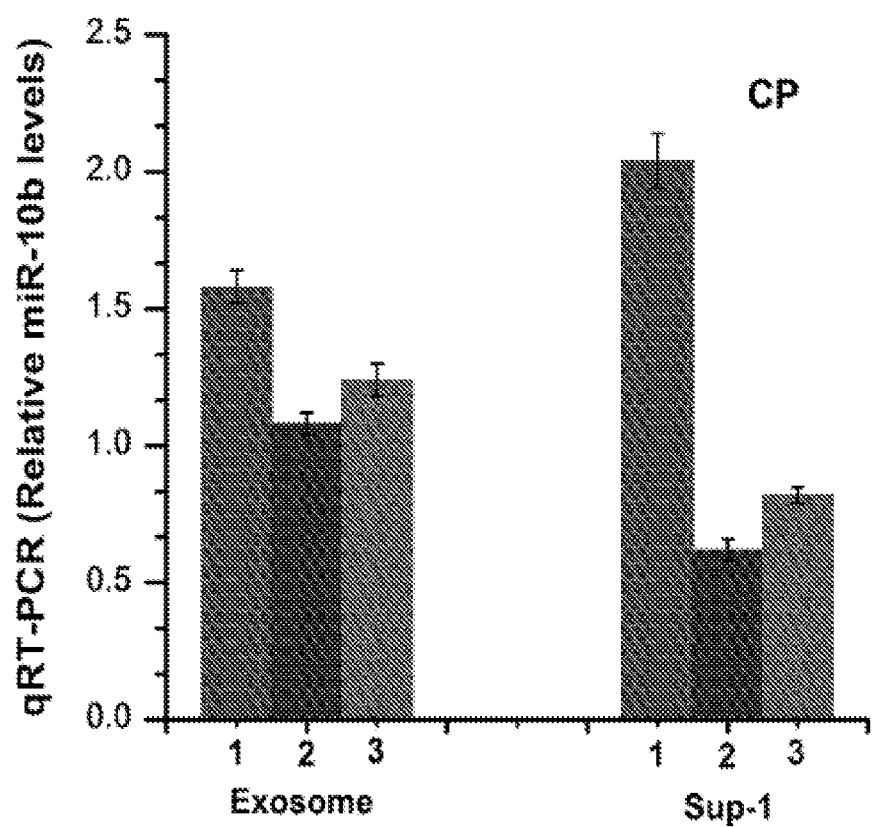
FIG. 14 is a plot of relative miR-10b levels in various biological compartments from plasma samples of three patients with CP, as determined by qRT-PCR, as described in Example 2.

FIGS. 9, 10, and 11 show a determination of miR-10b concentration in plasma samples from three normal control (NC), three patients with PDAC, and three patients with CP using the LSPR-based sensors described herein. Determination of miR-10b levels in plasma, Sup1, and Sup-2 were performed without RNA extraction, whereas total RNA was extracted from exosomes. FIGS. 12, 13, and 14 show qRT-PCR values for miR-10b from total RNA extracted from exosomes and Sup-1 in three NC, three patients with PDAC, and three patients with CP. The LSPR-based concentration and qRT-PCR values for miR-10b exosomes were determined from the same RNA samples from each subject, all performed in a blinded manner. Each individual bar represents a different subject. miR-10b levels in Sup-2 were below the level of detection by qRT-PCR and hence are not shown.

The concentrations of miR-10b in different biological compartments were determined using our LSPR-based assay, as shown in FIGS. 9, 10, and 11. All three samples from PDAC patients exhibited high levels of miR-10b in both plasma and circulating exosomes (FIG. 10). By contrast, the same LSPR-based assay revealed that miR-10b levels in plasma and exosomes from normal controls (FIG. 9) and CP patients (FIG. 11) were 50 to 60-fold lower and 4 to 10-fold lower, respectively, than the corresponding PDAC samples. Importantly, miR-10b levels in the CP samples (FIG. 11) were significantly higher than in normal controls (FIG. 9). FIGS. 12, 13, and 14 show the relative miR-10b levels determined by qRT-PCR. Supporting Information Table 7 provides the p values for the statistical analysis that was performed to compare PDAC, CP, and normal controls. Thus, the LSPR-based assay indicates that there are very high levels of miR-10b in the exosomes isolated from the plasma of PDAC patients, which is in contrast to observations in plasma from breast cancer patients where only 5% of miR-16, miR-21, and miR-24 were in the exosome compartment. Taken together, this data validate the hypothesis that PCCs are prone to release miR-10b as cargo within exosomes.

Comparing the LSPR- and qRT-PCR-based data, several conclusions can be drawn regarding the unique label-free technique. First, the trend of LSPR-based miR-10b concentration in exosomes and Sup-1 of three PDAC, three CP, and three normal control samples were identical to the well-established and most widely-used, qRT-PCR technique, underscoring the reliability of the nanoprism-based detection technique. Second, miR-10b levels in PDAC and CP samples were quantified directly in patient plasma, which cannot be accomplished by qRT-PCR. Third, the LSPR-based assay was able to quantify miR-10b level in Sup-2 but we were unable to extract sufficient RNAs from Sup-2 for quantification by qRT-PCR. This is due to the fact that the LSPR-based technique did not require any RNA extraction method, and is able to detect miR-10b in the sub-aM concentration range. Fourth, while qRT-PCR fails to differentiate between miR-10b levels in patients with CP by comparison with normal controls, the ultrasensitive LSPR-based sensor shows that plasma miR-10b levels are significantly higher in CP patients when compared to levels in normal controls. Moreover, there was at least a 5-fold increase in miR-10b levels in either plasma or exosomes in patients with CP when compared with normal controls. Thus, the LSPR-based detection technique displays unique aspects of modern analytical methodology that allows precise quantification of miRs at very low concentrations which is not feasible with any other known techniques.

CP is a chronic inflammatory condition of the pancreas associated with variable degrees of fibrosis which can lead to significant pancreatic exocrine and endocrine dysfunction, glucose intolerance, and diabetes. Although most patients with CP don't develop PDAC, it is well established that CP is associated with a higher risk for developing PDAC. However, there are no markers that will help stratify CP patients with respect to their risk for developing PDAC. Our observations that CP patients exhibit slight but significant increases in miR-10b levels in both the plasma and circulating exosomes by comparison with normal controls raise the possibility that monitoring for rising miR-10b levels in CP patients by using the ultrasensitive LSPR-based sensor could identify those patients that are at a high risk for developing PDAC and that need further evaluation by procedures such as endoscopic ultrasonography, thereby allowing for the early detection of CP progression to PDAC.

The LSPR-based quantification showed that miR-10b is present at high concentrations (~210 fM) in exosomes isolated from the plasma of PDAC patients, whereas the supernatants post-centrifugation (Sup-1: -10-50 fM, and Sup-2: 70-300 aM) had exceedingly low miR-10b levels. Therefore, the vast majority of miR-10b that is released by PCCs is present in the exosomes. Importantly, analysis of the TCGA data for PDAC revealed that many of the PDAC tissue samples in TCGA exhibit increased miR-10b expression, ranging as high as -180,000 reads per million (RPM). Moreover, there are five Stage IA and eight stage IB PDAC cases in the TCGA data, with mean miR-10b values of 13,400 RPM and 15,225 RPM, respectively, indicating that miR-10b is already elevated at the earliest stages of clinical presentation for PDAC. The simple, label-free, highly specific, and regenerative LSPR-based sensors would thus allow for quantitative measurements of miR-10b circulating in exosomes, which could serve as a biomarker for early PDAC diagnosis. Importantly, the working principle of the LSPR-based sensor is that the attachment of miR-10b to nanoprism-bound -ssDNA-10b increases the local dielectric environment and modulates $\Delta\lambda_{LSPR}$. Therefore, modifying the surface of the nanoprisms by any type of -ssDNA would allow for the quantitative detection of any complementary miR-X (for example, X=30c, 106b, 155, and 212) that is overexpressed in PDAC. This ultrasensitive assay will allow for the detection in plasma of miRs that are under-expressed in PDAC and other pathological conditions, and we have initiated the development of additional LSPR-based sensors that could quantify miR-X level, including those with single nucleotide specificity, in biological fluids and exosomes.

Chemicals. Chloro(triethylphosphine) gold (I) (Et3PAuCl, 97%), poly(methylhydrosiloxane) (PMHS, Mn=1700-3300), trioctylamine (TOA, 98%), ACS grade acetonitrile ($CH_3CN$, 99.9%), methanol (99.8%), human plasma (contains 4% trisodium citrate and tested for HIV, hepatitis C and hepatitis B), thiol modified ssDNAs, miRs (miRs), Tris-base, magnesium chloride ($MgCl_2$), and potassium chloride (KCl) were purchased from Sigma Aldrich and were used as received. (3-mercaptopropyl)-triethoxysilane (MPTES, 94%) was purchased from Alfa Aesar, and ethanol (alcohol 200 proof) was purchased from Decon labs. RNase H enzyme and RNase H reaction buffer were purchased from New England bio labs inc. RNase free sterile water was obtained from Baxter Healthcare Corporation. 1, 4-Dithiothreitol (DTT) was purchased from Roche Diagnostics. Anti-Alix (1:1000 dilution) from Sigma, anti-Tsg101 (1:200 dilution) from Santa Cruz, and anti-CA19-9 (1:200 dilution) from Abcam. Hydrochloric acid (HCl), sodium chloride (NaCl, >99.5%), sodium phosphate monobasic monohydrate ($NaH_2PO_4 \cdot H_2O$, >98%), sodium phosphate dibasic anhydrous ($Na_2HPO_4$), and the glass coverslips were purchased from Fisher Scientific. RBS 35 Detergent was obtained from Thermo Scientific and used as received. The super Sharpe silicon scanning probes (SSS-NCHR) for atomic force microscopy measurements were purchased from nanosensors. All water was purified using a Thermo Scientific Barnstead Nanopure system. Thiol modified oligonucleotides and all miRs were stored at $-20°$ C. RNase free sterile water was used to prepare the PBS buffer solution. Polyethylene glycol thiol (PEG6-SH) was synthesized in our laboratory using published procedures as set forth in Lawrence, K. N.; Johnson, M. A.; Dolai, S.; Kumbhar, A.; Sardar, R. Solvent-like ligand-coated ultrasmall cadmium selenide nanocrystals: strong electronic coupling in a self-organized assembly. *Nanoscale* 2015, 7, 11667-11677 and incorporated herein by reference in its entirety. TRIzol and TRIzol LS were purchased from Life Technologies. Direct-zol RNA MiniPrep kit was purchased from Zymo Research.

Synthesis of Gold Nanoprisms with Various Edge Lengths. Gold nanoprisms were chemically synthesized according to our previously developed procedure (as set forth in Joshi, G. K.; McClory, P. J.; Muhoberac, B. B.; Kumbhar, A.; Smith, K. A.; Sardar, R. Designing Efficient Localized Surface Plasmon Resonance-Based Sensing Platforms: Optimization of Sensor Response by Controlling the Edge Length of Gold Nanoprisms. *J. Phys. Chem. C* 2012, 116, 20990-21000; and Joshi, G. K.; Smith, K. A.; Johnson, M. A.; Sardar, R. Temperature-Controlled Reversible Localized Surface Plasmon Resonance Response of Polymer-Functionalized Gold Nanoprisms in the Solid State. *J. Phys. Chem. C* 2013, 117, 26228-26237 and both herein incorporated by reference in their entirety) with minor modification. Specifically, Et3PAu(I)Cl (8 mg, 0.02 mmol) was dissolved in 5 mL of acetonitrile and allowed to stir for 5 min at room temperature in an Erlenmeyer flask. 0.085 mL of TOA and 0.3 mL of PMHS were mixed with 1 mL of acetonitrile in a vial and injected into the above solution. The reaction mixture was then allowed to heat at $40°$ C. The solution color started to change from colorless to pink, purple, blue and at this point 14 mL acetonitrile was added to the reaction and the reaction was allowed to run for another 60 min, which resulted in a dark blue solution indicating the formation of nanoprisms with a stable localized surface plasmon resonance dipole peak ($\lambda_{LSPR}$) at 750 nm in acetonitrile (Table 22). At this point, the solution was removed from heat, centrifuged at 7000 rpm for 2 minutes, and used to fabricate LSPR-based sensors. The SEM analysis confirmed an average edge-length of 34 nm. Gold nanoprisms with an average 42 nm ($\lambda_{LSPR}$=800 nm) and 47 nm ($\lambda_{LSPR}$=820 nm) edge-length were synthesized using identical mole ratio of $Et_3PAuCl$ and PMHS, but changing the TOA amount of 0.085 and 0.1 mL, respectively.

Fabrication of LSPR-Based miR-10b Sensors. The gold nanoprisms containing LSPR-based sensors for miR-10b detection were developed using the method described above in Example 1. A tape cleaning procedure was carried out, in order to remove the non-prismatic nanostructures from the coverslips. Adhesive tape was applied to the gold nanoprisms-bound substrate surface, gently pressed down with a finger, and then slowly removed at a 90° angle. the nanoprisms-bound substrates were subjected to overnight incubation in a solution of PBS that contained a 1:1 ratio of 1.0 µM solution of HS-C6-ssDNA-10b and $PEG_6$-SH. Finally, the -S-C6-ssDNA-10b and —S-$PEG_6$ functionalized nanoprisms rinsed with adequate amount of PBS buffer solution to remove nonspecifically bound thiols. These functionalized nanoprisms, which were covalently attached onto supporting substrate and denoted as the LSPR-based sensor, were further utilized for miR-10b detection. We obtained the concentration of miR-10b in each media from the observed $\lambda_{LSPR}$ shift and converted it into the corresponding concentration using the calibration curve derived for miR-10b under various conditions, which include two different physiological media (human plasma and PBS buffer), two different culture media (RPMI and DMEM) and two different growth conditions (normoxia and hypoxia) (see Table 23).

Cell Culture. Stably overexpressing miR-10b and control ASPC-1, BxPC-3, and PANC-1 cells from ATCC (Manassas, VA, USA) were grown in culture at 37° C., 5% $CO_2$ in either RPMI 1640 (AsPC-1 and BxPC-3) or DMEM (PANC-1) with 5% FBS (exosomes depleted) and 1% penicillin/streptomycin as described previously and set forth in Ouyang, H.; Gore, J.; Deitz, S.; Korc, M. miR-10b enhances pancreatic cancer cell invasion by suppressing TIP30 expression and promoting EGF and TGF-[beta] actions. Oncogene 2014, 33, 4664-4674 and incorporated herein by reference in its entirety. Cells were plated in 60 mm dishes at a concentration of $4\times10^5$ and grown in standard conditions (normoxia) for 72 hours. For hypoxic conditions, plates were removed from normoxia at 24 hours post-plating and transferred to a hypoxia chamber at 37° C., 5% $CO_2$, and 1% $O_2$ for 48 hours.

Engineered miR-10b PCCs and RNA Isolation. Cells were stably transduced to overexpress miR-10b with the MDH1-PGK-GFP miR-10b retroviral construct (Addgene plasmid 16070) with packaging plasmids PAX2 and pMD2.G. Sham-transfections to generate control cells were established by transduction with an empty MDH1-PGK-GFP construct (Addgene plasmid 11375) using Phoenix cells for retroviral packaging (Life Technologies). Harvested viruses were used for transduction as previously described (as set forth in Liu, F.; Korc, M. Cdk4/6 Inhibition Induces Epithelial-Mesenchymal Transition and Enhances Invasiveness in Pancreatic Cancer Cells. *Mol. Cancer Ther.* 2012, 11, 2138-2148 and incorporated herein by reference in its entirety) and GFP-positive cells were isolated using flow cytometry 48 hours post-transduction (Flow Cytometry Facility, Indiana University School of Medicine, Indianapolis, IN, USA). Sorted cells were plated and cultured as described above and allowed to recover for 48 hours prior to use in experiments. Validation of continued miR-10b overexpression was confirmed by monitoring GFP fluorescence and miR-10b levels by qRT-PCR. RNA was isolated from cells using TRIzol, or from media using TRIzol LS according to manufacturer's protocol.

Exosome Isolation from Plasma and RNA Isolation. Plasma samples from PDAC, CP, and normal controls (500 µL/sample) were centrifuged at 10,000×g (4° C.) for 30 minutes. Supernatants were transferred to a new tube and subjected to ultracentrifugation at 100,000×g for 70 minutes (4° C.). The supernatant was removed to a new tube for analysis and the pellet was the washed with 1×PBS and ultracentrifugation was repeated. RNA isolation (100 µL/plasma sample) was performed using the TRIzol kit followed by a single-step purification with the Direct-zol RNA MiniPrep kit (Zymo Research).

LSPR-based Quantification of Plasma and Exosomal miR-10b. Plasma (100 µL) from either PDAC or CP patients was diluted with 2.5 mL of PBS buffer. The LSPR-based sensors were incubated overnight and then rinsed with PBS buffer and extinction spectra were collected in PBS buffer to quantify the miR-10b levels. For exosomal miR-10b quantification, 20 µL of the TRIzol isolate was subjected to a single-step purification procedure with Direct-zol, and the sample was diluted with 2.0 mL of PBS buffer and incubated overnight with LSPR-based sensors. In this case, the extinction spectra were collected in PBS buffer. For accurate quantification of miR-10b in each compartment, each PDAC, CP, and normal control sample was assayed twice using a total of 10 sensors.

Spectroscopy and Microscopy Characterization, and qRT-PCR Assay. Absorption and extinction spectra in the range of 300-1100 nm were collected with a Varian Cary 50 Scan UV-visible spectrophotometer using 1 cm quartz cuvette. All the absorbance spectra were collected using 0.3 mL of reaction solution diluted in 2.0 mL of acetonitrile. Acetonitrile was used as a background for these measurements, and the background was run before collecting the absorbance spectra. All extinction spectra were measured in PBS buffer (pH 7.2) at room temperature unless otherwise specified. Here, the blank silanized glass coverslips immersed in PBS buffer were used as background, which was determined before collecting the extinction spectra. All AFM measurements were conducted in air utilizing tapping mode on a Bruker BioScope Catalyst with SSS-NCHR probes (Nanosensors) (tip radius ~2 nm). Images were collected using a tip velocity of 42 N/m over 1-2 uM scan sizes of three to five regions of each samples. All microscopy files were plain fitted and 2D fitted using Gwyddion. RNA was quantitated using the NanoDrop 2000 Spectrophotometer (Thermo) and samples were diluted to 3.0 ng/µL. Samples were converted to cDNA for miRNA-10b and RNU6B using RT primers (Life Technologies) and the TaqMan MiR Reverse Transcription Kit (Life Technologies) according to manufacturer's protocol. Analysis by qRT-PCR was performed using the ViiA 7 Real-Time PCR System (Life Technologies) and fold changes were obtained by normalizing to control, normoxia conditions for each cell line, using the model presented in Pfaffl, 2001. Scanning electron microscopy (SEM) micrograms were acquired using a JEOL-FESEM at 15 kV. The average edge lengths of the nanoprisms were determined from the SEM images using ImageJ software. Approximately 500 nanoprisms were counted to determine the average values. Transmission electron microscopy (TEM) images of the exosomes were collected using Tecnai G212 Bio Twin TEM microscope at 80 kV operating voltage. The TEM images were captured using AMT CCD camera.

Data Processing and Statistical Analysis. Calibration curves using commercially-obtained miR-10b were performed five times independently and all measurements were reported as mean±standard deviation (σ). The maxima of UV-visible extinction spectra were used to determine the $\lambda_{LSPR}$ and the $\Delta\lambda_{LSPR}$ has been derived by taking the difference between the LSPR-based sensor's responses before and after hybridization ($\Delta\lambda_{LSPR}$). The LODs were calculated by measuring the $\Delta\lambda_{LSPR}$ for the blank (mixed -S-PEG6:-SC6-ssDNA-10b functionalized gold nanoprisms) and then obtained the Z (mean+3σ) value. The Z value was converted into the relative concentration using the calibration curve. Briefly, the blank measurement was obtained as the $\Delta\lambda_{SPR}$ response for LSPR-based sensors after incubation in the respective media without any target miR-10b. Calibration curves constructed using commercially-obtained miR-10b in PBS buffer was used to determine the concentration of miR-10b in total RNA extracted from cell lines and exosomes. Culture media, sup-1, and sup-2 containing miR-10b was obtained using RPMI calibration (AsPC-1 and BxPC-3 cells) curves under hypoxia and normoxia conditions. Similar calibration curves were established using DMEM (PANC-1 cells). For patient plasma samples (PDAC, CP, and NC), and Sup-1 and Sup-2 samples, miR-10b concentration was obtained using the miR-10b calibration curve in human plasma. The miR-10b concentrations in total extracted RNA from exosomes isolated from patient plasma were calculated using the PBS buffer calibration curve.

In this example, the following oligonucleotide and miR strands were used: ssDNA-10b (SEQ ID NO: 2); target miR-10b (SEQ ID NO: 4); miR-16 (SEQ ID NO: 5); miR-126 (SEQ ID NO: 6); miR-141 (SEQ ID NO: 7); miR-122 (SEQ ID NO: 8); and miR-10a (SEQ ID NO: 9).

TABLE 21

Nucleic acid sequences used in this Example.

| strand | Name | sequence | MW (kDa) | modification |
|---|---|---|---|---|
| A | ssDNA-10b | 5'-CACAAATTCGGTTCTACAGGGTA-3' | 7.1 | 5'thiol-$C_6$ |
| B | target miR-10b | 5'-UACCCUGUAGAACCGAAUUUGUG-3' | 7.0 | none |
| C | miR-16 | 5'-UAGCAGCACGUAAAUAUUGGCG-3' | 7.1 | none |
| D | miR-126 | 5'-CAUUAUUACUUUUGGUACGCG-3' | 6.3 | none |
| E | miR-141 | 5'-UAACACUGUCUGGUAAAGAUGG-3' | 6.7 | none |
| F | miR-122 | 5'-UGGAGUGUGACAAUGGUGUUUG-3' | 6.8 | none |
| G | miR-10a | 5'-UACCCUGUAGAUCCGAAUUUGUG-3' | 6.9 | none |

TABLE 22

Calibration curve and the limit of detection (LOD) derived for human plasma supplemented with commercially-obtained miR-10b through LSPR-based sensor designed by using various edge lengths of gold nanoprisms.

| $\Delta\lambda_{LSPR}$ (nm)[a] | Edge length (S.D.)[b, c] | Equation from calibration curve | $R^2$ value | Z value (nm) | LOD (fM) |
|---|---|---|---|---|---|
| 750 | 34 (2.6) | Y = 0.6271ln(X) + 8.6786 | 0.97 | 2.44 | 47.5 |
| 800 | 42 (3.5) | Y = 0.5442ln(X) + 10.866 | 0.97 | 2.04 | 0.091 |
| 820 | 47 (4.9) | Y = 0.5333ln(X) + 10.494 | 0.94 | 1.80 | 0.083 |

[a]The LSPR dipole peak position ($\Delta\lambda_{LSPR}$) of gold nanoprisms in acetonitrile.
[b]S.D. represents standard deviation.
[c]At least 500 nanoprisms from two different batches of synthesis were counted to determine the average edge-length.

TABLE 23

Calibration curve and the LODs derived with the commercially-obtained miR-10b through LSPR based sensor developed with ~42 nm edge length nanoprisms in different physiological media under various conditions.

| Physical media | Media condition | Equation from calibration curve | $R^2$ value | Z value (nm) | LOD (aM) |
|---|---|---|---|---|---|
| RPMI | Hypoxia | Y = 0.4035ln(X) + 8.9509 | 0.97 | 1.80 | 20.1 |
|  | Normoxia | Y = 0.4509ln(X) + 9.8236 | 0.94 | 1.50 | 9.61 |
| DMEM | Hypoxia | Y = 0.4086ln(X) + 8.9136 | 0.96 | 1.80 | 27.5 |
|  | Normoxia | Y = 0.4169ln(X) + 9.2527 | 0.94 | 1.80 | 17.2 |
| PBS buffer |  | Y = 0.5105ln(X) + 10.599 | 0.96 | 1.80 | 32.6 |

Structural Parameters of Sensors

Using miR-10b in human plasma as a model detection analyte coupled with ~40 nm edge- length gold nanoprisms for self-assembled sensor fabrication, we unravel how structural parameters-distance and electronic conjugation between the nanoprism surface and first nucleotide, and ssDNA structure-control sensitivity, selectivity, and reproducibility of the self-assembled sensors. This work can be applied to quantification of other miRs and enables researchers to design extremely powerful miR sensors that will open up opportunities for investigating miR properties in disease without the sensitivity constraints of current analytical techniques. The sensors can be adapted to detect other biomolecules such as proteins, peptides, DNA, aptamers, and organic analytes (explosives and narcotics), and to study of conformational change of proteins, and their related dynamics, which cannot be studied by X-ray crystallography.

Figure 15:
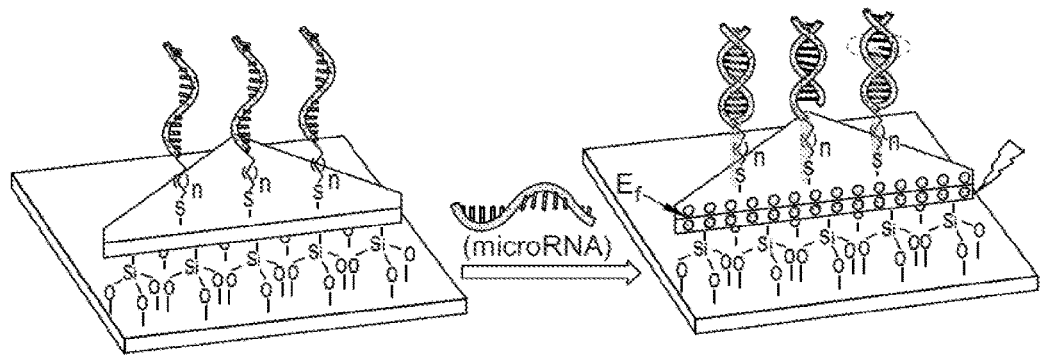
FIG. 15A-15C show various aspects of the plasmonic sensor wherein 15A shows an illustrative depiction of an unbound and bound biosensor wherein when the biosensor is bound to a miR-X the electrons are on top and the holes are underneath the electrons, 15B shows an SEM image of a plurality of plasmonic biosensors, and 15C shows the sequence differences between some exemplary miRs and a ssDNA-10b.
Figure 15:
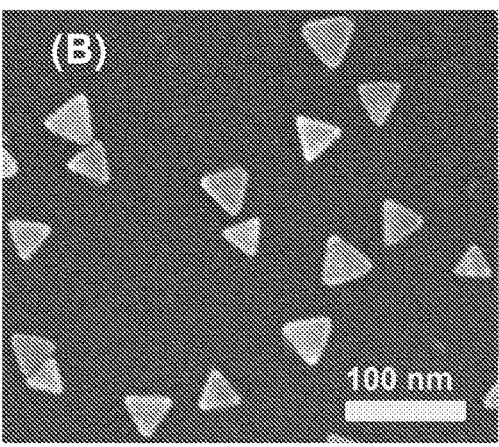

FIG. 15 shows structural parameters of nanoplasmonic sensors modulating the plasmoelectronic effects at the nanoprism and -S-ssDNA/miR interface. (A) Schematic representation of characterizing the delocalization of conduction electron wavefunctions of TNPs into -ssDNA/miR duplex.

(Left panel): the nanoprisms are chemically attached onto a silanized glass substrate and then their surface are functionalized with mixed HS-PEG: $HS(CH_2)_n$-ssDNA-X to prepare LSPR-based nanoplasmonic sensors. (Right panel): Incubation of sensors in miR solution results in formation of -ssDNA/miR duplex. Photo-excitation of TNP results in generation of localized surface plasmon. Wavefunction of conduction electrons (surface plasmon excitation) delocalizes into the -ssDNA/miR duplex (yellow shading) that is manipulated through single base-pair mismatch in the duplex and spacing varying alkyl chain length, $-(CH_2)_n$-, n=3, 6, and 9) between TNP surface and 5'-end of -ssDNA-10b ("linker"). For simplicity $-S-PEG_n$ (n=4 and 6) spacer is not showing. The image is not to scale. (B) Scanning electron microscopy image of ~42 nm edge-length and ~8 nm height the nanoprisms attached onto silanized glass substrate used for nanoplasmonic sensors fabrication. (C) Depiction of -ssDNA-10b and miR molecules used in the studies to investigate conduction electrons wavefunction delocalization. The red letters represent the position of the single base-pair mismatch in the duplex structure.

Figure 16:
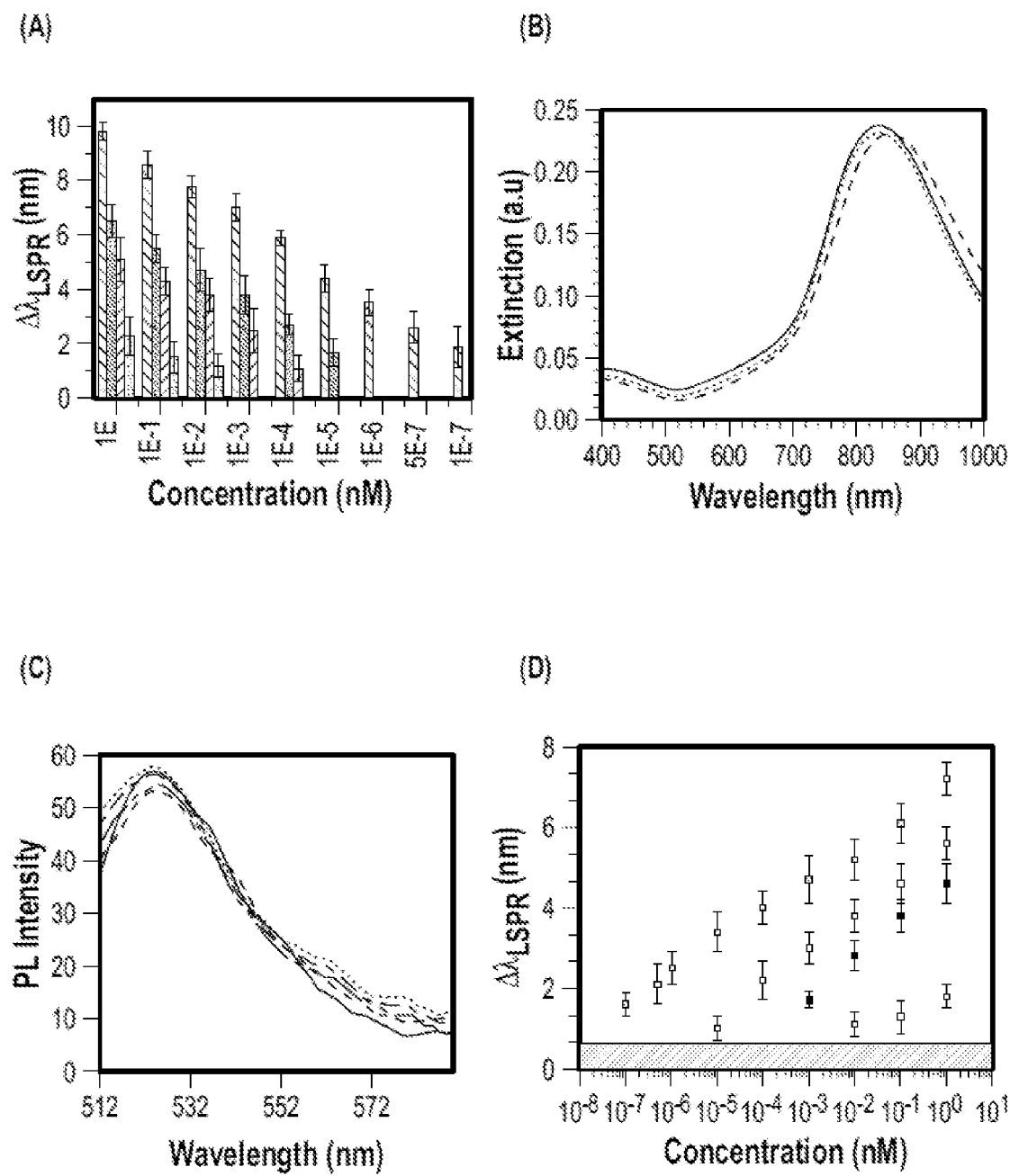
FIG. 16A-16F show graphical representations, wherein 16A illustrates $\Delta\lambda_{LSPR}$ values (nm) for different miRs, 16B shows sensitivity and selectivity of the sensors, 16C shows photoluminescence (PL) spectra for each miR listed in FIGS. 15C, and 16D shows the LOD for fully complementary miR-182, 16E shows the LSPR extinction spectra of —S(CH$_2$)$_6$-ssDNA-10b-functionalized nanoplasmonic sensors in the presence of different miRs with a single base-pair mismatch, and 16F is a graph showing an increase in FWHM of LSPR dipole peak of the nanoprism is observed from 4$^{th}$ to 12$^{th}$ to 18$^{th}$ positions mismatch in -ssDNA-10b/ miR duplex.
Figure 16:
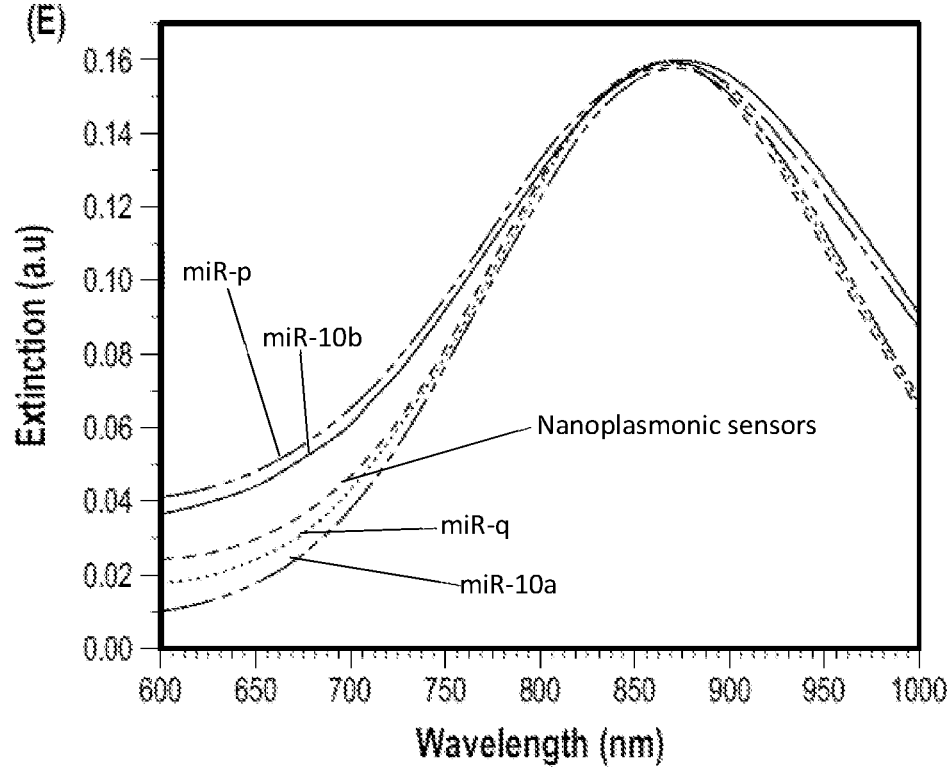
Figure 16:
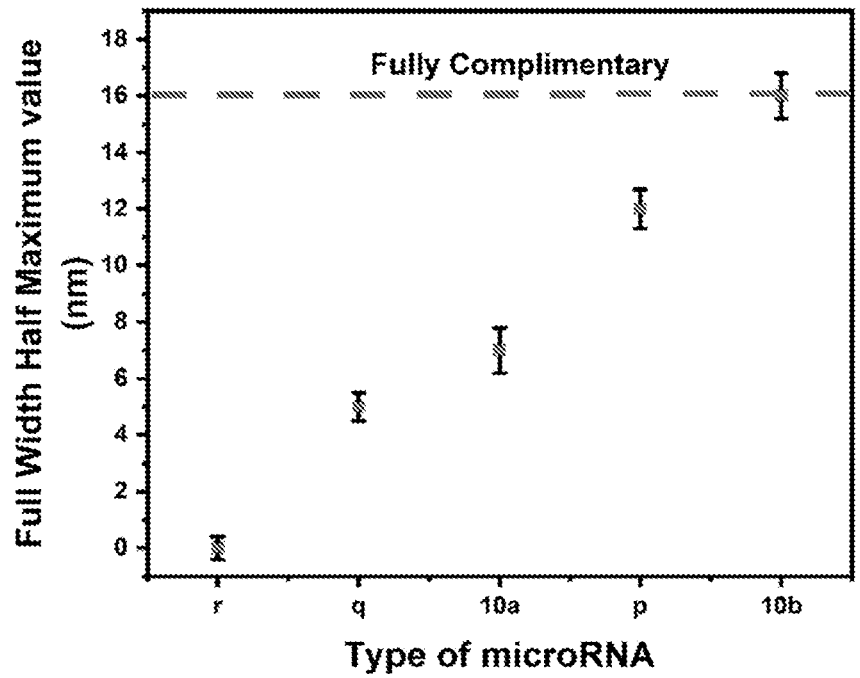

FIG. 16 shows spectroscopy characterization of surface plasmon excitation delocalization by manipulating the structural parameters of miRs. (A) Comparison of miR-10b (first bar with down hashmark (\), miR-p (second bar with dense dots), miR-10a (third bar with up hashmark (/)), and miR-q (fourth bar with light dots) concentration-dependent LSPR response in PBS buffer. For miR-r, no detectable LSPR shift was observed. The sensors were constructed with mixed HS-PEG: $HS(CH_2)_n$-ssDNA-10b. (B) UV-visible extinction spectrum of nanoplasmonic sensors prepared with mixed HS-PEG: $HS(CH_2)_6$-ssDNA-10b (black curve), after incubation with 1.0 nM miR-r (dotted line curve (---)), and then treatment with 15 units of RNase H for 2 h, and then incubation in 1.0 nM miR-10b solution (m-dash curve (-- -- --). All the spectra were collected in PBS buffer. (C) Photoluminescence (PL) spectra of different miRs: miR-10b(-- -- -- curve), miR-p (----- ----- curve), miR-10a (--- --- --- curve), miR-q (----curve), and miR-r (black curve). For this study 5' Fluorescein amidite (FAM) tagged miR were used. PL spectra were collected at 496 nm excitation wavelength. (D) Average $\Delta\lambda_{LSPR}$ value of nanoplasmonic sensors after incubation in different miRs of varying concentrations: miR-182 (highest open squares), miR-s (second highest open squares), miR-t (black squares), and miR-v (lowest open squares). The sensors were constructed with mixed HS-PEG: $HS(CH_2)_n$-ssDNA-182. The shaded bar represents three times the standard deviation of the blank. Concentrations were plotted on the axis in log scale in order to investigate non-specific adsorption at a lower concentration range. (E) UV-visible extinction spectrum of nanoplasmonic sensors for different miRs at 1.0 nM concentration: miR-10b, miR-p, miR-10a, miR-q, and the LSPR spectrum of nanoplasmonic sensors. (F) Measured full-width at half maximum (FWHM) from panel E for different miRs.

LSPR response ($\Delta\lambda_{LSPR}$) of $-S(CH_2)_6$-ssDNA-10b-functionalized nanoplasmonic sensors was determined as a function of concentration (1.0 nM to 100.0 aM) and location of single base-pair mismatch in PBS buffer (wet nanoplasmonic sensors). FIG. 16A illustrates $\Delta\lambda_{LSPR}$ values (nm) for different miRs. Using our published procedure, we calculated LODs for different miRs in buffer and it is 32 aM for miR-10b, while miRs with 18 (miR-p), 12 (miR-10a), and 4 (miR-q) base-pair mismatched display LODs of 5.2 fM, 0.15 µM, and 0.4 nM, respectively. These results support our above-mentioned hypothesis that the LSPR sensitivity of our nanoplasmonic sensor decreases as the mismatch is closer to the surface of the nanoprisms, because when there is a mismatch, the wavefunction of conduction electrons of TNPs are not able to delocalize throughout the duplex -ssDNA/miR structure. Thus, with mismatch the width of plasmon excitation does not increase (consider the nanoprism to be a plasmonic slab in which the height is the smallest dimension along which the incident electromagnetic wave is polarized).

Most strikingly, miR-r in which the first three nucleotides are completely missing from the 3' end but is fully complementary to -ssDNA-10b for the remaining 20 nucleotides does not display any observable $\Delta\lambda_{LSPR}$ values. The same nanoplasmonic sensor was then treated with RNaseH enzyme to regenerate the sensor and incubated in 1.0 nM solution of miR-10b. We observe ~10 nm $\Delta\lambda_{LSPR}$ shifts, suggesting appropriate sensitivity and selectivity of the sensors (FIG. 16B). If the underlying physical property of greatest significance was the change in local dielectric environment of nanoprisms, we would expect a large influence on LSPR-properties when miR-r formed its duplex with the LSPR-sensor (-ssDNA-10b) and would expect it to induce a large $\lambda_{LSPR}$ red-shift. The attachment of miR-r to the sensor was confirmed by fluorescence study described below. The experimental data are remarkable and suggest that our sensing mechanism is most likely controlled by the delocalization of conduction electrons wavefunction and an increase in the slab height rather than the influence of dielectric change, which is the traditionally accepted theory of LSPR-based detection and quantification (assay) of biomolecules. Taken together, the specific physicochemical property of the miR enabling delocalization of conduction electron wavefunctions through coupled -ssDNA/miR duplex leading to the zM sensitivity reported.

A single base-pair match in short -ssDNA/miR duplex should not influence their binding constant significantly but one could argue that the observed $\Delta\lambda_{LSPR}$ values for different mismatches are due to the variable number of miRs that are attach onto the nanoplasmonic sensor, and thus the change in local dielectric environment varies between them. We overruled such an argument by quantifying sensor-bound miRs using fluorescence spectroscopy. MiRs were labeled at 5' end with fluorescein amidite (FAM). Nanoplasmonic sensors were prepared with $-S(CH_2)_6$-ssDNA-10b and then incubated in 1.0 nM FAM-labeled miR solution, allowed to hybridized overnight and then each sensor was washed to remove loosely bound miRs. Finally, $-S(CH_2)_6$-ssDNA-10b/miR duplex was released in solution through ligand exchange reaction (see Supporting Information for detailed experimental procedure). FIG. 16C shows photoluminescence (PL) spectra for each miR listed in FIG. 15C in which characteristic PL peak of FAM ~525 nm is observed. Noticeably, PL peak intensity for different miR is within the experimental error. This result is significant because it suggests that the number of miR attached to the sensors is similar irrespective to single base-pair mismatch at different locations in the duplex. Moreover, the refractive index for miR-10b, -10a, -p, and -q should be nearly identical. Therefore, change in the local dielectric environment of TNPs in the presence of different miRs is presumably similar and should provide similar $\Delta\lambda_{LSPR}$ values, as opposed to our experimental data (see FIG. 16A). Based on the LSPR and PL data for different miRs, we alternatively suggest that the unprecedentedly high sensitivity of our nanoplasmonic sensors for detection of miRs arises from the strong perturbation of conduction electron density of the nanoprisms through wavefunction delocalization that substantially affects their LSPR properties, and thus provides a new "plasmoelectronic" phenomenon that has not been demonstrated before with respect to the characterization of LSPR-based transduction mechanisms for assaying short nucleotides.

Figure 19:
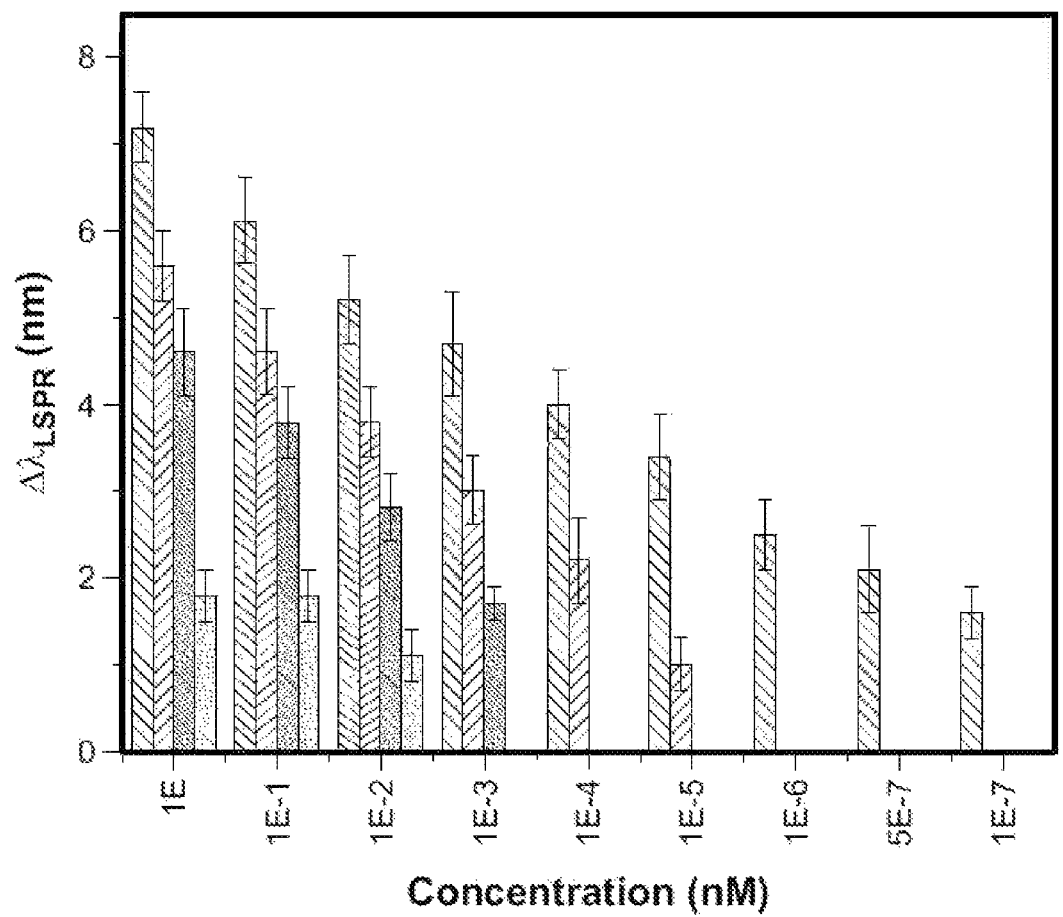
FIG. 19 is a graph showing a comparison of miR-182, miR-s, miR-t, and miR-v concentrations dependent LSPR response in PBS Buffer, wherein the sensors were constructed with mixed—S-PEG$_6$: —S—(CH$_2$)$_6$-ssDNA-182.

In fact, our above-mentioned experimental data provide a guideline for the surface plasmon excitation delocalization-based sensing mechanism: (i) a fully complementary nucleotide sequence is required for extended delocalization of conduction electron wavefunctions throughout the entire -ssDNA/miR duplex and (ii) this transduction mechanism is not controlled by the specific identity of nucleotide in the -ssDNA/miR duplex. To investigate this further, we turned to miR-182, which contains an entirely different nucleotide sequence than miR-10b (Table 24 and 25). There are 22 nucleotides in miR-182 as opposed to 23 in miR-10b, thus a slightly higher delocalization is expected in the latter case. Secondly, miR-182—an oncogenic miR that promotes the metastatic process of bladder cancer-can be used as a biomarker for early detection of BC. We prepared our nanoplasmonic sensor by attaching —S(CH$_2$)$_6$-ssDNA-182 on the nanoprisms, and then incubated it in 1.0 nM miR-182 solution. We observed LSPR red-shifts in the UV-visible absorption spectrum with a $\Delta\lambda_{LSPR}$ value of 7.2 nm. As shown in FIG. 161D, the LOD for fully complementary miR-182 is 82 aM, which is nearly 2.5-fold lower than that of miR-10b. We believe this is related to the overall length of -ssDNA/miR duplex, which influences the extent of delocalization. Finally, nanoplasmonic sensors containing —S(CH$_2$)$_6$-ssDNA-182 were treated with single base-pair mismatch miR-s, -t, and v and the $\Delta\lambda_{LSPR}$ values and LODs (see Table 26 and 27, and FIG. 19 (the bars are presented as first miR-182, miR-s, miR-t, and miR-v)) are in good agreement with the hypothesis of the wavefunctions delocalization process. Taken together, our experimental results show that the transduction mechanism does not depend on the chemical identity of nucleotide in the -ssDNA/miR duplex. Most importantly, the proposed plasmoelectronic phenomenon has allowed us to quantify short noncoding RNAs with a single nucleotide specificity.

TABLE 24

DNA (oligomer) sequences used for this study.

| Name | Sequence | SEQ ID NO: | Modification |
|---|---|---|---|
| -ssDNA-10b | 5' CACAAATTCGGTTCTACAGGGTA 3' | 2 | 5' Thiol-(CH$_2$)$_6$ |
| -SSDNA-182 | 5' TGTGAGTTCTACCATTGCCAAA 3' | 11 | 5' Thiol-(CH$_2$)$_6$ |
| -ssDNA-145 | 5' AGGGATTCCTGGGAAAACTGGAC 3' | 12 | 5' Thiol-(CH$_2$)$_6$ |
| -ssDNA-10b | 5' CACAAATTCGGTTCTACAGGGTA 3' | 13 | 3' Thiol-(CH$_2$)$_3$ |
| -ssDNA-182 | 5' TGTGAGTTCTACCATTGCCAAA 3' | 14 | 3' Thiol-(CH$_2$)$_3$ |
| -ssDNA-145 | 5' AGGGATTCCTGGGAAAACTGGAC 3' | 15 | 3' Thiol-(CH$_2$)$_3$ |
| -ssDNA-143 | 5' CCTCGTCACGACGTAGAGACCA 3' | 16 | 3' Thiol-(CH$_2$)$_3$ |
| -ssDNA-10b | 5' CACAAATTCGGTTCTACAGGGTA 3' | 17 | 5' Thiol C$_6$/iSp(CH$_2$)$_3$ |

TABLE 25 microRNA sequences used for this study.

| Name | Sequence | SEQ ID NO: | Modification |
|---|---|---|---|
| microRNA-10b | 5' UACCCUGUAGAACCGAAUUUGUG 3' | 4 | N/A |
| microRNA-182 | 5' UUUGGCAAUGGUAGAACUCACA 3' | 18 | N/A |
| microRNA-145 | 5' GUCCAGUUUUCCCAGGAAUCCCU 3' | 19 | N/A |
| microRNA-143 | 5' GGUGCAGUGCUGCAUCUCUGGU 3' | 20 | N/A |
| microRNA-p: 18$^{th}$ mismatch in 10b sequences | 5' UACCCGGUAGAACCGAAUUUGUG 3' | 21 | N/A |
| microRNA-10a: 12$^{th}$ mismatch in 10b sequences | 5' UACCCUGUAGAUCCGAAUUUGUG 3' | 9 | N/A |
| microRNA-q: 4$^{th}$ mismatch in 10b sequences | 5' UACCCUGUAGAACCGAAUUCGUG 3' | 22 | N/A |
| microRNA-r: first 3 nucleotides missing in 10b sequences | 5' UACCCUGUAGAACCGAAUUU 3' | 23 | N/A |
| microRNA-s: 18$^{th}$ mismatch in 182 sequences | 5' UUUGACAAUGGUAGAACUCACA 3' | 24 | N/A |

TABLE 25-continued microRNA sequences used for this study.

| Name | Sequence | SEQ ID NO: | Modification |
|---|---|---|---|
| microRNA-t: $12^{th}$ mismatch in 182 sequences | 5' UUUGGCAAUGAUAGAACUCACA 3' | 25 | N/A |
| microRNA-v: $4^{th}$ mismatch in 182 sequences | 5' UUUGGCAAUGGUAGAACUAACA 3' | 26 | N/A |
| microRNA-w: first 3 nucleotides missing in 182 sequences | 5' UUUGGCAAUGGUAGAACUC 3' | 27 | N/A |

TABLE 26

Calculated LOD values for —S—$(CH_2)_6$-ssDNA-10b (182) functionalized nanoplasmonic sensors for various microRNAs in PBS buffer. —S-$PEG_6$ was used as spacers.

| Alkyl Chain | MiR type | Mismatch position | Equation from calibration curve | $R^2$ value | Z value (nm) | LOD (aM) |
|---|---|---|---|---|---|---|
| —$(CH_2)_6$ | 10b | Fully complimentary | y = 0.5105ln(x) + 10.599 | 0.96 | 1.80 | 32.6 |
| —$(CH_2)_6$ | p | $18^{th}$ | y = 0.4132ln(x) + 6.5286 | 0.99 | 1.5 | 5.2E3 |
| —$(CH_2)_6$ | 10a | $12^{th}$ | y = 0.3605ln(x) + 5.17 | 0.96 | 2.0 | 1.5E5 |
| —$(CH_2)_6$ | q | $4^{th}$ | y = 0.2389ln(x) + 2.2167 | 0.94 | 2.0 | 4.0E8 |
| —$(CH_2)_6$ | r | First-3 nucleotides removed | — | — | — | — |
| —$(CH_2)_6$ | 182 | Fully complimentary | y = 0.3301ln(x) + 6.9855 | 0.99 | 1.6 | 82 |
| —$(CH_2)_6$ | s | $18^{th}$ | y = 0.3847ln(x) + 5.581 | 0.99 | 1.8 | 5.4E4 |
| —$(CH_2)_6$ | t | $12^{th}$ | Y = 0.4213ln(x) + 4.68 | 0.80 | 2.3 | 3.5E6 |
| —$(CH_2)_6$ | v | $4^{th}$ | y = 0.152ln(x) + 1.75 | 0.94 | 2.5 | 1.4E11 |
| —$(CH_2)_6$ | w | First-3 nucleotides removed | — | — | — | — |

TABLE 27

$\Delta\lambda_{LSPR}$ responses from LSPR based sensors of microRNA-10b and microRNA-182 for complimentary, $18^{th}$, $12^{th}$, $4^{th}$ mismatches, and 3 nucleotides missing in PBS buffer.

| Alkyl Chain | Type of microRNA | microRNA Concentration (nM) | Average $\Delta\lambda_{LSPR}$ (nm) | Standard Deviation (nm) |
|---|---|---|---|---|
| —$(CH_2)_6$ | 10b | 1.0 | 9.8 | 0.3 |
| | | 0.1 | 8.6 | 0.5 |
| | | 0.01 | 7.8 | 0.4 |
| | | 0.001 | 7.0 | 0.5 |
| | | 0.0001 | 5.9 | 0.3 |
| | | 0.00001 | 4.4 | 0.5 |
| | | 0.000001 | 3.5 | 0.5 |
| | | 0.0000005 | 2.6 | 0.6 |
| | | 0.0000001 | 1.9 | 0.7 |
| —$(CH_2)_6$ | p | 1.0 | 6.5 | 0.6 |
| | | 0.1 | 5.5 | 0.5 |
| | | 0.01 | 4.7 | 0.5 |
| | | 0.001 | 3.8 | 0.4 |
| | | 0.0001 | 2.7 | 0.4 |
| | | 0.00001 | 1.7 | 0.5 |
| —$(CH_2)_6$ | 10a | 1.0 | 5.1 | 0.6 |
| | | 0.1 | 4.3 | 0.5 |
| | | 0.01 | 3.8 | 0.6 |
| | | 0.001 | 2.5 | 0.5 |
| | | 0.0001 | 1.1 | 0.3 |
| —$(CH_2)_6$ | q | 1.0 | 2.3 | 0.5 |
| | | 0.1 | 1.5 | 0.6 |
| | | 0.01 | 1.2 | 0.4 |
| —$(CH_2)_6$ | r | 1.0 | 0 | 0.3 |
| —$(CH_2)_6$ | 182 | 1.0 | 7.2 | 0.4 |
| | | 0.1 | 6.1 | 0.5 |
| | | 0.01 | 5.2 | 0.5 |
| | | 0.001 | 4.7 | 0.6 |
| | | 0.0001 | 4.0 | 0.4 |
| | | 0.00001 | 3.4 | 0.5 |
| | | 0.000001 | 2.5 | 0.4 |
| | | 0.0000005 | 2.1 | 0.5 |
| | | 0.0000001 | 1.6 | 0.3 |
| —$(CH_2)_6$ | s | 1.0 | 5.6 | 0.4 |
| | | 0.1 | 4.6 | 0.5 |
| | | 0.01 | 3.8 | 0.4 |
| | | 0.001 | 3.0 | 0.4 |
| | | 0.0001 | 2.2 | 0.5 |
| | | 0.00001 | 1.0 | 0.3 |

TABLE 27-continued $\Delta\lambda_{LSPR}$ responses from LSPR based sensors of microRNA-10b and microRNA-182 for complimentary, 18$^{th}$, 12$^{th}$, 4$^{th}$ mismatches, and 3 nucleotides missing in PBS buffer.

| Alkyl Chain | Type of microRNA | microRNA Concentration (nM) | Average $\Delta\lambda_{LSPR}$ (nm) | Standard Deviation (nm) |
|---|---|---|---|---|
| —(CH$_2$)$_6$ | t | 1.0 | 4.6 | 0.5 |
|  |  | 0.1 | 3.8 | 0.4 |
|  |  | 0.01 | 2.8 | 0.4 |
|  |  | 0.001 | 1.7 | 0.2 |
| —(CH$_2$)$_6$ | v | 1.0 | 1.8 | 0.3 |
|  |  | 0.1 | 1.3 | 0.4 |
|  |  | 0.01 | 1.1 | 0.3 |
| —(CH$_2$)$_6$ | w | 1.0 | 0 | 0.2 |

Figure 17:
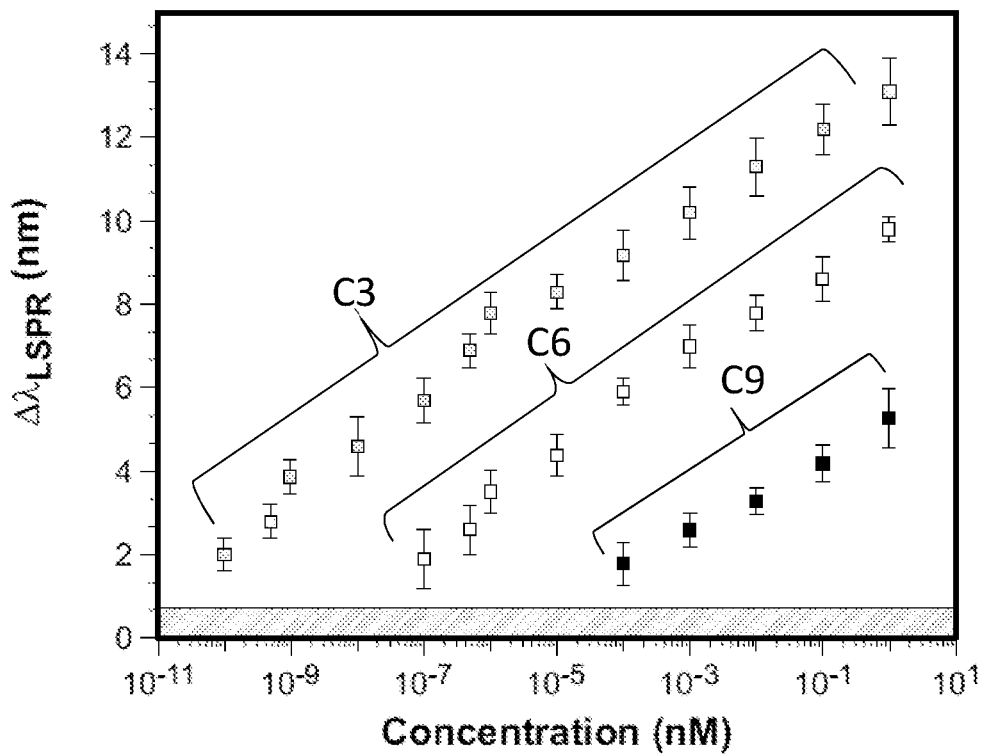
FIG. 17A-17B show graphical representations, wherein 17A illustrates the average $\Delta\lambda_{LSPR}$ values for three different linkers as a function of miR-10b concentration, and 17B shows the observed highest (21 nm) and lowest (10 nm) FWHM values for various linker lengths (i.e., —(CH$_2$)$_3$ and —(CH$_2$)$_9$) linker, respectively.
Figure 17:
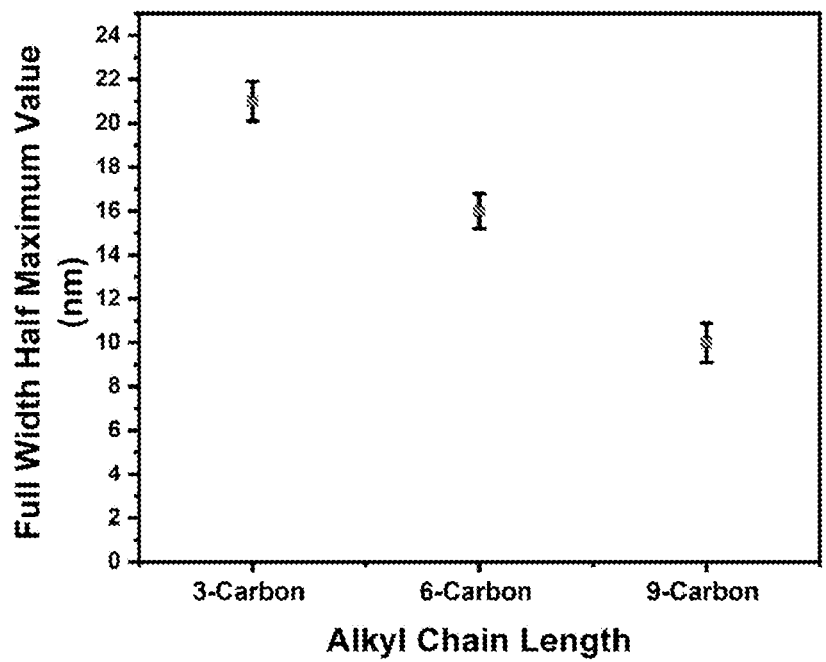

FIG. 17 shows characterization of the linker's role on conduction electron wavefunction delocalization. (A) Average $\Delta\lambda_{LSPR}$ value of nanoplasmonic sensors, which were prepared with three different spacers, —(CH$_2$)$_3$-(top squares), —(CH$_2$)$_6$-(middle squares), and —(CH$_2$)$_9$-(black squares) as a function of miR-10b concentration. Each spacer was connected with -ssDNA-10b as a recognition molecule for miR-10b. The shaded bar represents three times the standard deviation of the blank. Concentrations were plotted on the axis in log scale in order to investigate non-specific adsorption at a lower concentration range. (B) Measured FWHM for different alkyl chain length for 1.0 nM miR-10b concentrations.

Figure 18:
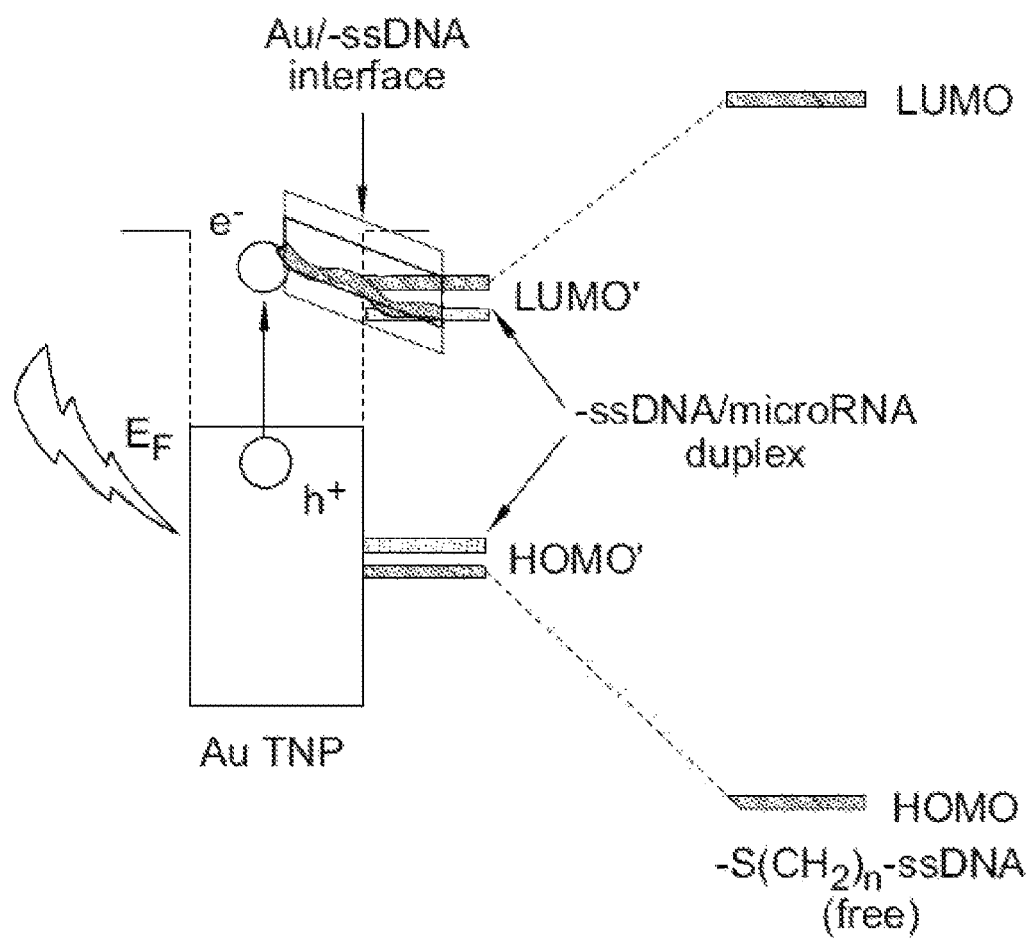
FIG. 18 shows a schematic representation of proposed plasmon excitation delocalization at the nanoprism and —S(CH$_2$)$_n$-ssDNA/miR interface.

FIG. 18 shows a schematic representation of proposed plasmon excitation delocalization at the nanoprism and —S(CH$_2$)$_n$-ssDNA/miR interface. Attachment of —S(CH$_2$)$_n$-ssDNA onto Au induces hybridization of electronic states and creates hybrid bonding (HOMO') and antibonding (LUMO') orbitals. The HOMO'-LUMO' gap further reduces after formation of -ssDNA/miR duplex.[49] The LUMO' further facilitates photo-excited conduction electron (plasmon excitation) wavefunction delocalization (wavy line) from the nanoprism to the -ssDNA/miR moiety. The extended pi-stacking in -ssDNA/miR duplex facilitate the wavefunction delocalization. Delocalization reduces the electron density of TNP and red-shifts the LSPR dipole peak. The image is not to scale.

Comparison of Linker Length and Mismatch Position

The linker length can affect delocalization of conduction electrons of gold nanoprisms into the duplex formed between the ssDNA and the target miR. The linker length can vary between about 3 carbons and 9 carbons, while maintaining all other structural attributes and fabrication techniques of the sensor. No significant influence on charge delocalization in the sensors is expected when linkers have more than 9 carbons (i.e., C9-ssDNA-miR) because the approximately 25 nm decay length for ~42 nm gold nanoprisms is much longer than C9-ssDNA-miRx.

Figure 20:
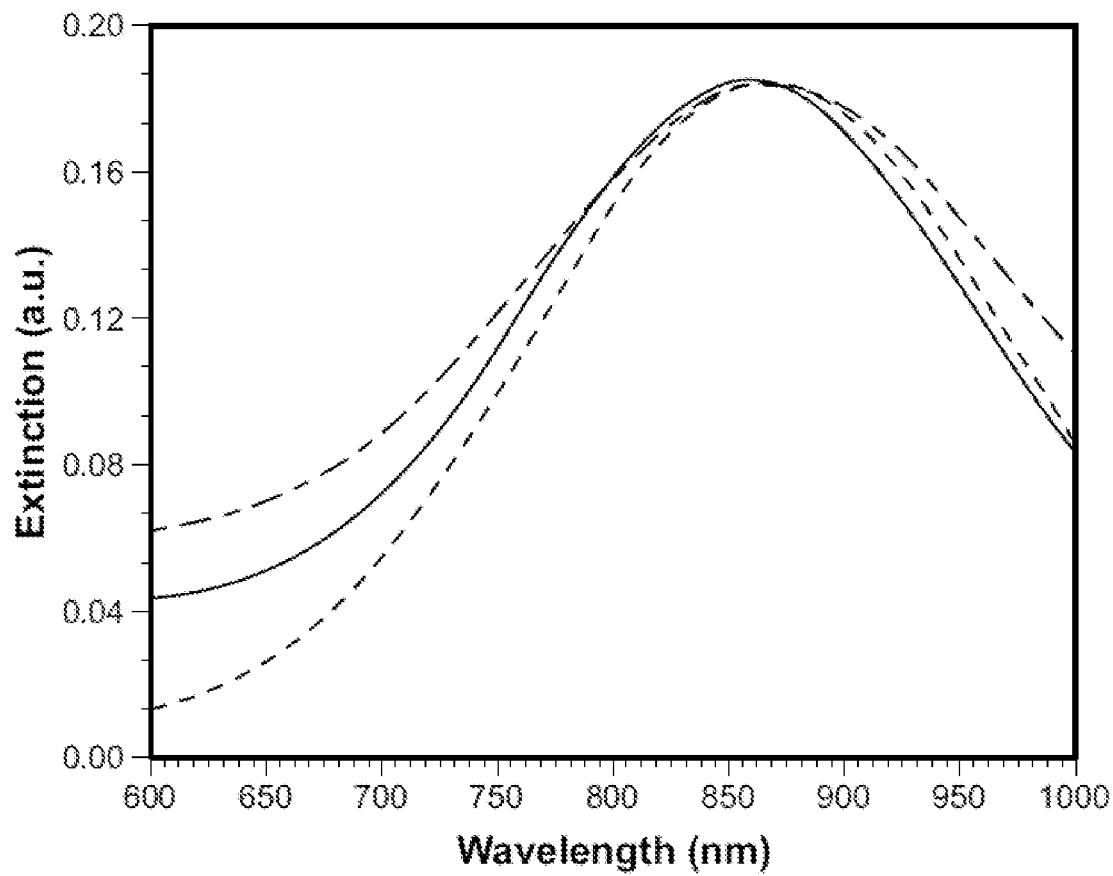
FIG. 20 is a graph showing UV-visible extinction spectrum of nanoplasmonic sensors prepared with three different spacers, —(CH$_2$)$_3$-(--- ---curve), —(CH$_2$)$_6$-(---- curve) and —(CH$_2$)$_9$-(black curve) followed by incubation in 1.0 nM microRNA-10b. All the spectra were collected in PBS buffer (pH=7.2).

The Impact upon Conduction Electron Wavefunction Delocalization of Linker Length Between Gold Triangular Nanoprisms and -ssDNA. Nanoplasmonic sensors were prepared by attaching -ssDNA-10b onto gold triangular nanoprisms via-(CH$_2$)$_6$ linkers. -ssDNA-10b was used as a model receptor for miR-10b quantification in PBS buffer, while keeping other nanoplasmonic sensor fabrication parameters identical. The linker facilitates homogeneous packing of -ssDNAs onto the surface of the nanoprisms and avoids coiling. The linker chain length was varied from —(CH$_2$)$_3$ to —(CH$_2$)$_9$, see FIG. 15A. FIG. 17A illustrates the average $\Delta\lambda_{LSPR}$ values for three different linkers as a function of miR-10b concentration. The LODs for —(CH$_2$)$_3$ and —(CH$_2$)$_9$ are 137 zeptomolar (zM) and 0.81 µM, respectively (see Table 28 and 29, and FIG. 17). We also attached a —(CH$_2$)$_{16}$ linker but no noticeable $\Delta\lambda_{LSPR}$ was observed (data not shown). Strikingly, nanoplasmonic sensors constructed with —S(CH$_2$)$_3$-ssDNA-10b exhibited nearly 240-fold higher sensitivity than that of —S(CH$_2$)$_6$-ssDNA-10b. We concluded that the high sensitivity of nanoplasmonic sensors constructed with —(CH$_2$)$_3$-ssDNA-10b arose due to improved delocalization of conduction electrons wavefunction of the nanoprisms into -ssDNA/miR duplex that arose when the insulating barrier between the nanoprism and duplex was reduced. Without intending to be bound by theory, we believe that the shorter alkyl chain length creates a thinner insulating barrier and increases the conduction electron wavefunction delocalization into the -ssDNA/miR duplex, which results in a larger shift in $\Delta\lambda_{LSPR}$ and higher sensitivity. Finally, we observed the highest (21 nm) and lowest (10 nm) FWHM values for —(CH$_2$)$_3$ and —(CH$_2$)$_9$ linker, respectively (FIG. 17B and FIG. 20). This trend also supports our surface plasmon excitation delocalization mechanism.

TABLE 28

Calculated LOD values of LSPR based sensors, which were made using various alkyl chain length linkers, —(CH$_2$)$_3$, —(CH$_2$)$_6$, and —(CH$_2$)$_9$

| Alkyl Chain | Type of miR | Media Condition | Equation from calibration curve | $R^2$ value | Z value (nm) | LOD (aM) |
|---|---|---|---|---|---|---|
| —(CH$_2$)$_3$ | 10b | PBS Buffer | y = 0.4772ln(x) + 13.506 | 0.99 | 2.67 | 0.137 |
| —(CH$_2$)$_6$ | 10b | PBS Buffer | y = 0.5105ln(x) + 10.599 | 0.96 | 1.80 | 32.6 |
| —(CH$_2$)$_9$ | 10b | PBS Buffer | y = 0.3735ln(x) + 5.16 | 0.99 | 2.5 | 8.1E5 |

TABLE 29

Calculated LOD values of LSPR sensors, which were made using various alkyl chain length linker, —(CH$_2$)$_3$, —(CH$_2$)$_6$, and —(CH$_2$)$_9$ in PBS buffer.

| Alkyl Chain | Type of miR | miR Concentration (nM) | Average $\Delta\lambda_{LSPR}$ (nm) | Standard Deviation (nm) |
|---|---|---|---|---|
| —(CH$_2$)$_3$ | 10b | 1.0 | 13.1 | 0.8 |
|  |  | 0.1 | 12.2 | 0.6 |
|  |  | 0.01 | 11.3 | 0.7 |
|  |  | 0.001 | 10.2 | 0.6 |
|  |  | 0.0001 | 9.2 | 0.6 |
|  |  | 0.00001 | 8.3 | 0.4 |
|  |  | 0.000001 | 7.8 | 0.5 |
|  |  | 0.0000005 | 6.9 | 0.4 |

TABLE 29-continued

Calculated LOD values of LSPR sensors, which were made using various alkyl chain length linker, —(CH$_2$)$_3$, —(CH$_2$)$_6$, and —(CH$_2$)$_9$ in PBS buffer.

| Alkyl Chain | Type of miR | miR Concentration (nM) | Average $\Delta\lambda_{LSPR}$ (nm) | Standard Deviation (nm) |
|---|---|---|---|---|
| —(CH$_2$)$_6$ | 10b | 0.0000001 | 5.7 | 0.5 |
| | | 0.00000001 | 4.6 | 0.7 |
| | | 0.000000001 | 3.9 | 0.4 |
| | | 0.0000000005 | 2.8 | 0.4 |
| | | 0.0000000001 | 2.0 | 0.4 |
| —(CH$_2$)$_9$ | 10b | 1.0 | 9.8 | 0.3 |
| | | 0.1 | 8.6 | 0.5 |
| | | 0.01 | 7.8 | 0.4 |
| | | 0.001 | 7.0 | 0.5 |
| | | 0.0001 | 5.9 | 0.3 |
| | | 0.00001 | 4.4 | 0.5 |
| | | 0.000001 | 3.5 | 0.5 |
| | | 0.0000005 | 2.6 | 0.6 |
| | | 0.0000001 | 1.9 | 0.7 |
| | | 1.0 | 5.3 | 0.7 |
| | | 0.1 | 4.2 | 0.4 |
| | | 0.01 | 3.3 | 0.3 |
| | | 0.001 | 2.6 | 0.4 |
| | | 0.0001 | 1.8 | 0.5 |

Figure 21:
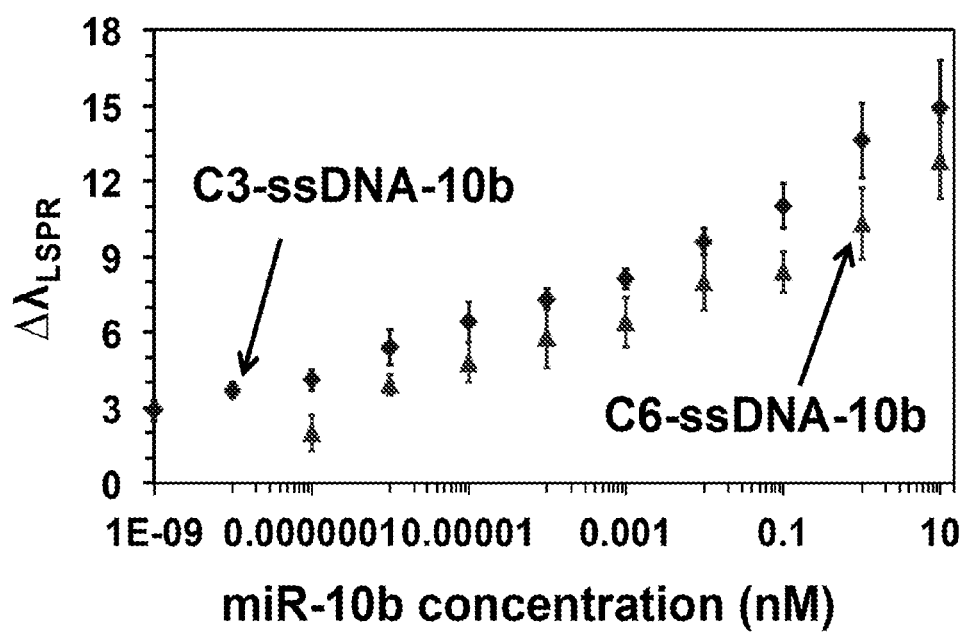
FIG. 21 is a graph showing a difference when the linker lengths of 3 and 6 carbons were compared, a greater LSPR red shift was observed in miR-10b sensors compared to linker length of 9.

When the linker lengths of 3 and 6 carbons were compared, a greater LSPR red shift was observed in miR-10b sensors having the shorter carbon linkers, as shown in FIG. 21, wherein average shift of two different LSPR-based sensors as a function of miR-10b concentration in human plasma is depicted as triangles and diamonds represent LSPR response from the sensors fabricated with HS-PEG6:HS-C6-ssDNA-10b and HS-PEG6:HS-C3-ssDNA-10b, respectively. In both cases, a negative control experiment was conducted by incubating a sensor in just human plasma, and no apparent $\Delta\lambda_{LSPR}$ was detected. The average $\Delta\lambda_{LSPR}$ was determined from five independent measurements.

Figure 22:
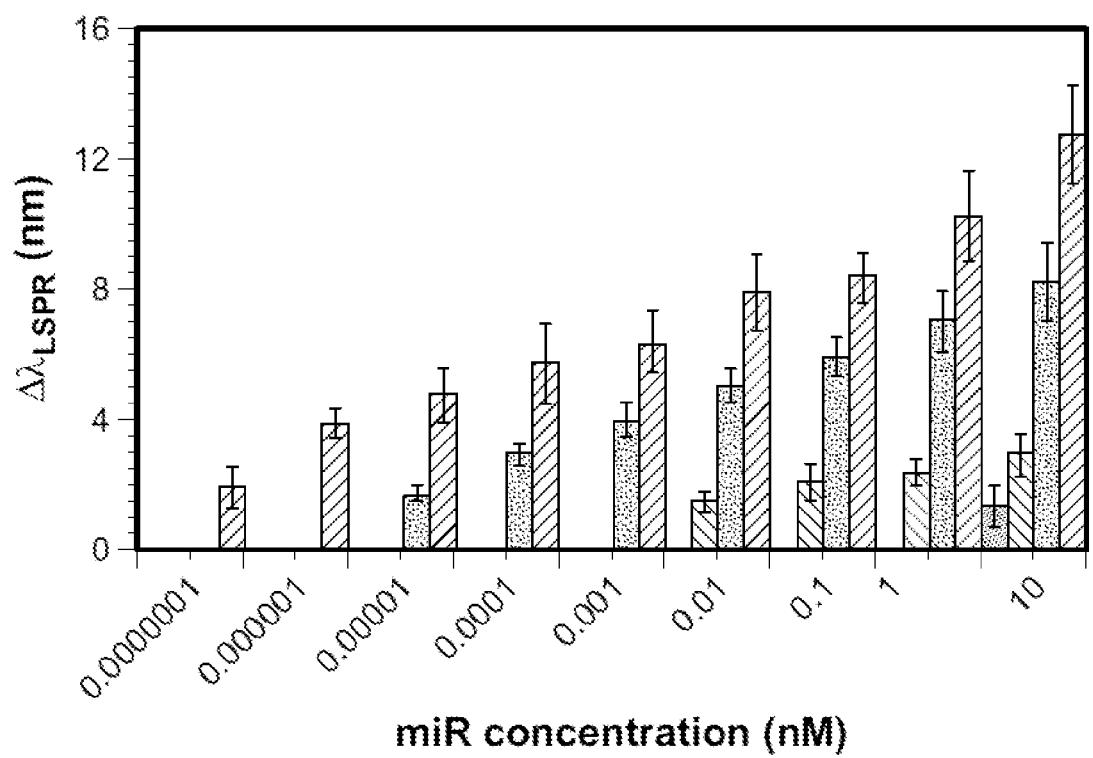

A single base mismatch disrupts the electron flow along the -ssDNA/miR duplex DNA and significantly influences the sensor conductivity and sensitivity. The following study demonstrated that the position of a single base-pair mismatch in the duplex dramatically alters the LSPR properties and detection sensitivity. We evaluated the ability of sensors constructed with mixed HS-PEG6:HS-C6-ssDNA-10b to distinguish between miR-10b and miR-10a which differ by just one nucleotide (miR-10b and miR-10a contain nucleic acid A and U at the 12th position from 5' end, respectively). This LSPR-based sensor displayed a $\Delta\lambda_{LSPR}$ of 2.9 nm in 10 nM miR-10a solution, nearly 4.4 fold lower than the $\Delta\lambda_{LSPR}$ observed for our sensor upon incubation in 10 nM miR-10b solution (see FIG. 22). No detectable $\lambda_{LSPR}$ shift was observed when miR-10a concentration was 1.0 µM or lower. The sensor relies on -ssDNA/miR duplex formation where attachment of miR-10b/10a to nanoprism-bound -ssDNA-10b increases the local dielectric environment and modulates $\Delta\lambda_{LSPR}$. An additional control experiment revealed that nearly all the miR-10a present in solution formed a duplex with the -ssDNA-miR-10b-based LSPR sensor and that a single nucleotide mismatch at the 12th position did not impede miR-10a duplex formation. Our data agree with literature that indicates that single base- pair mismatch in short duplex DNA does not alter the binding constant, so other mechanisms for the decrease in the LSPR-shift are sought to elucidate such unique plasmonic phenomena.

In further studies, nanoplasmonic sensors having six carbon spacers (HS—(CH$_2$)$_6$-ssDNA-10b and PEG$_6$-SH) were hybridized with target miRNAs. Glass coverslips were immersed in a 10% (v/v) aqueous RBS 35 detergent solution at 90° C. for 30 min. After thoroughly rinsing the coverslips with nanopure water, coverslips were placed in a solution of concentrated hydrochloric acid and methanol (1:1 v/v) for 30 min. The coverslips were then rinsed several times with nanopure water and dried in a vacuum oven at 60° C. for at least 24 h prior to use. The dried coverslips were then incubated in a solution of 15% MPTES in N$_2$ purged ethanol for 30 min. The coverslips were then rinsed 3-5 times by sonicating them in N$_2$ purged ethanol for 10 min each time. After rinsing, the coverslips were baked in a vacuum oven at 120° C. for at least 3 h. The prepared MPTES functionalized coverslips (supporting substrates) were then stored at 4° C. Gold triangular nanoprisms (the nanoprisms) were chemically synthesized according to our previously developed procedure with minor modification.[1-4] Specifically, Et$_3$PAu(I)Cl (12.0 mg) was dissolved in 10 mL of acetonitrile and allowed to stir for 5 min at room temperature. Next, 0.085 mL of TOA and 0.3 mL of PMHS were mixed with 1.0 mL of acetonitrile and injected into the gold salt solution at room temperature. The solution temperature was then raised to 42-44° C. and maintained during the entire synthesis. During the heating, the solution color started to change from colorless to pink, purple, and then light blue. Once it turned a light blue color, 7.0 mL of additional acetonitrile was added to the reaction and the reaction was allowed to run until it resulted in a dark blue solution indicating the formation of the nanoprisms with a stable localized surface plasmon resonance (LSPR) dipole peak ($\lambda_{LSPR}$) at 800 nm in acetonitrile. The solution was then removed from heat, and was centrifuged at 5000 rpm for 20 sec. Next, previously prepared MPTES-functionalized coverslips were then incubated for 1.0 h in a freshly synthesized the nanoprisms solution. After incubation, the glass coverslip-attached the nanoprisms were rinsed with acetonitrile, dried under nitrogen flow, and stored under nitrogen at 4° C. The chemically synthesized nanoprisms attached onto the silanized glass coverslips were characterized using scanning electron microscopy (SEM).

A 1.0 nM solution of 5' FAM fluorophore-functionalized miR was used for the complementary (miR-10b), for the single base-pair mismatch miRs (miR-p, miR-10a, and miR-q), and for the miR in which the three starting nucleotides were missing (miR-r) (see FIG. 23 and Table 30). After a 12 h hybridization between the nanoplasmonic sensors and the miRs, the sensors were thoroughly rinsed with PBS buffer, and were then incubated in aqueous 20 MMV mercaptoethanol solution for the overnight ligand exchange reaction. The exchanged solution was collected and centrifuged at 10,000 rpm for 40 min. The solution part was carefully removed and the solid was collected and further dissolved in 1.5 mL of PBS buffer. Absorption and extinction spectra in the range of 300-1100 nm were collected with a Varian Cary 50 Scan UV-visible spectrophotometer using 1 cm quartz cuvettes. All extinction spectra were measured in PBS buffer at room temperature. Here, blank silanized glass coverslips immersed in PBS buffer were used as a background. Approximate concentrations of the fully complementary miRs and the single base-pair mismatch miRs attached to the nanoplasmonic sensor were determined using the procedure reported in the literature.

TABLE 30

The miR sequences used in this study

| Name | Sequence | SEQ ID NO: | Modification |
|---|---|---|---|
| miR-10b | 5' UACCCUGUAGAACCGAAUUUGUG 3' | 4 | N/A |
| miR-182 | 5' UUUGGCAAUGGUAGAACUCACA 3' | 18 | N/A |
| miR-145 | 5' GUCCAGUUUUCCCAGGAAUCCCU 3' | 19 | N/A |
| miR-143 | 5' GGUGCAGUGCUGCAUCUCUGGU3' | 20 | N/A |
| miR-p: 18$^{th}$ mismatch in 10b sequences | 5' UACCCGGUAGAACCGAAUUUGUG 3' | 21 | N/A |
| miR-10a: 12$^{th}$ mismatch in 10b sequences | 5' UACCCUGUAGAUCCGAAUUUGUG 3' | 9 | N/A |
| miR-q: 4$^{th}$ mismatch in 10b sequences | 5' UACCCUGUAGAACCGAAUUCGUG 3' | 22 | N/A |
| miR-r: first 3 nucleotides missing in 10b sequences | 5' UACCCUGUAGAACCGAAUUU 3' | 23 | N/A |
| miR-s: 18$^{th}$ mismatch in 182 sequences | 5' UUUGACAAUGGUAGAACUCACA 3' | 24 | N/A |
| miR-t: 12$^{th}$ mismatch in 182 sequences | 5' UUUGGCAAUGAUAGAACUCACA 3' | 25 | N/A |
| miR-v: 4$^{th}$ mismatch in 182 sequences | 5' UUUGGCAAUGGUAGAACUAACA 3' | 26 | N/A |
| miR-w: first 3 nucleotides missing in 182 sequences | 5' UUUGGCAAUGGUAGAACUC 3' | 27 | N/A |

The $\lambda_{LSPR}$ was obtained by using maxima of the UV-visible extinction spectra, and then $\Delta\lambda_{LSPR}$ was derived by taking the difference between LSPR peak of nanoplasmonic sensors before and after hybridization with target miR. Calibration curves were obtained by plotting $\Delta\lambda_{LSPR}$ vs. miR concentration. Finally, the LOD was determined by using z value (mean+3σ), obtained from six $\Delta\lambda_{LSPR}$ measurements of the sensors incubated in buffer solution without miRs. Concentration of target miRs in patient and normal control samples were determined from the calibration curves developed in human plasma (see Table 31 and 32). We used six $\Delta\lambda_{LSPR}$ values and corresponding concentrations, and then the average concentration was calculated. Each patient sample was independently analyzed twice (two weeks apart).

TABLE 31

Calculated LOD values of LSPR based sensors, which were made using an alkyl chain length linker, [—(CH$_2$)$_3$] in plasma.

| Alkyl Chain | Type of miR | Media Condition | Equation from calibration curve | R$^2$ value | Z value (nm) | LOD (zM) |
|---|---|---|---|---|---|---|
| —(CH$_2$)$_3$ | 10b | Plasma | y = 0.4714ln(x) + 12.956 | 0.9905 | 2.86 | 499 |
| —(CH$_2$)$_3$ | 182 | Plasma | y = 0.4706ln(x) + 13.315 | 0.9889 | 3.4 | 707 |
| —(CH$_2$)$_3$ | 145 | Plasma | y = 0.4844ln(x) + 12.796 | 0.9912 | 2.5 | 587 |
| —(CH$_2$)$_3$ | 143 | Plasma | y = 0.4182ln(x) + 11.176 | 0.9931 | 2.3 | 605 |

TABLE 32

$\Delta\lambda_{LSPR}$ responses obtained from LSPR based sensors, which were made using alkyl chain length linker, [—(CH$_2$)$_3$] in plasma.

| Alkyl Chain | Type of miR | miR Concentration (nM) | Average $\Delta\lambda_{LSPR}$ (nm) | Standard Deviation (nm) |
|---|---|---|---|---|
| —(CH$_2$)$_3$ | 10b | 1.0 | 12.9 | 0.8 |
| | | 0.1 | 11.6 | 0.7 |
| | | 0.01 | 10.7 | 0.8 |
| | | 0.001 | 9.6 | 0.8 |
| | | 0.0001 | 8.5 | 0.7 |
| | | 0.00001 | 7.9 | 0.7 |
| | | 0.000001 | 7.2 | 0.6 |
| | | 0.0000005 | 6.4 | 0.6 |
| | | 0.0000001 | 5.5 | 0.5 |
| | | 0.00000001 | 4.0 | 0.5 |
| | | 0.000000001 | 3.3 | 0.8 |

TABLE 32-continued

Δλ$_{LSPR}$ responses obtained from LSPR based sensors, which were made using alkyl chain length linker, [—(CH$_2$)$_3$] in plasma.

| Alkyl Chain | Type of miR | miR Concentration (nM) | Average Δλ$_{LSPR}$ (nm) | Standard Deviation (nm) |
|---|---|---|---|---|
| | | 0.0000000005 | 2.1 | 0.6 |
| | | 0.0000000001 | 1.8 | 0.5 |
| —(CH$_2$)$_3$ | 182 | 1.0 | 12.9 | 0.8 |
| | | 0.1 | 11.9 | 0.6 |
| | | 0.01 | 11.0 | 0.8 |
| | | 0.001 | 10.4 | 0.7 |
| | | 0.0001 | 9.2 | 0.6 |
| | | 0.00001 | 8.2 | 0.5 |
| | | 0.000001 | 7.6 | 0.7 |
| | | 0.0000005 | 6.1 | 0.6 |
| | | 0.0000001 | 5.7 | 0.6 |
| | | 0.00000001 | 4.9 | 0.8 |
| | | 0.000000001 | 3.5 | 0.4 |
| | | 0.0000000005 | 2.7 | 0.5 |
| | | 0.0000000001 | 2.1 | 0.4 |
| —(CH2)$_3$ | 145 | 1.0 | 12.5 | 0.6 |
| | | 0.1 | 11.7 | 0.5 |
| | | 0.01 | 10.4 | 0.5 |
| | | 0.001 | 9.6 | 0.5 |
| | | 0.0001 | 8.4 | 0.3 |
| | | 0.00001 | 7.5 | 0.4 |
| | | 0.000001 | 6.9 | 0.6 |
| | | 0.0000005 | 5.7 | 0.4 |
| | | 0.0000001 | 4.5 | 0.5 |
| | | 0.00000001 | 3.6 | 0.3 |
| | | 0.000000001 | 3.1 | 0.6 |
| | | 0.0000000005 | 2.4 | 0.5 |
| | | 0.0000000001 | 1.3 | 0.5 |
| —(CH$_2$)$_3$ | 143 | 1.0 | 11.6 | 0.9 |
| | | 0.1 | 9.7 | 0.6 |
| | | 0.01 | 9.1 | 0.8 |
| | | 0.001 | 8.3 | 0.7 |
| | | 0.0001 | 7.2 | 0.9 |
| | | 0.00001 | 6.8 | 0.5 |
| | | 0.000001 | 5.5 | 0.6 |
| | | 0.0000005 | 5.1 | 0.5 |
| | | 0.0000001 | 4.2 | 0.5 |
| | | 0.00000001 | 3.6 | 0.4 |
| | | 0.000000001 | 2.7 | 0.4 |
| | | 0.0000000005 | 2.1 | 0.5 |
| | | 0.0000000001 | 1.4 | 0.4 |

In both experimental and theoretical literature, the linewidth (full-width at half maxima, FWHM) of LSPR peak of metal nanoparticles increases as the physical dimension of a nanoparticle increases. In this context, it might be argued that upon conduction electron wavefunction delocalization, height of the plasmonic slab (e.g., the nanoprism) would increase. Change in height of plasmonic slab should cause a difference in FWHM depending on the extent of delocalization that is controlled by the location of the base-pair mismatch in -ssDNA/miR duplex (see FIG. 15A) that elucidate the delocalization mechanism. FIG. 16E illustrates the LSPR extinction spectra of —S(CH$_2$)$_6$-ssDNA-10b-functionalized nanoplasmonic sensors in the presence of different miRs with a single base-pair mismatch. Indeed, an increase in FWHM of LSPR dipole peak of the nanoprism is observed from 4$^{th}$ to 12$^{th}$ to 18$^{th}$ positions mismatch in -ssDNA-10b/miR duplex (see FIG. 16F). The largest FWHM of 16 nm is observed for the fully complementary -ssDNA-10b/miR-10b duplex. Although our PL analysis unequivocally supports the attachment of miR-r to nanoplasmonic sensors, no noticeable differences in FWHM are observed. Therefore, the higher the delocalization, the greater the height of plasmonic slabs, and consequently the larger the FWHM value.

Identification of More Specific Biomarkers for Early Bladder Cancer (BC) Diagnosis. Because circulating miRs are unusually stable in human biofluids such as serum and plasma, such miRs can serve as diagnostic markers for cancer in a liquid biopsy for early and rapid detection of cancer. Two different types of miRs are of interest in cancer screening:

(i) Oncogenic miRs, which promote tumor development by inhibiting tumor suppressor genes that control either cell differentiation or apoptosis. Oncogenic miRs are overexpressed in different cancer including bladder cancer.

(ii) Tumor suppressor miRs, which prevent tumor development by negatively inhibiting oncogenes that control either cell differentiation or apoptosis. The expression of tumor suppressor miRs is decreased in cancer cells relative to non-cancer cells. Because tumor suppressor miRs levels are low in cancer cells, it is extremely difficult to quantify them with a PCR-based assay. Zeptomolar sensitivity of the described nanoplasmonic sensors provides a unique advantage to assay both oncogenic and tumor suppressor miRs directly in unmodified plasma samples. Here, we present the first label-free assay to compare both oncogenic and tumor suppressor levels between patients with metastatic (MT, n=7), non-metastatic (NMT, n=4) and normal controls (NC, n=4) from crude plasma.

Figure 24:
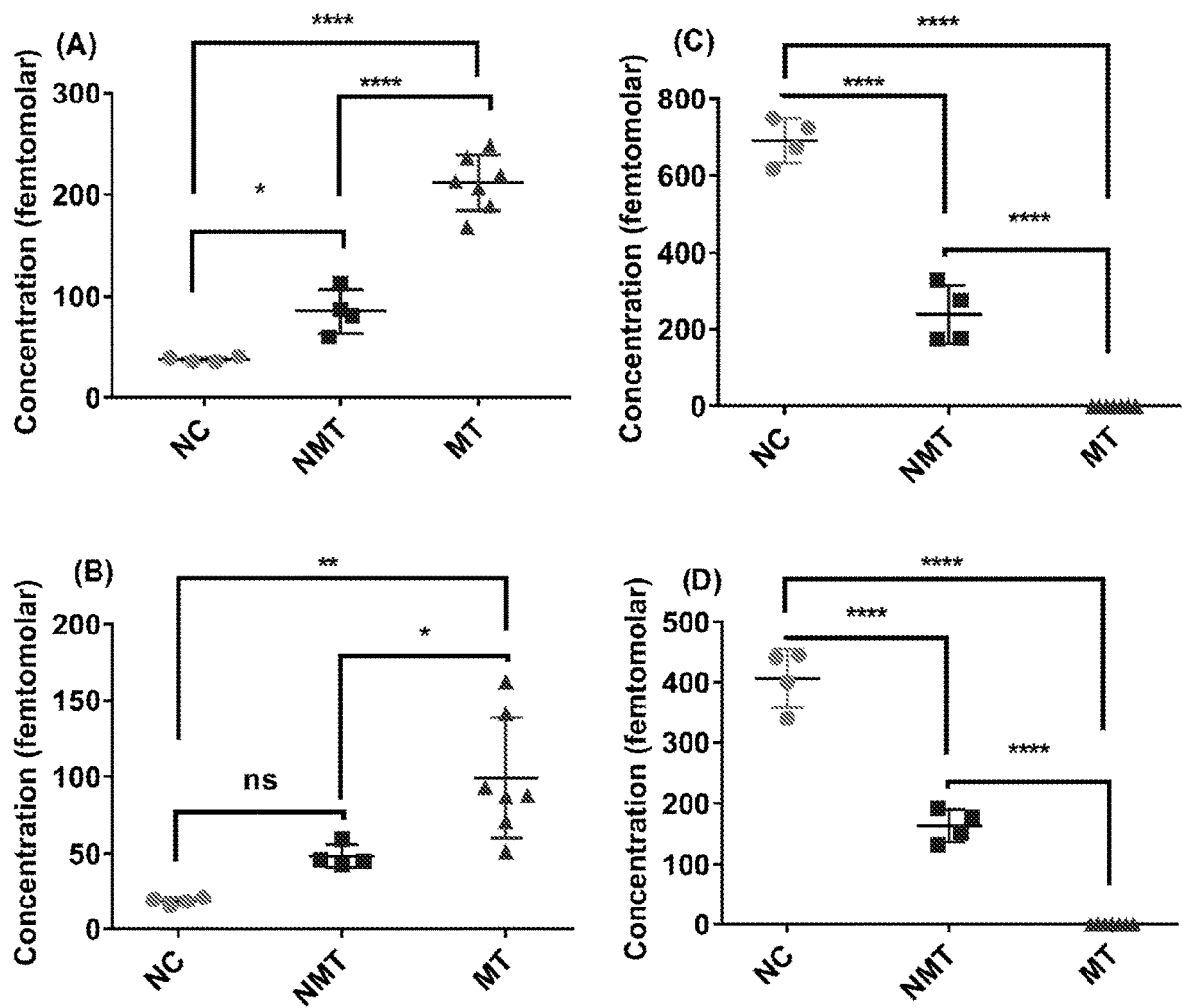
FIG. 24A-24D show statistical representation of microRNA analysis in bladder cancer (metastatic and non-metastatic) patient plasma and normal control subjects. The concentration of oncogenic microRNAs (microRNA-10b and -182) and tumor suppressor microRNAs (microRNA-143 and -145) are determined in different stages of bladder cancer, non-metastasis (NMT) and metastasis (MT), as well as in healthy individuals (normal control, NC); n=4 (NMT), n=7 (MT), n=4 (NC), two experiments for each sample (50 µL/sample) using our nanoplasmonic sensors. (A) microRNA-10b concentration in plasma. (B) Detection of microRNA-182 in plasma. (C) microRNA-143 concentration in plasma. (D) Detection of microRNA-145 in plasma. * $P<0.05$, $P<0.01$, **$P<0.0001$, and ns=not significant by one-way ANOVA.

The current FDA-approved urine cytology test shows poor sensitivity for low-grade lesions and significant disparity in specificity for different BC grades, thus it is a highly unreliable screening test. It is reported that miR-10b and -182 are upregulated in BC, and that miR-143 and -145 are downregulated in BC. Accordingly, these can serve as alternative and more specific biomarkers for early diagnosis of BC. FIG. 24A-D shows the concentration of these four miRs determined directly from unmodified patient plasma using the nanoplasmonic sensors. All seven MT patient samples show high levels of miR-10b (FIG. 24A). Moreover, the levels of NC and NMT patient samples are 8-and 2-fold lower, respectively, as compared to MT samples. These results suggest that while miR-10b is not an ideal biomarker for early BC diagnosis (p <0.05), it can differentiate between MT and NMT disease stages (p<0.0001). On the other hand, miR-182 appears to be a less specific biomarker not only for early diagnosis of BC but also in cancer progression stages (FIG. 24B). Strikingly, miR-143 and -145 levels differ by nearly 3-and 4.0×10$^3$-fold between NC vs. NMT, and NMT vs. MT BC patient samples, respectively (p <0.0001), see FIGS. 24C and D. Moreover, the difference between NC vs. MT is >1.0×10$^4$-fold for tumor suppressor miRs, in contrast to the -6-fold difference observed for oncogenic miRs for the same patient samples. To further validate these results, we tested the specificity of the nanoplasmonic sensors. These tests unequivocally supported a high level of specificity towards the target miRs without false positive responses (selectivity). Taken together, tumor suppressor miRs can serve as more specific biomarkers for early detection of BC and possibly for detecting other cancers as well.

Providing Sensors on Plastic Surfaces

The most promising approach for a non-invasive and high-throughput assay for diagnostic markers in cancer depends on sample-preparation-free detection and quantification of biomarkers in biological fluids. MiRs are overexpressed in various cancers and thus they are the emerging new class of biomarkers for cancer diagnostics. Importantly, point-of-care diagnostics require simultaneous testing of multiple miRs from the same patient to avoid the risk of false diagnosis and to pinpoint the cancer with more specificity. Current state-of-the art assaying techniques (qRT-PCR and microarrays) and other label-free techniques have not demonstrated the ability detect and quantify several circulating miRs directly in biological fluids. To match the robustness of commercial systems for detecting other sorts of analytes (e.g., ELISA) and for additional advantages (e.g., portability, transparent substrate, low-cost, readily scalable, and high-throughput), flexible, inexpensive substrates capable of supporting multiplexed detection are desired.

We here disclose multiplexing devices that utilize the unique LSPR properties of gold nanoprisms to detect and quantify various miRs in plasma, serum, and urine at ultralow concentration, which is beyond the reach of current state-of-the-art technology. The multiplexing devices combine LSPR-based, label-free miR sensing in biological fluids in a multiwell (e.g., 6, 24, 96, 256, 384 wells) assay system by functionalizing plastic surfaces of microwell plates having transparent bottom surfaces to chemically attach nanoprisms onto the surfaces and then functionalizing the nanoprism surfaces with a mixture of ssDNA-free thiolated carbon chain spacers and thiolated ssDNAs complementary to target miRs. Each well contains nanoprisms functionalized with distinct ssDNA probe molecules targeting distinct miRs. Thus, each well can be considered an independent sensor for which $\Delta\lambda_{LSPR}$, can be determined with a standard plate reader in absorption mode. The helix-bound miRs of each sensor can be quantified, as described elsewhere herein. Appropriate control miRs at known concentrations can be placed in the multiplex array to validate accuracy and precision. The multiwall assay system is efficiently improved by applying sensor systems improvements described elsewhere herein to lower the LOD, reduce sample volume, and reduce assay time. This label-free miR sensing platform provides an ultrasensitive, portable, robust, low cost, and high throughput multiplexing assay uses just microliter (μL) amounts of sample for a single sample run. Such a system can provide clearer understanding of tumor heterogeneity by quantifying oncogenic miRs from a single cancer cell. The data below demonstrate the feasibility of multiplexing analysis of oncogenic miRs.

Figure 25:
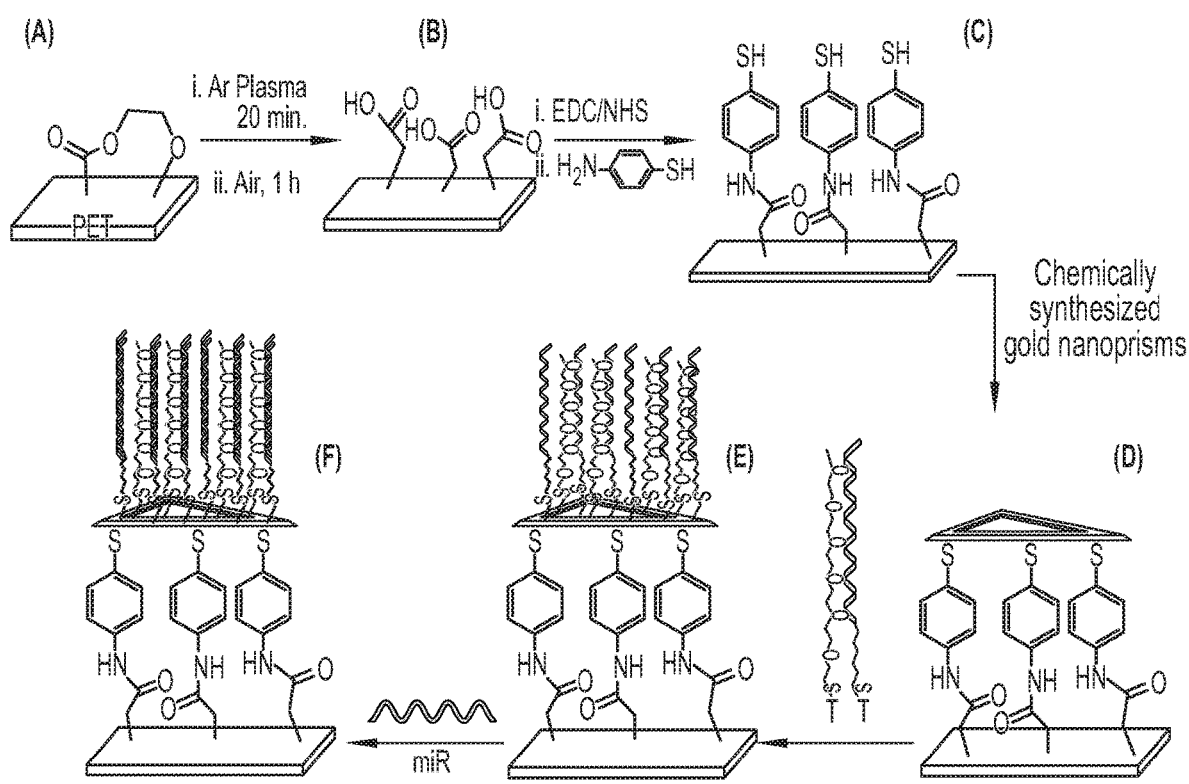
FIG. 25 shows design steps (A)-(F) to produce a plasmonic biosensor.

LSPR-based miR-10b sensors on a poly(ethylene terephthalate) (PET) plastic substrate were constructed as follows: FIG. 25. A. A 0.01 cm thick PET plastic sheet was commercially purchased (Goodfellow Corporation, USA). B. Oxygen containing functional groups were obtained by treating the PET with Ar plasma and then open air. C. Thiol-terminated substrate was prepared by an amide bond (—CONH) formation reaction by incubating B in EDS/NHS solution to activate the acid group and then addition of 1.0 mM 4-aminothiophenol (4-ATP) solution in ethanol (overnight incubation) followed by our functionalization procedure. D. Gold nanoprisms with ~42 nm edge length (yellow triangle) were attached to the plastic substrate by incubating them for 30 min in nanoprism solution. The gold-sulfur bonds are extremely stable, preventing the detachment of nanoprisms from the substrate. E. The nanoprism surface was modified with 1:1 HS-PEG6:HS-C6-ssDNA-10b. F. Addition of miR-10b allows for ssDNA/miR hybridization. We determined the LOD in human plasma, using protocols similar to those described above. Similar functionalization chemistry can be applied to transparent bottom 96 or 384 well PET plates to fabricate multiplexing miR sensors. The thickness of the PET is limited only by its desired durability, and suitability for manipulating and assaying, and can range from about 0.1 mm to about 0.25 mm.

Figure 26:
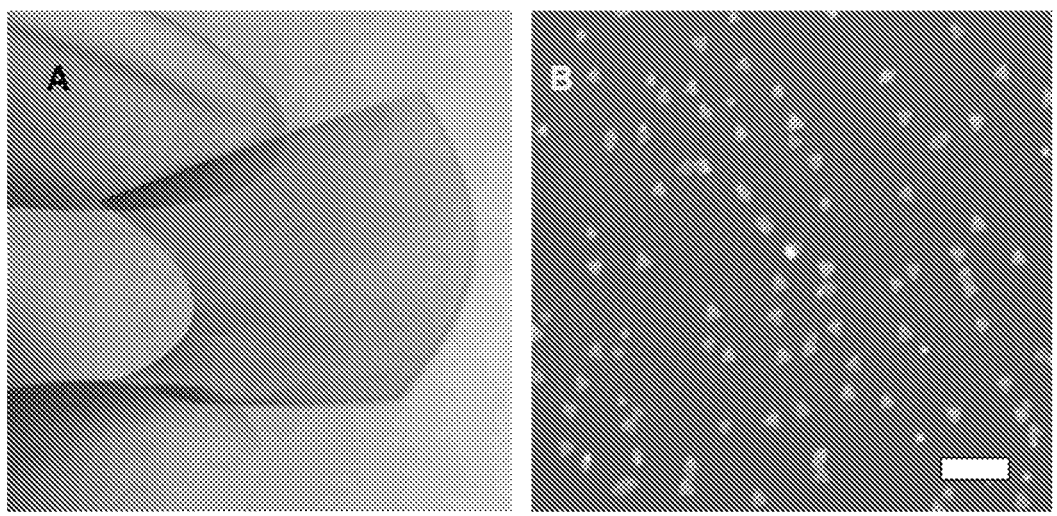
FIG. 26A-26B show the biosensor system, wherein 26A shows a miR-10b plastic sensor, and 26B shows an SEM image depicting the individual plasmonic biosensors on the piece of plastic.

Characterization and Sensitivity of miR-10b Sensor on Plastic Substrate. FIG. 26A shows a miR-10b plastic sensor having surface chemistry similar to FIG. 25E. The standard dimensions of our LSPR-based miR sensor are 2.5 cm length and 0.6 cm wide, which is 25% of the surface area of the sensor shown in FIG. 26A. The functionalized PET substrate is clear. A blue color suggested chemical attachment of nanoprisms onto the surface. We characterized the same sensor by SEM (FIG. 26B) to demonstrate the distribution of gold nanoprisms. Scale bar is 100 nm. The average number of nanoprisms attached to the surface is $125/\mu m^2$. The micrograph shows less density than was observed on a silanized glass substrate. Even so, without optimization, the sensor provided a LOD of 215 aM in human plasma, which is only 2.3 fold higher than the comparable sensor fabricated upon a glass substrate (LOD=91 aM). This LOD value is three orders of magnitude more sensitive than the miR-10b level in pancreatic cancer patients in crude plasma (~200-350 fM). LODs in the zM range using the multiplexing assay to quantify miRs can be achieved.

The density of nanoprisms on PET surface may be lower than on glass because fewer thiol groups may be created upon EDC/NHS coupling using 4-ATP. It is likely that not all acid groups on the PET surface (FIG. 11B) were reacted with 4-ATP because benzene is bulky and creates greater steric repulsion, resulting in fewer thiols on the surface. To achieve higher loading of nanoprisms, amine-terminal long chain alkylthiols such as $H_2N-(CH_2)_6-SH$ (Sigma-Aldrich) can be used instead of 4-ATP to achieve dense and homogeneous surface thiol groups by reducing steric repulsion. Similarly, a higher concentration (2.0-5.0 mM) of $H_2N-(CH_2)_6-SH$ can be employed to maximize amide bond formation with surface acid groups.

Figure 27:
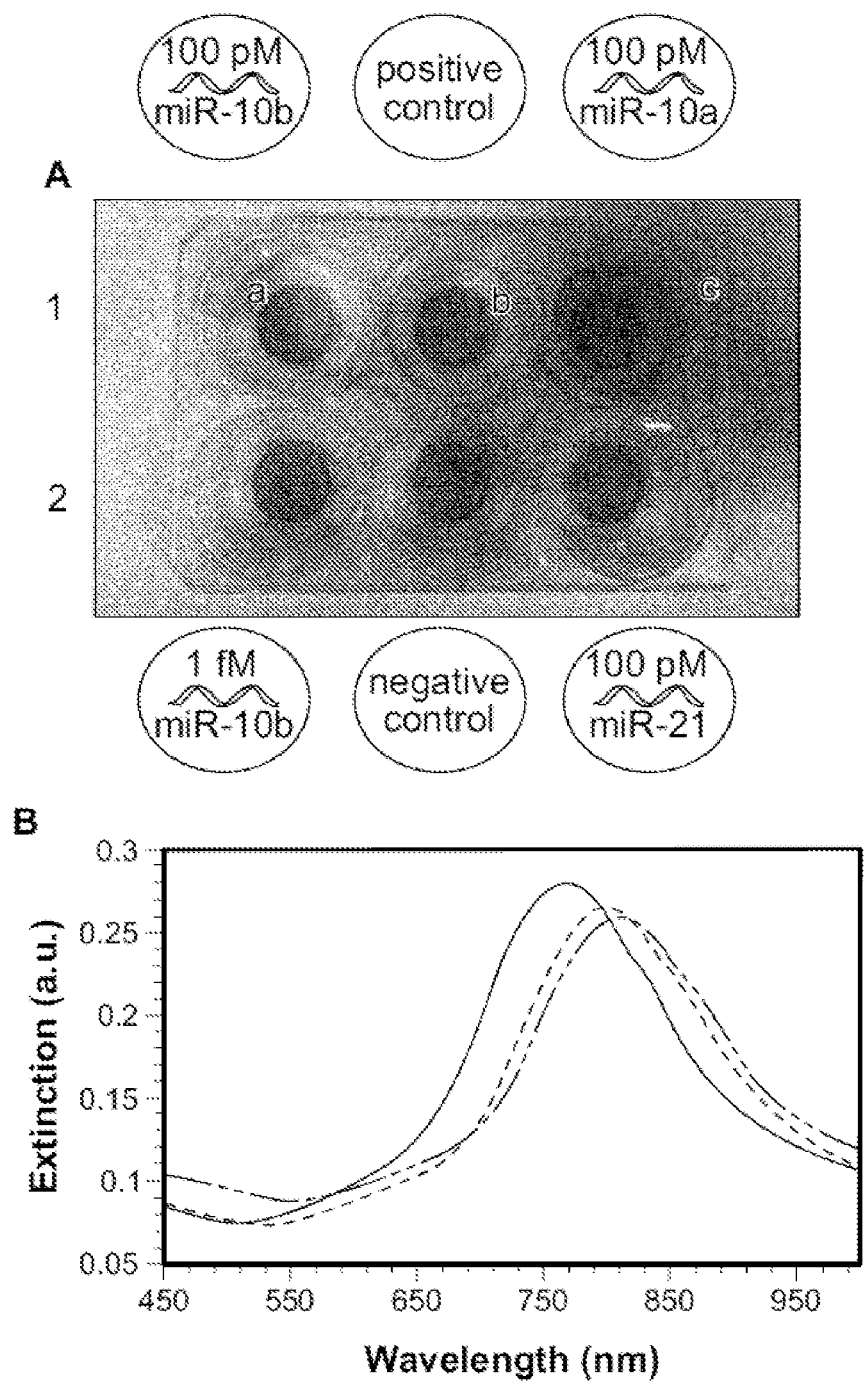
FIG. 27A-27B show the miR biosensors, wherein 27A shows a 6 well plate to which gold nanoprism-based miR sensors were attached, and 27B shows a graphic representation suggesting attachment of miR to form the duplex on the surface of the nanoprisms.

To test the feasibility of multiplexed miR assaying as a proof of concept, LSPR-based nanoprism sensors loaded with three different miRs -- miR-10b, miR-21, and miR-10a -- were prepared in a commercially available 6 well plate with flat glass bottom (24 mm diameter). The glass substrate was silanized to attach gold nanoprisms using published protocols. FIG. 27A shows a 6 well plate (Chemglass, USA) to which gold nanoprism-based miR sensors were attached. 100 μM and 100 aM concentrations were selected for miR-10b because this range is within the typical miR concentration range of pancreatic cancer patients. A 400-μL solution of miR was used to cover the entire glass bottom of the plate (darker gray area), which was incubated for 3.5 h to attain complete hybridization. Wells 1a, 1b, 2a, and 2b were functionalized with ssDNA-10b, whereas 1c and 2c were functionalized with ssDNA-10a and ssDNA-21, respectively. In all cases, PEG6-SH was used as a spacer. A positive control experiment was conducted by incubating the sensor with 100 μM of mixed miRs (miR-16, miR-126, miR-141, and miR-122) which are not complementary to ssDNA-10b but no $\Delta\lambda$LSPR was detected (data not shown). A negative control experiment was conducted by incubating a sensor in human plasma only, and no apparent $\Delta\lambda$LSPR was detected (data not shown). The $\lambda_{LSPR}$ red-shift in the plate reader measurement (FIG. 27B) suggested attachment of miR to form the duplex on the surface of the nanoprisms. Changes in the λLSPR of gold nanoprisms before (black) and after (--- -) functionalization with mixed HS-PEG6:HS-C6-ssDNA-10b. The $\lambda_{LSPR}$ after incubation in 100 μM miR-10b (------- ------) in human plasma resulted in 9.6 nm $\Delta\lambda$LSPR shift. We obtained an average 6.2 nm shift for 1 fM (data not shown). All the spectra were collected in air. The spectra for other miRs are not shown. Measurements were conducted with a standard plate reader in the absorption mode. The graph shows an average measurement of six spots in the same well.

To enhance portability, commercially available PET-bottom multiwell plates (Millipore, USA) replaces the fragile glass and similar surface functionalization chemistry is used to prepare the plastic LSPR-based sensor as proposed above. Next, the surface of the nanoprisms is functionalized with distinct probe molecules (ssDNAs) targeting different miRs (multiplexing) in an array format so that a large range of concentrations (10 nM to 10 zM) are examined to determine the LODs and to provide the first LSPR-based sensors for multiplexed quantification of various miRs almost in real-time at zM concentrations. Various miRs (e.g., miR-106b, miR- 212, miR-30c, miR-7a, miR-7c, miR-29a, and miR-29b) relevant to various cancers are employed. Although current miR-based biological research focuses on over-expressed miRs, the ability to assay miRs at ultra-low concentrations is expected to both reveal previously unknown, low concentration miRs that play crucial roles in RNA biology and to permit monitoring of miRs that are under-expressed in particular cancers. To demonstrate this aspect of the technology, miR-7a and miR-29a, each with a single nucleotide mismatches, miR-7c and miR- 29b, respectively, under-expressed in pancreatic cancer, are assayed.

Figure 28:
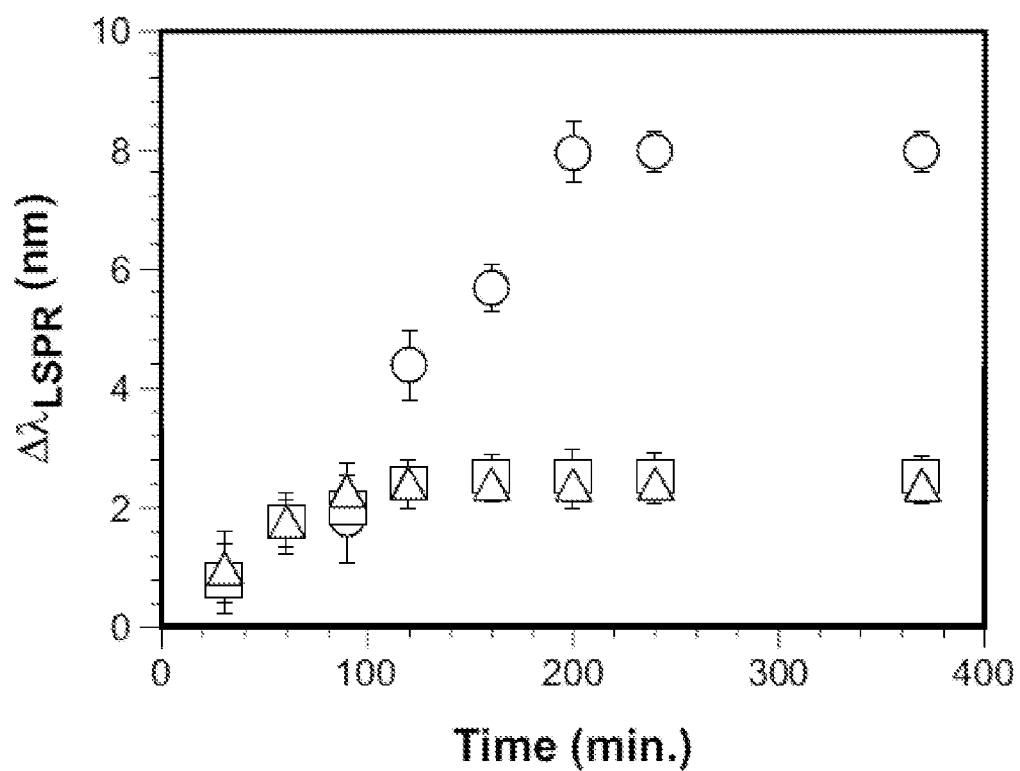
FIG. 28 is a graph showing time dependent $\Delta\lambda_{LSPR}$ shifts as a function of miR-10b concentration, circles (100 µM) and squares (100 aM) at 22° C., and triangles (100 aM) at 4° C. A positive control experiment was conducted by incubating just the substrate bound nanoprisms with 100 µM of miR-10b and no change was observed (data not shown).

To achieve the high-throughput ability of our LSPR-based sensors, instead of 6 wells, 96 well plates are used to reduce the sample volume from 400 to -20 μL. High-throughput is also achieved by reducing analysis time. Although an overnight incubation of LSPR-based sensors in miR solution under normal laboratory condition (22° C.) was reported, FIG. 28 shows that maximum $\Delta\lambda_{LSPR}$ occurred within 3.5 h of incubation of our sensors in a 100 μM miR-10b solution and the time becomes shorter for lower concentration (2.5 h for 100 aM). This is expected since miRs hybridize with ssDNA faster at lower concentration due to less repulsion. Importantly, for 100 aM, the same $\Delta\lambda_{LSPR}$ value was observed within 90 min at 4° C. The kinetic data agree with the literature, which states that faster and more stable DNA/RNA hybridization occurs at lower temperatures. However, the possibility for non-specific hybridization also increases, particularly for those miRs with single nucleotide specificity. One can determine temperatures between about 4°-about 22° C. at which non-specific attachment is minimal or absent, while DNA/miR hybridization time is reduced by conducting control experiments to determine the specificity of our LSPR-based sensors at temperatures <22° C. using an ssDNA of interest, such as ssDNA-10b, as a standard probe. Several miRs (100 μM total concentration) that are not complementary to the probe can be mixed the $\Delta\lambda_{LSPR}$ determined. No change in the value is expected. 100 μM human plasma solution of miR-10a, which has one nucleotide difference with miR-10b, is used as analyte and the ideal temperature at which the sensor does respond is determined.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

Example 3

Multiplexing Biosensors for Quantitative Detection of microRNAs Directly from Unmodified Cancer Patients Plasma A bottomless 96 well plate was coupled to a glass bottom was used to demonstrate the multiplexing and high-throughput capabilities of the disclosed biosensors. Each well contained at least one biosensor functionalized with ss-DNA and spacers. In an exemplary scheme, the rows of wells contained the same a biosensor with the same functionalized ss-DNA, and each column was dedicated to a patient's sample. Accordingly, in one exemplary scheme, ten different patient samples were tested against five different micro-RNAs. See FIG. 33(G), 33(F), and 35.

Materials. Chloro(triethylphosphine) gold (I) ($Et_3PAuCl$, 97%) and $HAuCl_4$ was purchased from Gelest Inc. Poly (methylhydrosiloxane) (PMHS, Mn=1700-3300), triethylamine (TEA, 98%), sodium citrate, hexadecyltrimethylammonium bromide (CTAB), D-(+)-Glucose, HEPES, sodium borohydride, silver nitrate, L(+)-Ascorbic acid, ACS grade acetonitrile ($CH_3CN$, 99.9%), and methanol (99.8%) were purchased from Sigma-Aldrich. (3-Mercaptopropyl)-trimethoxysilane (MPTMS, 94%) and (3-aminopropyl)triethoxysilane (APTES, 98%) was purchased from Alfa Aesar. Ethanol (200 proof) was purchased from Decon labs. Thiolated polyethylene glycols were purchased from purePEG. Thiol modified 3'-SH—$(CH_2)_3$-ssDNAs, microRNAs, and RNase H enzyme was purchased from Integrated DNA Technologies (IDT). All chemicals were used without further purifications. RNase free sterile water was obtained from Baxter Healthcare Corporation. 18×18 mm glass coverslips were purchased from Fisher Scientific. RBS 35 Detergent was obtained from Thermo Scientific and used as received. No-bottom 96-multiwell plates were purchased from Greiner Bio-One. Krazy Glue was purchased from Office Depot. All water was purified using a Thermo Scientific Barnstead Nanopure system. Thiol modified -ssDNAs, microRNAs, and patient samples were stored at −80° C. PBS buffer (pH=7.2) was prepared using RNase free sterile water. Ethanol was purged $N_2$ with for 30 min prior to use.

Figure 30:
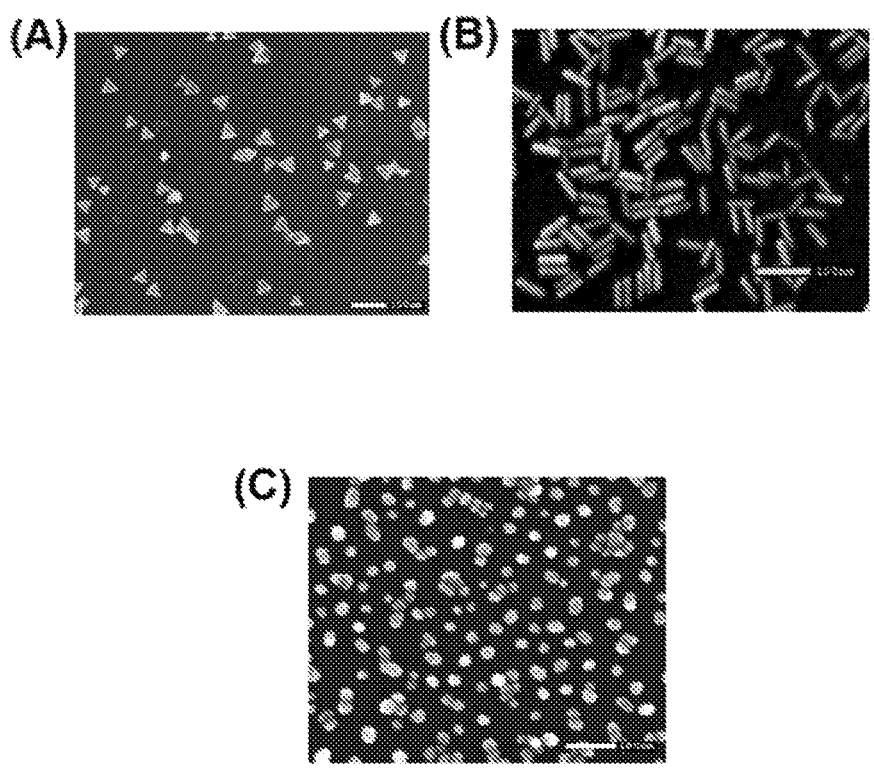
FIG. 30A-C show SEM images, wherein (A) is Au TNPs, (B) is Au nanorods, and (C) is Au spherical particles.

Spectroscopy and Microscopy Characterizations. Absorption and extinction spectra in the range of 400-1000 nm were collected with a SpectraMax M5 microplate reader from Molecular Devices LLC. Au TNP extinction spectra were measured in PBS buffer and Au SNP and Au NR extinction spectra were measured in water at room temperature to keep the refractive index of the bulk medium constant. Here, a blank glass coverslip immersed in PBS buffer/water was used as a background and a plasmonic nanoantenna-based biosensor incubated in PBS buffer/water was considered the reference (i.e., blank). The chemically synthesized Au TNPs, NRs, and SNPs attached onto the silanized glass coverslips inside the multiwell plates were characterized using scanning electron microscopy (SEM). See FIGS. 30(A)-(C).

Silanization of Glass Coverslips. Glass coverslips with 18×18 mm dimension were functionalized according to our previously published procedure. Glass coverslips were incubated in a 10% (v/v) aqueous RBS 35 detergent solution at 90° C. for 10 minutes. After rinsing multiple times with nanopure water, the coverslips were incubated in a 1:1 (v/v) hydrochloric acid: methanol solution for 30 minutes. The coverslips were then rinsed several times with nanopure water and dried overnight in a vacuum oven at 60° C. The following day, the coverslips were allowed to cool to room temperature, and then were incubated in a 15% (v/v) solution of MPTMS or APTES in ethanol for 30 min. The coverslips were then rinsed 3-5 times by sonicating in ethanol for 10 min. After rinsing, the coverslips were baked in a vacuum oven at 120° C. for at least 3 hr. The prepared MPTMS/APTES functionalized coverslips were then stored at 4° C. up to one week.

Synthesis of Gold Triangular Nanoprisms (Au TNPs). Au TNPs were chemically synthesized according to our previously developed procedure with minor modification. Briefly, $Et_3PAu(I)Cl$ (18.0 mg, 0.05 mmol) was dissolved in 40 mL of N2 purged $CH_3CN$ and allowed to stir for 10 min at room temperature. Next, 0.038 mL (0.273 mmol) of TEA was injected into the gold salt solution and the solution temperature was raised to 40° C. Next, 0.6 mL of PMHS was added and the reaction was allowed to proceed with slow magnetic stirring. During the reaction, the color of the solution changed from colorless to pink, purple, and then light blue. At this point, the solution temperature was raised to 45° C. and was allowed to run until a dark blue color appeared, indicating the formation of Au TNPs, which should display a stable localized surface plasmon resonance (LSPR) dipole peak (QLSPR) position at 800 nm in $CH_3CN$. The solution was then removed from heat and centrifuged at 7000 rpm for 10 sec. Finally, previously prepared MPTMS-functionalized coverslips were incubated in the freshly synthesized Au TNPs solution for 1 hr, followed by copious rinsing with acetonitrile, dried under $N_2$ flow, and then stored under nitrogen at 4° C. An SEM image of Au TNPs is provided in FIG. 30(A).

Synthesis of Gold Spherical Nanoparticles (Au SNPs). A 10 mL $HAuCl_4$ $H_2O$ solution (4 mg/mL) was added to 390 mL $H_2O$ in a 3 L round bottom flask. The temperature was then slowly increased until the solution started to boil. At this point, 3 mL aqueous solution of sodium citrate (10 mg/mL) was quickly injected. The reaction was allowed to proceed for 5 min while stirring, and then the heat source was removed and the red solution was allowed to cool. Next, previously prepared APTES-functionalized coverslips were incubated in the freshly synthesized Au SNPs overnight. After incubation, the glass coverslip-attached gold spherical nanoparticles were rinsed with water, dried under nitrogen flow, and stored under $N_2$ at 4° C. An SEM image of Au SNPs is provided in FIG. 30 (C).

Synthesis of Gold Nanorods (Au NRs). Au NRs were chemically synthesized via a seeding method as reported in the literature. Briefly, seed solution was prepared first. A 0.25 mL of 10 mM $HAuCl_4$ solution was added to 7.5 mL of 100 mM CTAB solution in a 20 mL glass vial at room temperature and allowed to stir for 5 min. Next, 0.6 mL of 10 mM $NaBH_4$ solution was added and allowed to stir for an additional 15 min that resulted in a light brown solution. The growth solution was prepared as follows: A 28 mL of 100 mM CTAB solution was placed in a 50 mL centrifuge tube and 2 mL of 10 mM $HAuCl_4$ solution was added to it, followed by the addition of 0.4 mL of 10 mM $AgNO_3$ solution, and finally 0.22 mL of 100 mM ascorbic acid successively. Once the ascorbic acid was added, the solution turned colorless. At this point, 48 μL of the seed solution was added and then incubated overnight at room temperature. During this time, the color change observed from clear to a dark pink. The Au NRs were isolated through centrifugation at 9000 rpm for 30 min. This purification was repeated twice. After the final purification, previously prepared MPTMS-functionalized coverslips were incubated in the purified Au NR solution for 8 hr. After incubation, the glass coverslip-attached Au NRs were rinsed with water, dried under nitrogen flow, and stored under $N_2$ at 4° C. An SEM image of Au NRs is provided in FIG. 30(B).

Bottom-Up Fabrication of Plasmonic Nanoantenna-Based Biosensors for Multiplexed and High-throughput microRNA Assay. FIG. 29 provides an exemplary scheme for multiplexed and high-throughput miR Assay. Schematic representation of the fabrication of multiplexing sensors for assaying numerous microRNAs using a 96 well plate. (A) A no-bottom 96 well plate. (B) Chemically synthesized Au TNP functionalized glass coverslip. (C) A 96 well plate with the functionalized glass coverslips glued to the bottom. (D) 96 well plate incubated in 1:1 ratio solution of -ss-DNA-3'-$C_3SH$ and $PEG_4$-SH. (E) 96 well plate incubated in different fully complimentary microRNA biomarkers. Patient samples would be incubated here after point E. As described previously, we performed a tape-cleaning procedure on the Au TNP-attached glass coverslips to remove non-prismatic nanostructures. Briefly, tape cleaning was performed by placing the adhesive scotch tape (3M corporation) onto the Au TNP-attached coverslips, gently pressed down with a finger, and then slowly removed at a 900 angle. The tape cleaned Au TNP-attached glass coverslips were then glued to a no-bottom 96-multiwell plate by applying a small amount of glue around the edges of the coverslip and gently placing it onto the bottom of the well plate. The attached coverslips were allowed to dry for at least 2h at room temperature. Each well was then incubated in 0.3 mL of a 1:1 ratio (1 μM each) of 3'-SH—$(CH_2)_3$-ssDNA: $PEG_4$-SH PBS buffer solution overnight. The next morning, each well was rinsed with PBS buffer to remove loosely bound reactants and then used for the assay. An identical fabrication method was followed for Au NRs and Au SNPs. No tape cleaning procedure was performed for NRs and SNPs.

Refractive Index Unit Sensitivity Measurements. Refractive index unit (RIU) sensitivity was measured for the plasmonic nanostructures by using the following procedure. After bottom-up fabrication of each plasmonic nanostructure attached onto a functionalized glass substrate was performed, each well was incubated in 300 μL of water for 15 minutes. Once the incubation time was finished, an LSPR extinction spectra was obtained. This process was then repeated for different concentrations of glucose media (0%, 10%, 15%, 20%, 30%, and 50%). Once all LSPR extinction spectra were taken, the wavelength maximum was recorded for each solution and graphed verses the refractive index of the solution. Linear regression was then performed using Excel and the RIU sensitivity (slope of regression equation) was obtained. The LSPR extinction spectra of Au TNPs, Au NRs, and Au SNPs attached onto a functionalized glass substrate was also obtained in air. See FIG. 34(A)-(C).

Figure 31:
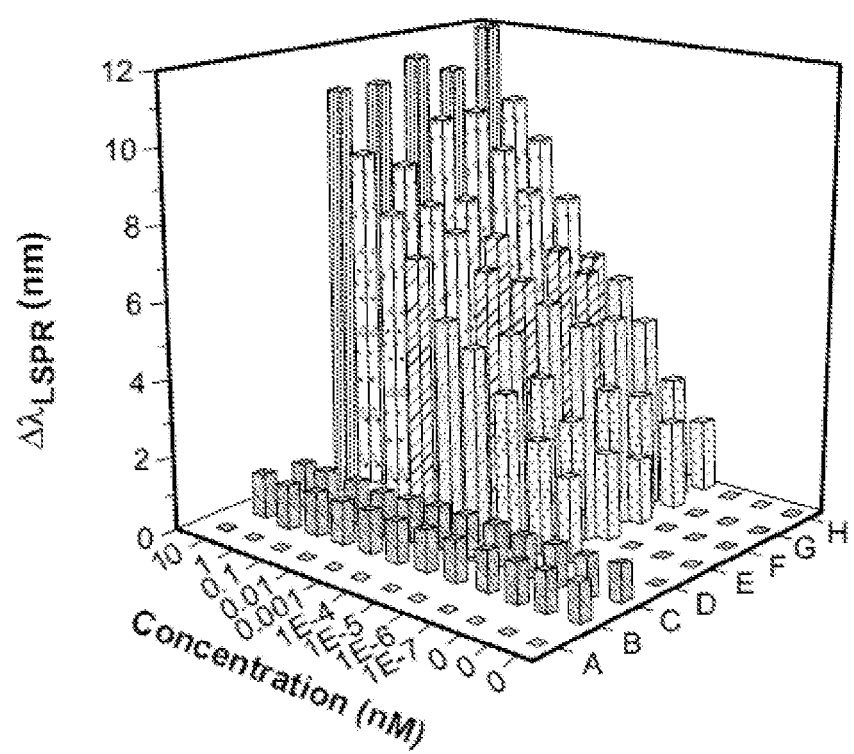
FIG. 31 is a three-dimensional graph showing the average $\Delta\lambda_{LSPR}$ value of nanoplasmonic sensors on a 96 well plate after incubation of different microRNAs of varying concentrations in human plasma, wherein each type of nanoplasmonic sensor was constructed with corresponding -ssDNA as a receptor molecule, and wherein A=blank, B=false positive, C=false negative, D=microRNA-145, E=microRNA-143, F=microRNA-490-5p, G=microRNA-10b, and H=microRNA-96.

Development of microRNA Calibration Plots in Buffer and Human Plasma. The LSPR extinction spectra of plasmonic nanoantenna-based biosensors were collected in PBS buffer to determine $\lambda_{LSPR}$. Then, the nanoplasmonic sensors were incubated in a 0.3 mL microRNA solution of different concentrations (range of 10 nM to 100 aM) in PBS buffer (or 10 μL human plasma in 0.29 mL PBS buffer) overnight. MicroRNA-bound biosensors were washed with PBS buffer to remove any nonspecifically adsorbed biomolecules, and the LSPR extinction spectra were collected and $\lambda_{LSPR}$ was determined. False positive analysis was conducted by incubating the plasmonic nanoantenna-based biosensors with only PEG attached in a 0.3 mL, 10 nM non-complimentary microRNA solution. False negative analysis was conducted by incubating the plasmonic nanoantenna-based biosensors in 1 uM -ssDNA followed by incubation in 0.3 mL PBS buffer. See FIG. 31.

Figure 33:
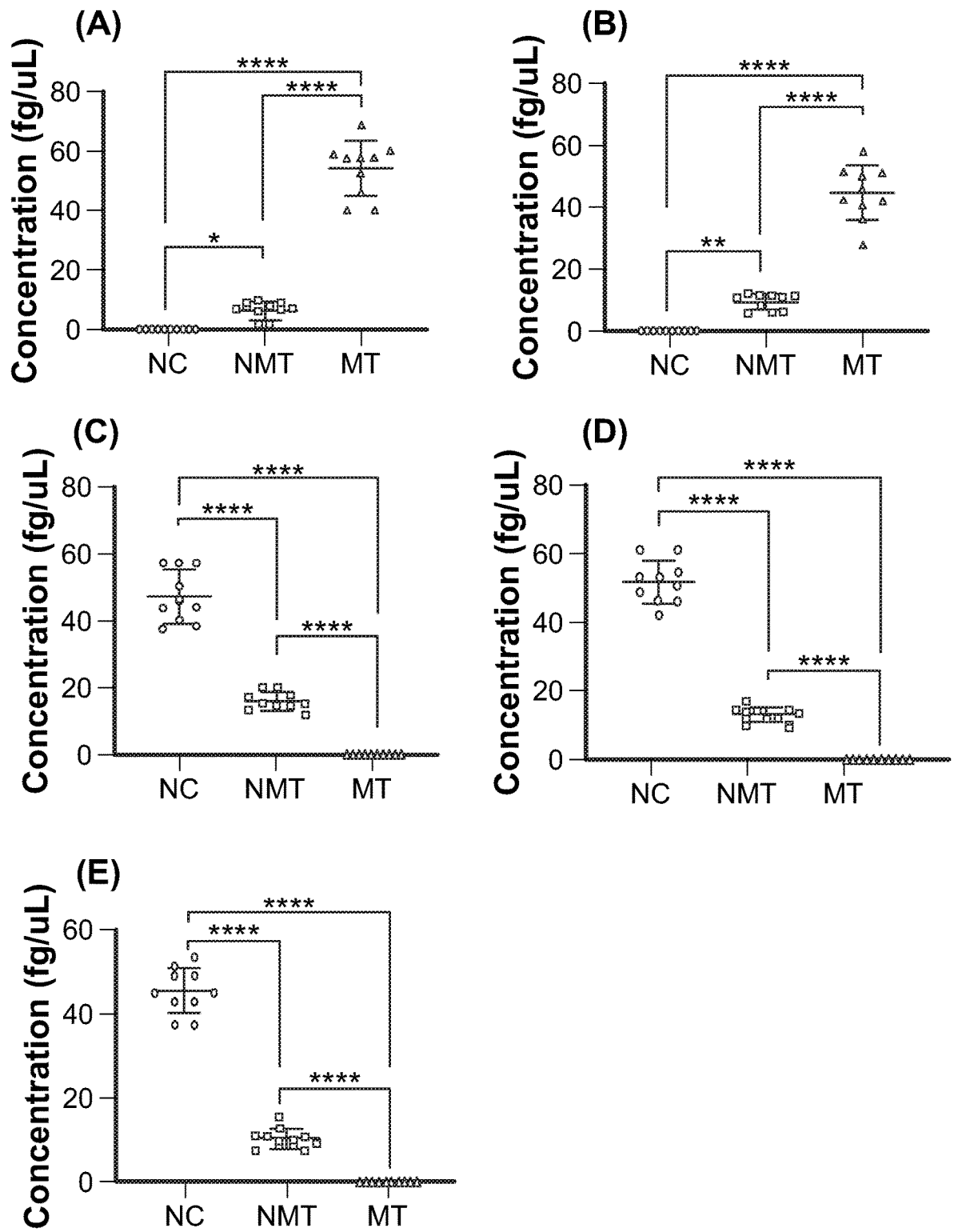
FIG. 33A-G are graphs showing ANOVA results from patient data depicting the normal control versus non-metastic bladder cancer versus metastatic bladder cancer patient samples for (A) microRNA-10b, (B) microRNA-96, (C) microRNA-145, (D), microRNA-143, and (E) microRNA-490-5p. (F) shows a three-dimensional representation of non-metastatic patient samples and (G) shows metastatic patient samples, wherein A=blank, B=false positive, C=false negative, D=microRNA-145, E=microRNA-143, F=microRNA-490-5p, G=microRNA-10b, H=microRNA-96.
Figure 33:
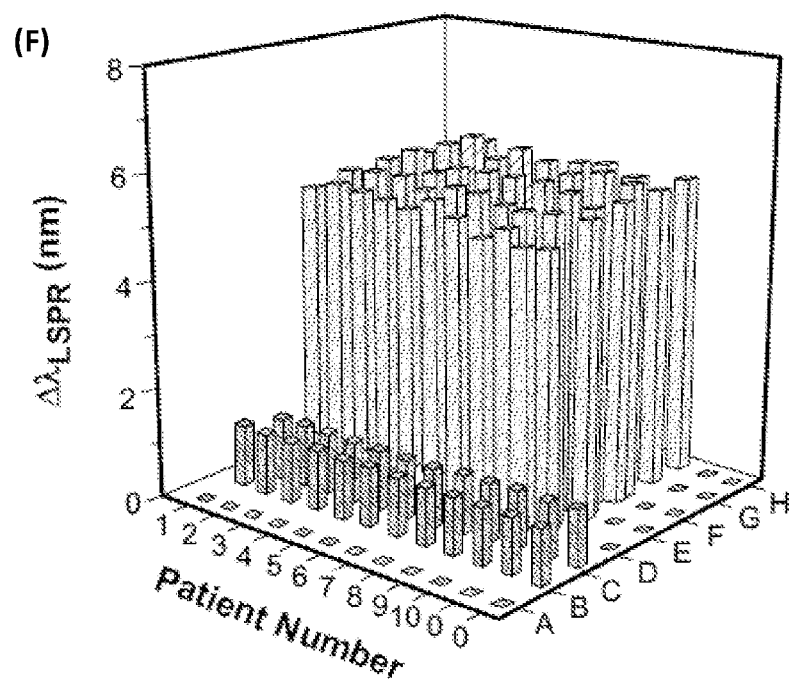
Figure 33:
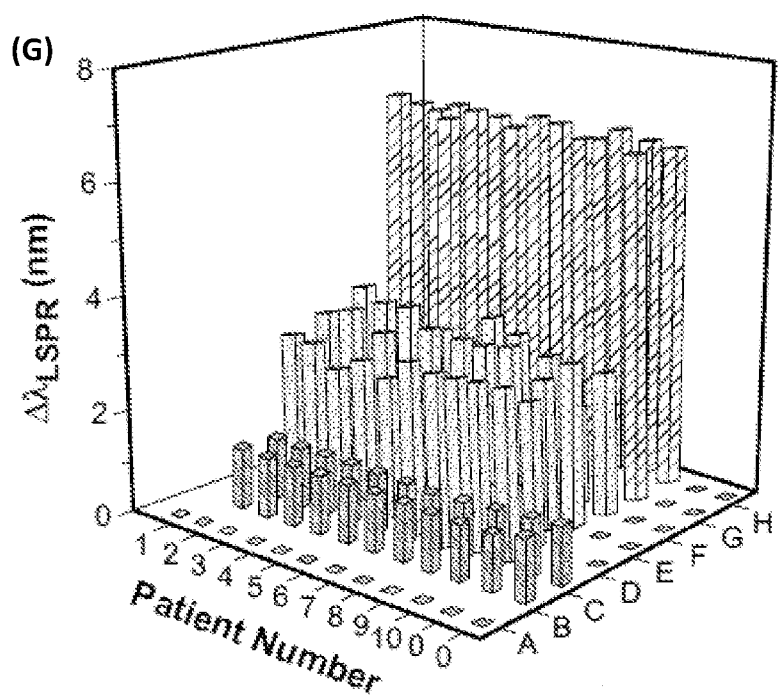
Figure 35:
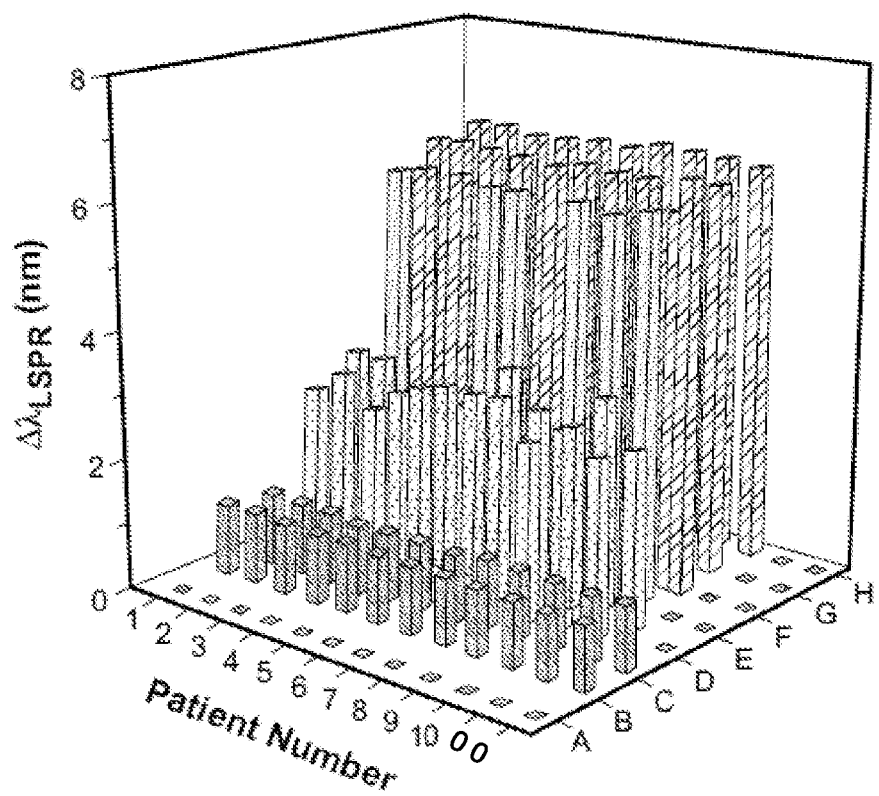
FIG. 35 is a graph showing a three-dimensional representation of normal control patient data with A=blank, B=false positive, C=false negative, D=microRNA-10b, E=microRNA-96, F=microRNA-145, G=microRNA-143, H=microRNA-490-5p.

Quantification of microRNA in Bladder Cancer Patient Samples. Plasmonic nanoantenna-based biosensors were incubated in a solution containing 10 μL of bladder cancer patient plasma (MT/NMT/Normal control samples) diluted with 0.29 mL PBS buffer for 24 hr and then the biosensors were thoroughly washed with PBS buffer to remove any nonspecifically adsorbed biomolecules. The LSPR extinction spectra were recorded, and $\lambda_{LSPR}$ was determined for each patient/microRNA. See FIG. 33 showing patient samples ANOVA results of normal control verses non-metastatic verses metastatic patient samples for microRNA-10b (A), microRNA-96 (B), microRNA-145 (C), microRNA-143 (D), and microRNA-490-5p (E). (F) 3D representation of non-metastatic patient samples (G) and metastatic patient samples, wherein for each 3D graph A=blank, B=false positive, C=false negative, D=microRNA-145, E=microRNA-143, F=microRNA-490-5p, G=microRNA-10b, and H=microRNA-96. See Table 33 for the ss-DNA oligomers and Table 34 for the miR of interest identified in the multiplexing, high-throughput patient sample experiment For comparison, ten normal patient samples were also analyzed using the biosensor arrays. FIG. 35 shows a 3D representation of the micro-RNA analysis in the ten normal patient plasma samples, wherein A=blank, B=false positive, C=false negative, D=microRNA-10b, E=microRNA-96, F=microRNA-145, G=microRNA-143, and H=microRNA-490-5p.

Figure 32:
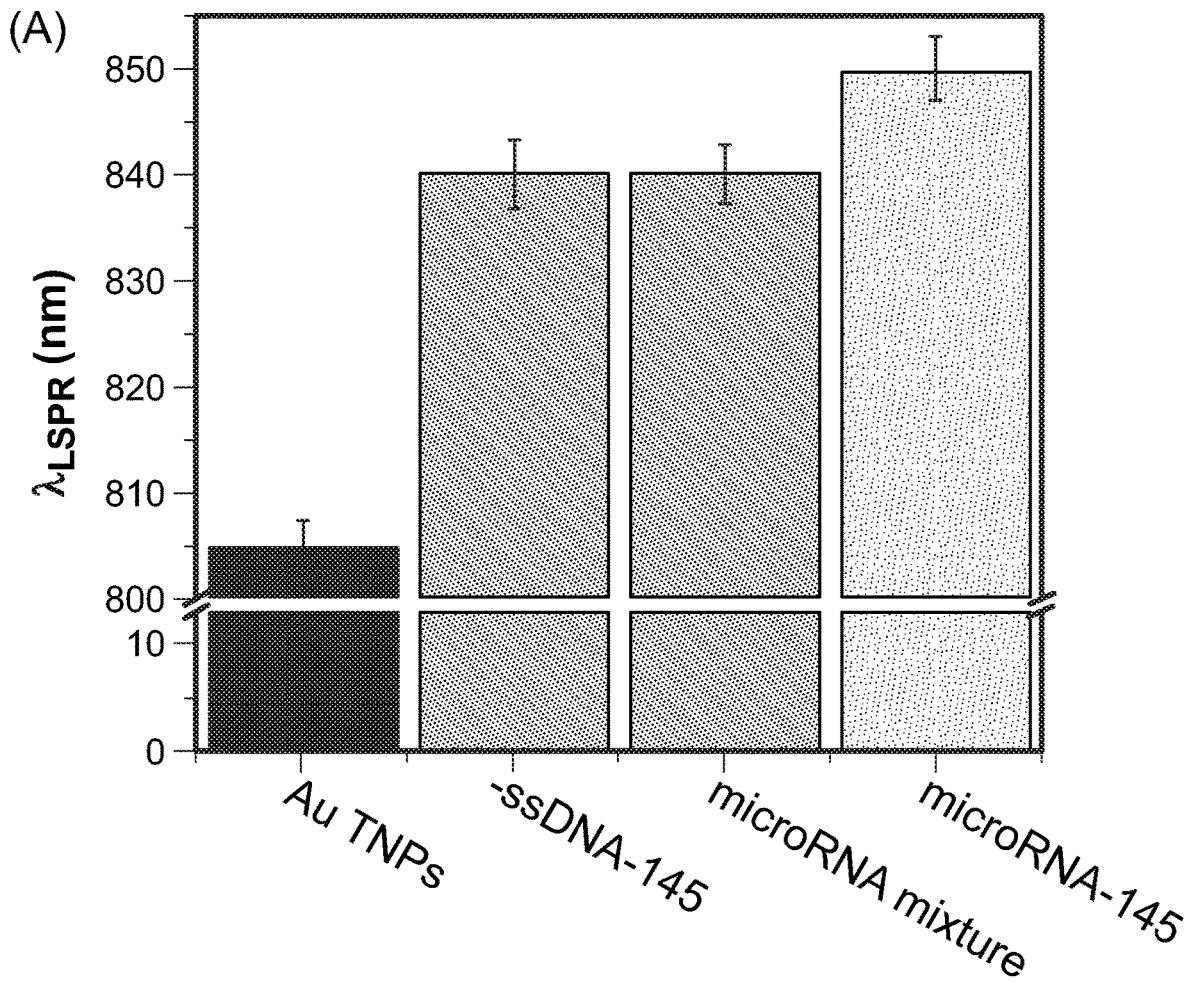
FIG. 32A-B show specificity and reversibility tests, wherein (A) shows UV-visible extinction spectra of Au TNPs before (first bar, black), after mixed—S-PEG$_4$: —S—(CH$_2$)$_3$-ssDNA-145 (second bar) functionalization, after incubation in a mixed solution of 100.0 nM concentration microRNA-10b, microRNA-96, microRNA-490-5p, and microRNA-143 (third bar), and after incubation in 10 nM microRNA-145 (fourth bar). All spectra were collected in PBS buffer (pH=7.2). (B) shows a representation of the reversibility results, showing the biosensor (Au TNPs functionalized with —S-PEG$_4$: —S—(CH$_2$)$_3$-ssDNA-10b) is reversible up to 5 trials with trial 1 representing -ssDNA-10b incubation, trial 2, 4, 6, 8, and 10 representing microRNA-10b incubation, and trial 3,5,7, and 9 representing RNase H enzyme incubation.
Figure 32:
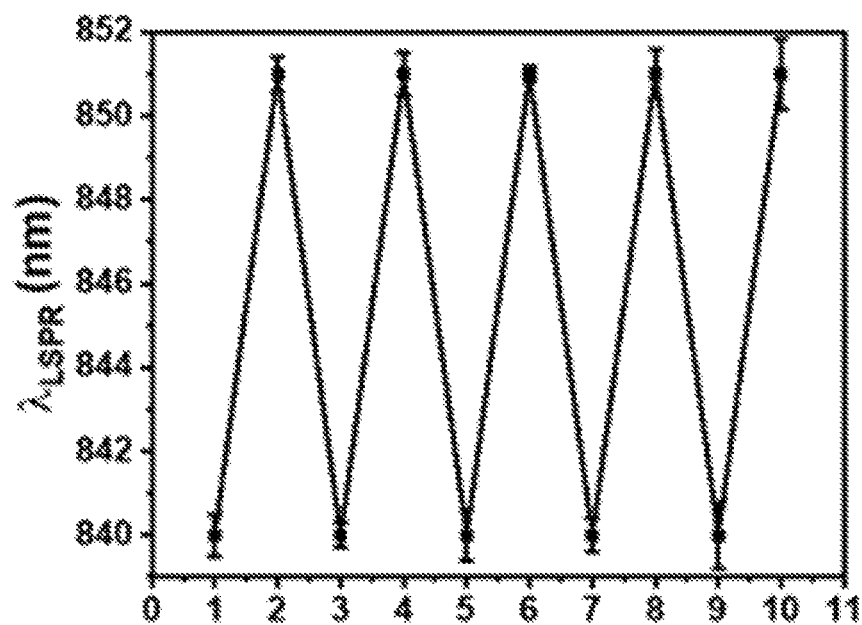

FIG. 32 shows the ability to regenerate the biosensor after the ss-DNA has bound to its miR of interest and the specificity of the biosensor. An example of this regeneration process using RNAse H is provided in Example 2.

Data Processing and Statistical Analysis. The $\lambda_{LSPR}$ was obtained by using the maxima of the UV-visible extinction spectra (determined through curve fitting using Origin software) and $\Delta\lambda_{LSPR}$ was derived by taking the difference between the $\lambda_{LSPR}$ of the plasmonic nanoantenna-based biosensors before and after hybridization with target microRNA. Calibration curves were obtained by plotting $\Delta\lambda_{LSPR}$ vs. microRNA concentration, with concentration being plotted on the axis in log scale in order to investigate non-specific adsorption at a lower concentration range. The calibration curve equation was determined through linear regression on Excel. Finally, the LOD was determined by using a Z value of the blank (Z=mean+3σ, σ=standard deviation), which was obtained from six $\Delta\lambda_{LSPR}$ measurements using three different biosensors and plugging the Z value into the "Y" in the calibration curve equation and obtaining the LOD concentration ("X"). Concentration of target microRNAs in patient samples were determined from the calibration curves developed in plasma, with $\Delta\lambda_{LSPR}$ value and corresponding concentrations obtained from the average of six measurements. Each sample was independently analyzed twice (two weeks apart). Ordinary one-way ANOVA and area under the curve (AUC) of the receiver operating characteristic (ROC) graphs were plotted using GraphPad Prism. Ordinary one-way ANOVA used the following p value style: 0.1234 (ns), 0.0332 (*), 0.0021 (), 0.0002 (*), <0.0001 (****), and was performed at the 95% confidence interval. AUC of ROC was also performed at the 95% confidence interval.

TABLE 33

DNA (oligomer) sequences used for this study.

| Name | Sequence | SEQ ID NO: | Modification |
|---|---|---|---|
| -ssDNA-10b | 5' CAC AAA TTC GGT TCT ACA GGG TA 3' | 13 | 3' Thiol-(CH$_2$)$_3$ |
| -ssDNA-96 | 5' AGC AAA AAT GTG CTA GTG CCA AA 3' | 28 | 3' Thiol-(CH$_2$)$_3$ |
| -ssDNA-145 | 5' AGG GAT TCC TGG GAA AAC TGG AC 3' | 15 | 3' Thiol-(CH$_2$)$_3$ |
| -ssDNA-143 | 5' CCT CGT CAC GAC GTA GAG ACC A 3' | 16 | 3' Thiol-(CH$_2$)$_3$ |
| -ssDNA-490-5p | 5' ACC CAC CTG GAG ATC CAT GG 3' | 29 | 3' Thiol-(CH$_2$)$_3$ |

TABLE 34 microRNA sequences used for this study.

| Name | Sequence | SEQ ID NO: | Modification |
|---|---|---|---|
| microRNA-10b | 5' UACCCUGUAGAACCGAAUUUGUG 3' | 4 | N/A |
| microRNA-96 | 5' UUUGGCACUAGCACAUUUUUGUG 3' | 30 | N/A |
| microRNA-145 | 5' GUCCAGUUUUCCCAGGAAUCCCU 3' | 19 | N/A |
| microRNA-143 | 5' GGUGCAGUGCUGCAUCUCUGGU 3' | 20 | N/A |
| microRNA-490-5p | 5' CCAUGGAUCUCCAGGUGGGU 3' | 31 | N/A |

We claim:

1. A biosensor comprising:
   a substrate having a substrate surface to which a localized surface plasmon resonance (LSPR) antenna is affixed, the LSPR antenna affixed via an affixation surface of the LSPR antenna,
   the LSPR antennae having a functional surface opposite the affixation surface, the functional surface functionalized by a plurality of single-stranded DNA (ssDNA), the ssDNA comprising a thiol functional moiety comprising a chain of 3, 4, 5, 7, 8, or 9 carbons,
   wherein the ssDNA is complementary to at least a portion of a miRNA (miR) of interest.

2. The biosensor of claim 1, wherein the ssDNA is complementary to at least a portion of the miR of interest but comprises exactly one mismatch relative to the portion of the miR of interest.

3. The biosensor of claim 1, wherein the functional moiety is located at a terminal end of the ssDNA.

4. The biosensor of claim 1, wherein the functional surface is further functionalized by a plurality of spacer molecules.

5. The biosensor of claim 4, wherein the plurality of spacer molecules comprise a poly-ethylene glycol moiety, an alkyl moiety, or a combination thereof.

6. The biosensor of claim 4, wherein the plurality of spacer molecules comprise a thiol functional moiety, an amine functional moiety, a carboxylate functional moiety, a phosphonate functional moiety, or a combination thereof.

7. The biosensor of claim 4, the functional surface having a ratio of number of ssDNA to number of spacer molecules between 1:99 and 99:1.

8. The biosensor of claim 7, wherein the ratio of number of ssDNA to number of spacer molecules is between 1:2 and 2:1.

9. The biosensor of claim 8, wherein the ratio of number of ssDNA to number of spacer molecules is 1:1.

10. The biosensor of claim 1, wherein the LSPR antenna comprises gold, silver, copper, palladium, aluminum, or a combination thereof.

11. The biosensor of claim 1, wherein the LSPR antenna is a nanoprism.

12. The biosensor of claim 1, wherein the functional surface is substantially triangular.

13. The biosensor of claim 1, wherein the LSPR antenna has an average edge-length of between 10 nm and 150 nm.

14. The biosensor of claim 1, wherein the LSPR antenna has an average edge-length of between 30 and 50 nm.

15. The biosensor of claim 1, wherein the substrate is substantially transparent to electromagnetic radiation having a wavelength between 350 nm and 1200 nm.

16. The biosensor of claim 1, wherein the substrate is substantially transparent to electromagnetic radiation having a wavelength between 700 nm and 900 nm.

17. The biosensor of claim 1, wherein the substrate comprises glass, quartz, indium tin oxide, optical fiber, flexible plastic, gold-coated glass, sapphire, or a combination thereof.

18. The biosensor of claim 1, wherein the LSPR antenna has an unbound absorption peak wavelength when contacted by a medium lacking the miR of interest, that has a sequence that is at least partially complementary to the ssDNA and a bound absorption peak wavelength when contacted by a medium containing the miR of interest, wherein the bound absorption peak wavelength is shifted relative to the unbound absorption peak wavelength by an amount proportional to the concentration of the miR of interest in the medium, and wherein the miR of interest has a sequence that is at least partially complementary to the ssDNA.

19. The biosensor of claim 1, wherein the ssDNA comprising a thiol functional moiety comprising a chain of 4, 5, 7, 8, or 9 carbons.

* * * * *

SEQUENCE LISTING

<160> NUMBER OF SEQ ID NOS: 31

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcaacatcag tctgataagc ta                                            22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cacaaattcg gttctacagg gta                                           23

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uagcuuauca gacugauguu ga                                            22

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uacccuguag aaccgaauuu gug                                           23

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uagcagcacg uaaauauugg cg                                            22

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cauuauuacu uuugguacgc g                                             21

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uaacacuguc ugguaaagau gg                                             22

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uggaguguga caaugguguu ug                                             22

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uacccuguag auccgaauuu gug                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cacaaattcg gttctacagg gta                                            23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgtgagttct accattgcca aa                                             22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agggattcct gggaaaactg gac                                            23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacaaattcg gttctacagg gta                                              23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgtgagttct accattgcca aa                                               22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agggattcct gggaaaactg gac                                              23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cctcgtcacg acgtagagac ca                                               22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cacaaattcg gttctacagg gta                                              23

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuuggcaaug guagaacuca ca                                               22

```
<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
guccaguuuu cccaggaauc ccu                                              23

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggugcagugc ugcaucucug gu                                               22

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uacccgguag aaccgaauuu gug                                              23

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uacccuguag aaccgaauuc gug                                              23

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uacccuguag aaccgaauuu                                                  20

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuugacaaug guagaacuca ca                                               22

<210> SEQ ID NO 25
```

```
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuuggcaaug auagaacuca ca                                              22

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuuggcaaug guagaacuaa ca                                              22

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuuggcaaug guagaacuc                                                  19

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agcaaaaatg tgctagtgcc aaa                                             23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acccacctgg agatccatgg                                                 20

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uuuggcacua gcacauuuuu gug                                             23

<210> SEQ ID NO 31
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ccauggaucu ccaggugggu                                                    20
```